(12) United States Patent
Smolke et al.

(10) Patent No.: US 9,534,241 B2
(45) Date of Patent: Jan. 3, 2017

(54) BENZYLISOQUINOLINE ALKALOIDS (BIA) PRODUCING MICROBES, AND METHODS OF MAKING AND USING THE SAME

(71) Applicant: The Board of Trustees of the Leland Stanford Junior University, Palo Alto, CA (US)

(72) Inventors: Christina D. Smolke, Menlo Park, CA (US); Catherine Thodey, Sunnyvale, CA (US); Isis Trenchard, Redwood City, CA (US); Stephanie Galanie, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 20 days.

(21) Appl. No.: 14/211,611

(22) Filed: Mar. 14, 2014

(65) Prior Publication Data

US 2014/0273109 A1  Sep. 18, 2014

Related U.S. Application Data

(60) Provisional application No. 61/788,560, filed on Mar. 15, 2013.

(51) Int. Cl.
*A61K 31/472* (2006.01)
*C07D 489/02* (2006.01)
*C07D 217/04* (2006.01)
*C12P 17/18* (2006.01)
*C12N 9/10* (2006.01)
*C12N 15/52* (2006.01)

(52) U.S. Cl.
CPC ............ *C12P 17/18* (2013.01); *C12N 9/1007* (2013.01); *C12N 15/52* (2013.01); *C12P 17/182* (2013.01)

(58) Field of Classification Search
CPC combination set(s) only.
See application file for complete search history.

(56) References Cited

U.S. PATENT DOCUMENTS

| | | |
|---|---|---|
| 7,193,127 B1 | 3/2007 | Kutchan et al. |
| 7,390,642 B2 | 6/2008 | Kutchan et al. |
| 8,975,063 B2 | 3/2015 | Smolke et al. |
| 8,993,280 B2 | 3/2015 | Sato et al. |
| 2005/0139490 A1 | 6/2005 | Chou et al. |
| 2007/0199090 A1 | 8/2007 | Apuya et al. |
| 2008/0176754 A1 | 7/2008 | Smolke et al. |
| 2015/0267233 A1 | 9/2015 | Smolke et al. |

FOREIGN PATENT DOCUMENTS

| | | |
|---|---|---|
| EP | 1512748 A1 | 3/2005 |
| EP | 1 837 396 | 9/2007 |
| JP | 2009/225669 | 10/2009 |
| WO | WO 2008/067070 | 6/2008 |
| WO | 2008067070 A3 | 10/2008 |
| WO | 2008153094 A1 | 12/2008 |
| WO | WO 2011/058446 | 5/2011 |
| WO | WO 2012/039438 | 3/2012 |
| WO | 2014143744 A2 | 9/2014 |
| WO | 2015066642 A1 | 5/2015 |
| WO | 2014143744 A3 | 11/2015 |

OTHER PUBLICATIONS

PhD Thesis, Metabolic Engineering of *Saccharomyces cerevisiae* for Polyhydroxybutyrate Production Kanokarn Kocharin Apr. 2013.*
Allen et al., "RNAi-Mediated Replacement of Morphine with the Nonnarcotic Alkaloid Reticuline in Opium Poppy", Nat. Biotechnol. (2004), 22:1559-1566.
Avalos et al., "Compartmentalization of Metabolic Pathways in Yeast Mitochondria Improves the Production of Branched-Chain Alcohols", Nat. Biotechnol. (2013), 31:335-341.
Backes et al., "Organization of Multiple Cytochrome P450s with NADPH-Cytochrome P450 Reductase in Membranes", Pharmacol. Ther. (2003), 98:221-233.
Bayer et al., "Synthesis of Methyl Halides from Biomass Using Engineered Microbes", J. Am. Chem. Soc. (2009), 131:6508-6515.
Beaudoin et al., "Isolation and Characterization of a cDNA Encoding (S)-cis-N-Methylstylopine 14-Hydroxylase from Opium Poppy, a Key Enzyme in Sanguinarine Biosynthesis", Biochem. Biophys. Res. Commun. (2013), 431:597-603.
Bruce et al., "Microbial Degradation of the Morphine Alkaloids. Purification and Characterization of Morphine Dehydrogenase from *Pseudomonas putida* M10", Biochem. J. (1991), 274(3):875-880.
Choi et al., "Molecular Cloning and Characterization of Coclaurine N-Methyltransferase from Cultured Cells of *Coptis japonica*", J. Biol. Chem. (2002), 277:830-835.
Diaz Chavez et al., "Characterization of two Methylenedioxy Bridge-Forming Cytochrome P450-Dependent Enzymes of Alkaloid Formation in the Mexican Prickly Poppy *Argemone mexicana*", Arch. Biochem. Biophys. (2011), 507:186-193.
Dumas et al., "11 Beta-Hydroxylase Activity in Recombinant Yeast Mitochondria. In vivo Conversion of 11-Deoxycortisol to Hydrocortisone", Eur. J. Biochem. (1996), 238:495-504.
Farhi et al., "Harnessing Yeast Subcellular Compartments for the Production of Plant Terpenoids", Metab. Eng. (2011), 13:474-481.
Farrow et al., "Dioxygenases Catalyze O-Demethylation and O,O-demethylenation with Widespread Roles in Benzylisoquinoline Alkaloid Metabolism in Opium Poppy", J. Biol. Chem. (2013), 288:28997-29012.
Fisinger et al., "Thebaine Synthase: a New Enzyme in the Morphine Pathway in *Papaver somniferum*", Natural Product Communications (2007), 2(3):249-253.

(Continued)

*Primary Examiner* — Kagnew H Gebreyesus
(74) *Attorney, Agent, or Firm* — Glenn J. Foulds; Bret E. Field; Bozicevic, Field & Francis LLP

(57) ABSTRACT

Aspects of the invention include host cells that are engineered to produce benzylisoquinoline alkaloids (BIAs). The host cells include heterologous coding sequences for a variety of enzymes involved in synthetic pathways from starting compounds to BIAs of the host cell. Also provided are methods of producing the BIAs of interest by culturing the host cells under culture conditions that promote expression of enzymes encoded by the heterologous coding sequences of the host cells. Aspects of the invention further include compositions, e.g., host cells, starting compounds and kits, etc., that find use in methods of the invention.

12 Claims, 23 Drawing Sheets

(56) References Cited

OTHER PUBLICATIONS

French et al., "Biological Production of Semisynthetic Opiates Using Genetically Engineered Bacteria", Biotechnology (N Y) (1995), 13:674-676.
French et al., "Purification and Characterization of Morphinone Reductase from Pseudomonas putida M10", Biochem. J. (1994), 301(1):97-103.
Geissler et al., "Molecular Modeling and Site-Directed Mutagenesis Reveal the Benzylisoquinoline Binding Site of the Short-Chain Dehydrogenase/Reductase Salutaridine Reductase", Plant Physiol. (2007), 143(4)1493-503.
Gesell et al., "Heterologous Expression of Two FAD-Dependent Oxidases with (S) Tetrahydroprotoberberine Oxidase Activity from Argemone mexicana and Berberis wilsoniae in Insect Cells", Planta. (2011), 233:1185-1197.
Grothe et al., "Molecular Characterization of the Salutaridinol 7-O-Acetyltransferase Involved in Morphine Biosynthesis in Opium Poppy Papaver somniferum", J. Biol. Chem. (2001), 276:30717-30723.
Nagel et al., "Benzylisoquinoline Alkaloid Metabolism: a Century of Discovery and a Brave New World", Plant Cell Physiol. (2013), 54:647-672.
Nagel et al., "Characterization of a Flavoprotein Oxidase from Opium Poppy Catalyzing the Final Steps in Sanguinarine and Papaverine Biosynthesis", J. Biol. Chem. (2012), 287:42972-42983.
Nagel et al., "Dioxygenases Catalyze the O-Demethylation Steps of Morphine Biosynthesis in Opium Poppy", Nat. Chem. Biol. (2010), 6:273-275.
Hawkins et al., "Production of Benzylisoquinoline Alkaloids in *Saccharomyces cerevisiae*", Nature Chemical Biology (2008), 4:564-573.
Higashi et al., "Atomic Structure of Salutaridine Reductase from the Opium Poppy (*Papaver somniferum*)", J. Biol. Chem. (2011), 286:6532-6541.
Ikezawa et al., "Molecular Cloning and Characterization of Methylenedioxy Bridge-Forming Enzymes Involved in Stylopine Biosynthesis in Eschscholzia californica", FEBS J. (2007), 274:1019-1035.
Ikezawa et al., "Molecular Cloning and Characterization of CYP719, a Methylenedioxy Bridge-Forming Enzyme that Belongs to a Novel P450 Family, from Cultured Coptis japonica Cells", J. Biol. Chem. (2003), 278:38557-38565.
Jensen et al., "Plant NADPH-Cytochrome P450 Oxidoreductases", Phytochemistry (2010). 71:132-141.
Kim et al., "Improvement of Reticuline Productivity from Dopamine by Using Engineered *Escherichia coli*", Biosci. Biotechnol. Biochem. (2013), 77(10):2166-2168.
Kushnirov, "Rapid and Reliable Protein Extraction from Yeast", Yeast (2000), 16:857-860.
Larkin et al., "Increasing Morphinan Alkaloid Production by Over-Expressing Codeinone Reductase in Transgenic Papaver somniferum", Plant Biotechnol. J. (2007), 5:26-37.
Lenz et al., "Acetyl Coenzyme a:Salutaridinol-7-O Acetyltransferase from Papaver somniferum Plant Cell Cultures", J. Biol. Chem. (1995), 270:31091-31096.
Lenz et al., "Purification and Properties of Codeinone Reductase (NADPH) from Papaver somniferum Cell Cultures and Differentiated Plants", Eur. J. Biochem. (1995), 233:132-139.
Liscombe et al., "Targeted Metabolite and Transcript Profiling for Elucidating Enzyme Function: Isolation of Novel N Methyltransferases from Three Benzylisoquinoline Alkaloid-Producing Species", Plant J. (2009), 60:729-743.
Minami et al., "Microbial Production of Plant Benzylisoquinoline Alkaloids", Proc. Natl. Acad. Sci. U S A (2008), 105:7393-7398.
Mizutani et al., "Diversification of P450 Genes During Land Plant Evolution", Annu. Rev. Plant Biol. (2010), 61:291-315.
Morishige et al., "Molecular Characterization of the Sadenosyl-L-Methionine:3'-Hydroxy-N-Methylcoclaurine 4'-O-Methyltransferase Involved in Isoquinoline Alkaloid Biosynthesis in Coptis japonica", J. Biol. Chem. (2000), 275:23398-23405.

Nakagawa et al., "A Bacterial Platform for Fermentative Production of Plant Alkaloids", Nat. Commun. (2011), 2:326.
Nakagawa et al., "Bench-Top Fermentative Production of Plant Benzylisoquinoline Alkaloids Using a Bacterial Platform", Bioeng. Bugs (2012), 3:49-53.
Onoyovwe et al., "Morphine Biosynthesis in Opium Poppy Involves Two Cell Types: Sieve Elements and Laticifers", Plant Cell (2013), 25(10): 4110-4122.
Ounaroon et al., "(R,S)-Reticuline 7-O-Methyltransferase and (R,S)-Norcoclaurine 6-O-Methyltransferase of Papaver somniferum—cDNA Cloning and Characterization of Methyl Transfer Enzymes of Alkaloid Biosynthesis in Opium Poppy", Plant J. (2003), 36:808-819.
Sandig et al., "Regulation of Endoplasmic Reticulum Biogenesis in Response to Cytochrome P450 Overproduction", Drug Metab. Rev. (1999), 31:393-410.
Sato et al., "Purification and Characterization of S-adenosyl-L-methionine: norcoclaurine 6-O-methyltransferase from Cultured Coptis japonica Cells", Eur. J. Biochem. (1994), 225:125-131.
Siddiqui et al., "Advancing Secondary Metabolite Biosynthesis in Yeast with Synthetic Biology Tools", FEMS Yeast Res. (2012), 12:144-170.
Takemura et al., "Molecular Cloning and Characterization of a Cytochrome P450 in Sanguinarine Biosynthesis from Eschscholzia californica Cells", Phytochemistry (2013), 91:100-108.
Unterlinner et al., "Molecular Cloning and Functional Expression of Codeinone Reductase: the Penultimate Enzyme in Morphine Biosynthesis in the Opium Poppy Papaver somniferum", Plant J. (1999), 18:465-475.
Wijekoon et al., "Systematic Knockdown of Morphine Pathway Enzymes in Opium Poppy Using Virus-Induced Gene Silencing", Plant J. (2012), 69:1052-1063.
Zhang et al., "14-Hydroxylation of Opiates: Catalytic Direct Autoxidation of Codeinone to 14-Hydroxycodeinone", J. Am. Chem. Soc. (2005), 127:7286-7287.
Ziegler et al., "Removal of Substrate Inhibition and Increase in Maximal Velocity in the Short Chain Dehydrogenase/Reductase Salutaridine Reductase Involved in Morphine Biosynthesis", J. Biol. Chem. (2009), 284:26758-26767.
Zimmer et al., "Protein Quality—a Determinant of the Intracellular Fate of Membrane-Bound Cytochromes P450 in Yeast", DNA Cell Biol. (1997), 16:501-514.
Kutchan, Tony M. "Heterologous expression of alkaloid biosynthetic genes—a review", Gene, vol. 179, No. 1, Nov. 7, 1996, pp. 73-81.
Notice of Allowance dated Apr. 25, 2016 for U.S. Appl. No. 14/961,662, 7 pages.
Branden et al. Introduction to Protein Structure, Garland Publishing Inc., New York, p. 247 (1991).
Cooper et al., "On the amine oxidases of Klebsiella aerogenes strain W70," FEMS Microbiol. Lett., 146(1):85-89 (1997).
Facchini et al., "Differential and Tissue-Specific Expression of a Gene Family for Tyrosine/Dopa Decarboxylase in Opium Poppy," J. Biol. Chem., 269(43):26684-26690 (1994).
Hiroi et al., "Dopamine Formation from Tyramine by CYP2D6," Biochemical & Biophysical Research communications, 249:838-843 (1998).
Iraqui et al., "Characterisation of *Saccharomyces cerevisiae* AR08 and AR09 genes encoding aromatic aminotransferases I and II reveals a new aminotransferase subfamily," Mol. Gen. Genet., 257(2):238-248 (1998).
Kutchan et al., "Molecular Genetics of Plant Alkaloid Biosynthesis," ALKALOIDS, 50:257-316 (1998).
Moerner et al., "Illuminating single molecules in condensed matter," Science, 283(5408):1670-1676 (1999).
Samanani et al., "Molecular cloning and characterization of norcoclaurine synthase, an enzyme catalyzing the first committed step in benzylisoquinoline alkaloid biosynthesis," Plant J., 40(2):302-313 (2004).
Stewart et al., "A Chemist's Perspective on the Use of Genetically Engineered Microbes as Reagents for Organic Synthesis," Biotechnology and Genetic Engineering Reviews, 14:67-143 (1997).

(56) References Cited

OTHER PUBLICATIONS

Vuralhan et al., "Identification and characterization of phenylpyruvate decarboxylase genes in *Saccharomyces aerevisiae*," Appl. Environ. Microbial., 69(8):4534-4541 (2003).
Zenk et al., "Benzylisoquinoline Biosynthesis by Cultivated Plant Cells and Isolated Enzymes," Journal of Natural Products, 48(5):725-738 (1985).
Single Molecule Detection and Manipulation Workshop. Apr. 17-18, 2000, 28 pages. Retrieved from http://www.nigms.nih.gov/news/reports/single_molecules.html.
Office Action dated Nov. 6, 2015 for U.S. Appl. No. 14/614,484, 26 pages.
Notice of Allowance dated Mar. 8, 2016 for U.S. Appl. No. 14/614,484, 10 pages.

\* cited by examiner

Unidirectional:

Adjacent (oppositely oriented):

```
                            SEQUENCE LISTING

<160> NUMBER OF SEQ ID NOS: 11

<210> SEQ ID NO 1
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 1

Ser Thr Ser Glu Asn Gln Ser Lys Gly Ser Gly Thr Leu Val Val Ile
1               5                   10                  15

Leu Ala Ile Leu Met Leu Gly Val Ala Tyr Tyr Leu Leu Asn Glu
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 2

Ile Leu Glu Gln Pro Leu Lys Phe Val Leu Thr Ala Ala Val Val Leu
1               5                   10                  15

Leu Thr Thr Ser Val Leu Cys Cys Val Val Phe Thr
            20                  25

<210> SEQ ID NO 3
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 3

Met Phe Phe Asn Arg Leu Ser Ala Gly Lys Leu Leu Val Pro Leu Ser
1               5                   10                  15

Val Val Leu Tyr Ala Leu Phe Val Val Ile Leu Pro Leu Gln Asn Ser
            20                  25                  30

Phe His Ser Ser Asn Val Leu Val Arg Gly
        35                  40

<210> SEQ ID NO 4
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 4

His Asp Glu Leu
1

<210> SEQ ID NO 5
<211> LENGTH: 35
<212> TYPE: PRT
<213> ORGANISM: Artificial Sequence
<220> FEATURE:
<223> OTHER INFORMATION: Synthetic polypeptide
```

```
<400> SEQUENCE: 5

Asn Ile Lys Glu Ile Met Trp Trp Gln Lys Val Lys Asn Ile Thr Leu
  1               5                  10                  15

Leu Thr Phe Thr Ile Ile Leu Phe Val Ser Ala Ala Phe Met Phe Phe
             20                  25                  30

Tyr Leu Trp
         35

<210> SEQ ID NO 6
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 6

Trp Tyr Lys Asp Leu Lys Met Cys Leu Ala Leu Val Ile Ile Ile Leu
  1               5                  10                  15

Leu Val Val Ile Ile Val Pro Ile Ala Val His Phe Ser Arg
             20                  25                  30

<210> SEQ ID NO 7
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 7

Met Leu Ser Leu Arg Gln Ser Ile Arg Phe Phe Lys Pro Ala Thr Arg
  1               5                  10                  15

Thr Leu Cys Ser Ser Arg
             20

<210> SEQ ID NO 8
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 8

Gly Gly Gly Gly Gly Gly Ser Thr
  1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 9

Pro Gly Gly Gly Gly Gly Gly
  1               5

<210> SEQ ID NO 10
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 10
```

```
Leu Lys Gly Val Val Val Ala Gly Gly Val Leu Ala Gly Ala Val Ala
 1               5                  10                  15

Val Ala Ser Phe Phe Leu Arg Asn Lys Arg Arg
            20                  25

<210> SEQ ID NO 11
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 11

Met Lys Ala Phe Thr Ser Leu Leu Cys Gly Leu Gly Leu Ser Thr Thr
 1               5                  10                  15

Leu Ala Lys Ala Ile Ser Leu Gln Arg Pro Leu Gly Leu Asp Lys Asp
            20                  25                  30

Val Leu Leu Gln Ala Ala Glu Lys Phe Gly Leu Asp Leu Asp Leu Asp
        35                  40                  45

His Leu
    50
```

BENZYLISOQUINOLINE ALKALOIDS (BIA) PRODUCING MICROBES, AND METHODS OF MAKING AND USING THE SAME

CROSS-REFERENCE TO RELATED APPLICATIONS

Pursuant to 35 U.S.C. §119 (e), this application claims priority to the filing date of U.S. Provisional Patent Application Ser. No. 61/788,560 filed on Mar. 15, 2013; the disclosure of which application is herein incorporated by reference.

GOVERNMENT RIGHTS

This invention was made with Government support under contract no. 1066100 awarded by the National Science Foundation and under contract no. AT007886 awarded by the National Institutes of Health. The Government has certain rights in the invention.

INTRODUCTION

Benzylisoquinoline alkaloids (BIAs) are a large group of secondary metabolites from plants and other organisms. These molecules have therapeutic functions in the human body, ranging from the established analgesic and antitussive properties of morphine and codeine, to novel activities against cancer and infection observed for molecules such as berberine and sanguinarine. Supply of all these BIA molecules so that they are available to researchers and physicians is of interest. The number of synthetic reactions and requirements for selective stereochemistry means that chemical synthesis of BIAs is low yielding and not a viable means for large-scale production. Instead, for the widely used drugs codeine and morphine, the opium poppy (*Papaver somniferum*) has been bred and developed as a production crop. Intermediates in morphine biosynthesis that find use as drugs and drug precursors do not accumulate because the plant metabolism is evolved to maximize pathway flux to the final opioids. Even for end product metabolites like morphine, accumulation occurs only within specialized cells in the buds and vascular tissue and requires harsh chemical processing of harvested plant material during the extraction process, which typically yields less than 2% morphine by dry weight.

SUMMARY

Aspects of the invention include host cells that are engineered to produce benzylisoquinoline alkaloids (BIAs). The host cells include heterologous coding sequences for a variety of enzymes involved in synthetic pathways from starting compounds to BIAs of the host cell. The heterologous coding sequences may be derived from a different source organism as compared to the host cell and multiple copies of the heterologous coding sequences may be present in the host cells. In some embodiments, the host cell is selected from a reticuline-producing host cell, a sanguinarine precursor-producing host cell, a protoberberine-producing host cell, a thebaine-producing host cell and an opiate-producing host cell. Also provided are methods of producing the BIAs of interest by culturing the host cells under culture conditions that promote activity of enzymes encoded by the heterologous coding sequences of the host cells. Aspects of the invention further include compositions, e.g., host cells, starting compounds and kits, etc., that find use in methods of the invention.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
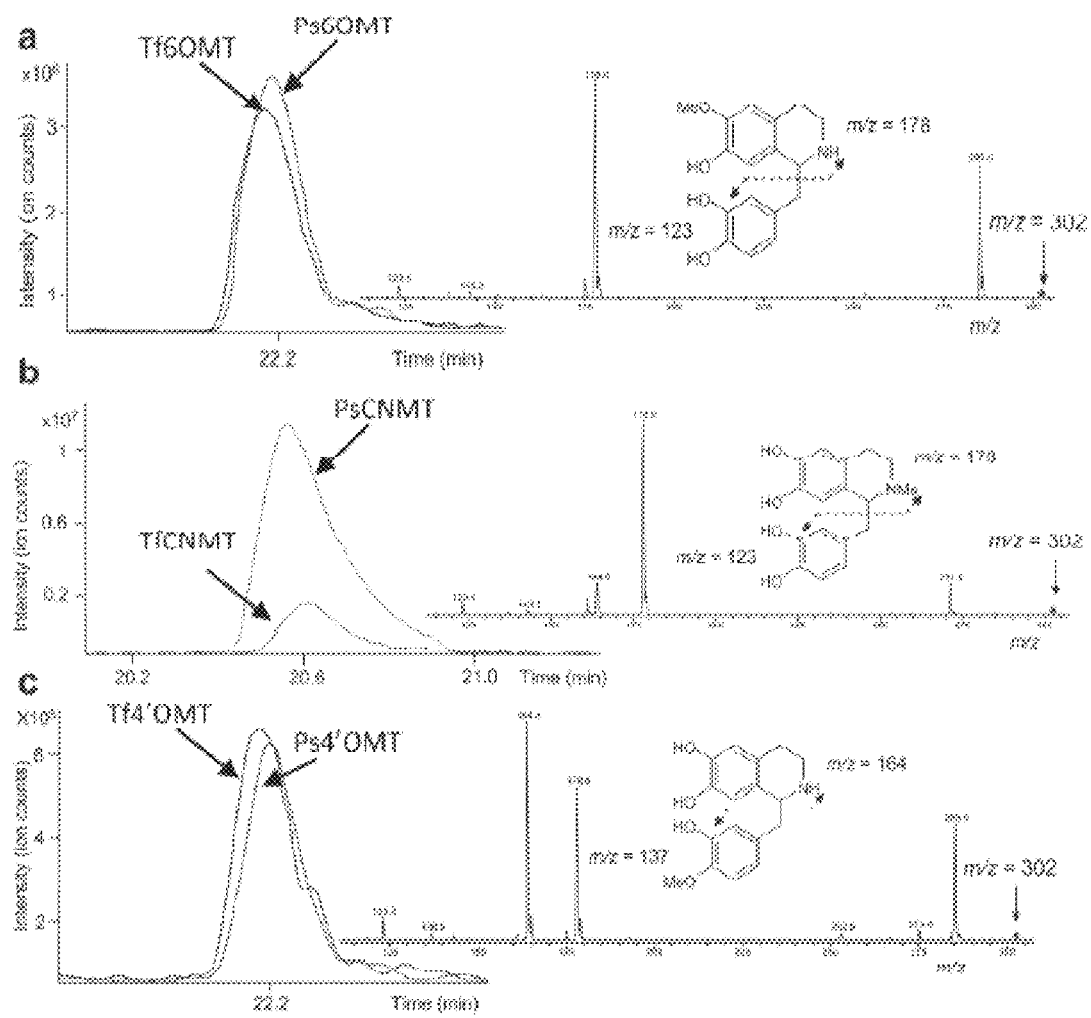
FIG. 1 depicts the in vivo methylation of norlaudanosoline by methyltransferases from *P. somniferum* and *Thalictrum flavum* with detection of methylation products by liquid chromatography-mass spectrometry (LCMS).

As summarized above, aspects of the invention include host cells that are engineered to produce benzylisoquinoline alkaloids (BIAs). The host cells include heterologous coding sequences for a variety of enzymes involved in synthetic pathways from starting compounds to BIAs of the host cell. In some embodiments, the host cell is selected from a reticuline-producing host cell, a sanguinarine precursor-producing host cell, a protoberberine-producing host cell, a thebaine-producing host cell and an opiate-producing host cell. Also provided are methods of producing the BIAs of interest by culturing the host cells under culture conditions that promote expression of enzymes encoded by the heterologous coding sequences of the host cells.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Benzylisoquinoline Alkaloids (BIAs)

Aspects of the present invention include host cells which produce compounds that are characterized as benzylisoquinoline alkaloids (BIAs), as well as biosynthetic precursors, intermediates, and metabolites thereof. A variety of BIAs, biosynthetic precursors, intermediates, and metabolites thereof may be produced by the subject host cells, including but not limited to reticuline, sanguinarine, a protoberberine, berberine, a benzophenanthridine alkaloid, thebaine, an opiate compound, cheilanthifoline, stylopine, cis-N-methylstylopine, salutaridinol, salutaridinol-7-O-acetate, protopine and dihydrosanguinarine, (S)-canadine, oripavine, codeinone, neopine, neomorphine, morphine, codeine, hydromorphone, hydrocodone, oxycodone, oxymorphone, dihydrocodeine, 14-hydroxycodeine and dihydromorphine.

The synthetic pathways generated in the host cells may start with any convenient compound(s). Starting compounds of interest include, but are not limited to, laudanosoline, methyl laudanosoline, norlaudanosoline, methyl norlaudanosoline, norcoclaurine, salutaridine, reticuline, tyramine, dopamine, 4-HPA, 4-HPPA, coclaurine, N-methylcoclaurine, 3'-hydroxy-N-methylcoclaurine, scoulerine, tetrahydrocolumbamine, canadine, laudanine, sanguinarine, thebaine, morphine, codeine, codeinone and dimethyl tetrahydroisoquinoline, e.g., 6,7-dimethyl-1-2-3-4-tetrahydroisoquinoline or another compound that may or may not be normally present in the endogenous BIA pathway. In certain embodiments, the starting compound is reticuline, norlaudanosoline or norcoclaurine. Thus, the starting material may be non-naturally occurring or the starting material may be naturally occurring. Other compounds may also be used as the starting material in the desired synthetic pathway, based upon the synthetic pathway present in the host cell. The source of the starting material may be from the host cell itself, e.g., tyrosine, or the starting material may be added or supplemented to the host cell from an outside source. For example, if the host cells are growing in liquid culture (an in vivo environment), the cell media may be supplemented with the starting material, e.g., tyrosine or norlaudanosoline, which is transported into the cells and converted into the desired products.

Host Cells

As summarized above, one aspect of the invention is a host cell that produces one or more BIAs. Any convenient type of host cell may be utilized in producing the subject BIA-producing cells, see, e.g., US2008/0176754, the disclosure of which is incorporated by reference in its entirety. In some cases, the host cell is yeast. In some instances the host cell is from a strain of yeast engineered to produce a BIA of interest. In some embodiments, the host cell is selected from a reticuline-producing host cell, a sanguinarine precursor-producing host cell, a protoberberine-producing host cell, a thebaine-producing host cell and an opiate-producing host cell.

Any convenient cells may be utilized in the subject host cells and methods. In some cases, the host cells are non-plant cells. In certain cases, the host cells are insect cells, mammalian cells, bacterial cells or yeast cells. Host cells of interest include, but are not limited to, bacterial cells, such as *Bacillus subtilis, Escherichia coli, Streptomyces* and *Salmonella typhimuium* cells and insect cells such as *Drosophila melanogaster* S2 and *Spodoptera frugiperda* Sf9 cells. In some embodiments, the host cells are yeast cells or *E. coli* cells. In certain embodiments, the yeast cells can be of the species *Saccharomyces cerevisiae* (*S. cerevisiae*). Yeast is of interest as a host cell because cytochrome P450 proteins, which are involved in some biosynthetic pathways of interest, are able to fold properly into the endoplasmic reticulum membrane so that their activity is maintained. Yeast strains of interest that find use in the invention include, but are not limited to, those described by Smolke, et al., in US2008/0176754, the disclosure of which is incorporated by reference in its entirety, such as CEN.PK (Genotype: MA Ta/α ura3-52/ura3-52 trp1-289/trp1-289 leu2-3_112/leu2-3_112 his3 Δ1/his3 Δ1 MAL2-8C/MAL2-8C SUC2/SUC2), S288C, W303, D273-10B, X2180, A364A, Σ1278B, AB972, SK1 and FL100. In certain cases, the yeast strain is any of S288C (MATα; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3Δ0), BY4743 (MATa/MATα; his3Δ1/his3Δ1; leu2Δ0/leu2Δ0; met15Δ0/MET15; LYS2/lys2Δ0; ura3Δ0/ura3Δ0), and WAT11 or W(R), derivatives of the W303-B strain (MATa; ade2-1; his3-11, -15; leu2-3, -112; ura3-1; canR; cyr+) which express the *Arabidopsis thaliana* NADPH-P450 reductase ATR1 and the yeast NADPH-P450 reductase CPR1, respectively. In another embodiment, the yeast cell is W303alpha (MATα; his3-11, 15 trp1-1 leu2-3 ura3-1 ade2-1). The identity and genotype of additional yeast strains of interest can be found at EUROSCARF (web.uni-frankfurt.de/fb15/mikro/euroscarf/col_index.html).

The term "host cells," as used herein, are cells that harbor one or more heterologous coding sequences which encode activity(ies) that enable the host cells to produce desired BIA(s), e.g., as described herein. The heterologous coding sequences could be integrated stably into the genome of the host cells, or the heterologous coding sequences can be transiently inserted into the host cell. As used herein, the term "heterologous coding sequence" is used to indicate any polynucleotide that codes for, or ultimately codes for, a peptide or protein or its equivalent amino acid sequence, e.g., an enzyme, that is not normally present in the host organism and can be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences can be RNA or any type thereof, e.g., mRNA, DNA or any type thereof, e.g., cDNA, or a hybrid of RNA/DNA. Examples of coding sequences include, but are not limited to, full-length transcription units that comprise such features as the coding sequence, introns, promoter regions, 3'-UTRs and enhancer regions.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene comprising introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences can have a deletion of one or more amino acids, with the deletion being N-terminal, C-terminal or internal. Truncated forms are envisioned as long as they have the catalytic capability indicated herein. Fusions of two or more enzymes are also envisioned to facilitate the transfer of metabolites in the pathway, provided that catalytic activities are maintained.

Operable fragments, mutants or truncated forms may be identified by modeling and/or screening. This is made possible by deletion of, for example, N-terminal, C-terminal or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

Aspects of the present invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of a decarboxylase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc. In certain embodiments, an "equivalent" amino acid sequence contains at least 80%-99% identity at the amino acid level to the specific amino acid sequence, in some cases at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

The host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product. In some cases, if the host cell is a yeast cell and the desired pathway requires the cosubstrate 2-oxoglutarate, the expression of the native endogenous glutamate and/or 2-oxoglutarate dehydrogenase enzymes may be may be reduced or ablated, which could convert the desired cosubstrate (2-oxoglutarate) into glutamate or succinyl-CoA, respectively. In some instances, where ablation of expression of a protein may be of interest, is in proteins involved in the pleiotropic drug response, including, but not limited to, ATP-binding cassette (ABC) transporters, multidrug resistance (MDR) pumps and associated transcription factors, These proteins are involved in the export of BIA molecules into the culture medium, thus deletion controls the export of the compounds into the media, making them more available for incorporation into the desired product. In some embodiments, host cell gene deletions of interest include genes associated with the unfolded protein response and endoplasmic reticulum (ER) proliferation. Such gene deletions may lead to improved BIA production. The expression of cytochrome P450s may induce the unfolded protein response and may cause the ER to proliferate. Deletion of genes associated with these stress responses may control or reduce overall burden on the host cell and improve pathway performance. Genetic alterations may also include modifying the promoters of endogenous genes to increase expression and/or introducing additional copies of endogenous genes. Examples of this include the construction/use of strains which overexpress the endogenous yeast NADPH-P450 reductase CPR1 to increase activity of heterologous P450 enzymes. In addition, endogenous enzymes such as ARO8, 9, and 10, which are directly involved in the synthesis of intermediate metabolites, may also be overexpressed.

Heterologous coding sequences of interest include but are not limited to sequences that encode enzymes, either wild-type or equivalent sequences, that are normally responsible for the production of BIAs in plants. In some cases, the enzymes for which the heterologous sequences code can be any of the enzymes in the BIA pathway, and can be from any convenient source. In some instances, cheilanthifoline synthase (CFS; EC 1.14. 21.2) is found in at least *Papaver somniferum, Eschscholzia californica*, and *Argemone mexicana* and is known to synthesize (S)-cheilanthifoline from (S)-scoulerine. The choice and number of enzymes encoded by the heterologous coding sequences for the particular synthetic pathway may be selected based upon the desired product. In certain embodiments, the host cells of the present invention may comprise 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14 or 15 heterologous coding sequences.

Unless otherwise noted, the heterologous coding sequences are as reported in GENBANK. A list of enzymes of interest is shown in Tables 2 and 3. The host cells of the present invention may comprise any combination of the listed enzymes, from any source. Unless otherwise indicated, Accession numbers in Table 3 refer to GenBank. Some accession numbers refer to the *Saccharomyces* genome database (SGD) which is available on the world-wide web at www.yeastgenome.org.

In some embodiments, the host cell (e.g., a yeast strain) is engineered for selective production of a BIA of interest by localizing one or more enzymes to a compartment in the cell. In one embodiment of the invention illustrated in FIG. 18, an enzyme may be localized to the yeast endoplasmic reticulum by fusing an ER2 targeting sequence to the C-terminus of the protein.

In some cases, an enzyme may be located in the host cell such that the compound produced by this enzyme spontaneously rearranges, or is converted by another enzyme to a desirable metabolite before reaching a localized enzyme that may convert the compound into an undesirable metabolite. The spatial distance between two enzymes may be selected to prevent one of the enzymes from acting directly on a compound to make an undesirable metabolite, and restrict production of undesirable end products (e.g., an undesirable opioid by-product). In certain embodiments, any of the enzymes described herein, either singularly or together with a second enzyme, may be localized to any convenient compartment in the host cell, including but not limited to, an organelle, endoplasmic reticulum, golgi, vacuole, nucleus, plasma membrane or the periplasm (see, e.g., FIG. 18).

In some embodiments, the host cell includes one or more of the enzymes that comprise a localization tag. Any convenient tags may be utilized. In some cases, the localization tag is a peptidic sequence that is attached at the N-terminal and or C-terminal of the enzyme. Any convenient methods may be utilized for attaching a tag to the enzyme.

In some cases, the localization tag is derived from an endogenous yeast protein. Such tags may provide route to a variety of yeast organelles: the endoplasmic reticulum (ER), mitochondria (MT), plasma membrane (PM), and vacuole (V).

In certain embodiments, the tag is an ER routing tag (e.g., ER1). In certain embodiments, the tag is a vacuole tag (e.g., V1). In certain embodiments, the tag is a plasma membrane tag (e.g., P1). In certain instances, the tag includes or is derived from, a transmembrane domain from within the tail-anchored class of proteins.

In some embodiments, the localization tag locates the enzyme on the outside of an organelle. In certain embodiments, the localization tag locates the enzyme on the inside of an organelle.

In some instances, the expression of each type of enzyme is increased through additional gene copies (i.e., multiple copies), which increases intermediate accumulation and ultimately BIA and/or BIA precursor production. Embodiments of the present invention include increased BIA production in a host cell through simultaneous expression of multiple species variants of a single or multiple enzymes. In some cases, additional gene copies of a single or multiple enzymes are included in the host cell. Any convenient methods may be utilized in including multiple copies of a heterologous coding sequence for an enzyme in the host cell.

In some embodiments, the host cell includes multiple copies of a heterologous coding sequence for an enzyme, such as 2 or more, 3 or more, 4 or more, 5 or more, or even 10 or more copies. In certain embodiments, the host cell include multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

The engineered host cell medium may be sampled and monitored for the production of BIA compounds of interest. The BIA compounds may be observed and measured using any convenient methods. Methods of interest include, but are not limited to, LC-MS methods (e.g., as described herein) where a sample of interest is analyzed by comparison with a known amount of a standard compound. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Reticuline-producing Host Cells

Reticuline is the major branch point intermediate in the synthesis of BIAs and a high yield of this intermediate is of interest in engineering efforts to produce end products such as morphine, sanguinarine or berberine. In some cases, to produce reticuline from norlaudanosoline three enzymes are expressed in the host cell: norcoclaurine 6-O-methyltransferase (6OMT; EC 2.1.1.128), coclaurine N-methyltransferase (CNMT; EC 2.1.1.140) and 3'hydroxy-N-methylcoclaurine 4'-O-methylase (4'OMT; EC 2.1.1.116). In general, the enzymes are derived from different source organisms as compared to the host cell. To produce reticuline from norcoclaurine, an additional cytochrome P450 enzyme, e.g., CYP80B3 or CYP80B1 (EC 1.14.13.71), may be expressed with the three methyltransferases. Engineering *S. cerevisiae* to produce reticuline may utilize any convenient optimization methods. In some instances, all combinations of the three methyltransferases from two or more species (e.g., *P. somniferum* and *T. flavum*) are expressed together to find the best reticuline producer. In another instance, the optimal combination of methyltransferases (all 3 from *P. somniferum*) may be integrated into the yeast chromosome and the expression of each titrated without effecting yield of reticuline. The expression of the methyltransferase enzymes may be titrated up or down, and the methyltransferases may act sequentially, in concert or a combination of the two, on the substrates.

Aspects of the invention include strains of *S. cerevisiae* with improved reticuline production through overexpression of 6OMT, CNMT and/or 4'OMT genes from several different species. By improved or increased production is meant both the production of some amount of reticuline where the control has no reticuline production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some reticuline production. Methyltransferases from different species have slightly different substrate specificities [Choi et al. (2002). *J Biol Chem* 277, 830-835; Liscombe et al. (2009). *Plant J* 60, 729-74; Morishige et al., (2000) *J Biol Chem* 275, 23398-23405; Ounaroon et al. (2003) *Plant J* 36, 808-819; Sato et al., (1994) *Eur J Biochem* 225, 125-131]. When methyltransferases of different species origin are expressed together in a single strain, it is possible to take advantage of the varying substrate specificities and increase flux through the multiple methylation pathways to increase the yield of reticuline. In some cases, species variants of the methyltransferases include, but are not limited to, *P. somniferum, T. flavum* and *Coptis japonica* (Table 2). In certain cases, species variants of the methyltransferases are derived from *P. somniferum*. In certain instances, species variants of the methyltransferases are derived from *T. flavum*. In some embodiments, species variants of the methyltransferases are derived from *C. japonica*.

In some embodiments, the host cell comprises two or more heterologous coding sequences for two or more methyltransferases selected from 6OMT, CNMT and 4'OMT. In certain instances, the two or more methyltransferases are derived from two or more different source organisms as compared to the host cell.

In some cases, the host cell comprises heterologous coding sequences for the methyltransferases 6OMT and CNMT. In certain cases, the host cell comprises heterologous coding sequences for the methyltransferases CNMT and 4'OMT.

In some instances, the host cell comprises heterologous coding sequences for the methyltransferases 6OMT and 4'OMT.

In certain embodiments, the host cell comprises heterologous coding sequences for all of the methyltransferases 6OMT, CNMT and 4'OMT.

In some instances, the expression of each type of methyltransferase is increased through additional gene copies (i.e., multiple copies), which increases intermediate accumulation and ultimately reticuline production. Embodiments of the present invention include increased reticuline production in a yeast strain through simultaneous expression of multiple species variants of a single or multiple methyltransferases and incorporation of additional gene copies of a single or multiple methyltransferases.

In some embodiments, the host cell include multiple copies of a methyltransferase, such as 2 or more, 3 or more, 4 or more, 5 or more, or even 10 or more copies. In certain embodiments, the host cell include multiple copies of one or more methyltransferases, such as multiple copies of two or more, three or more, four or more, etc. methyltransferases. In some cases, the multiple copies of the methyltransferase are derived from two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In some instances, the multiple copies are of a heterologous coding sequence for CNMT. In certain instances, two copies of a heterologous coding sequence for CNMT are included. In some instances, the multiple copies are of a heterologous coding sequence for 6OMT. In certain instances, two copies of a heterologous coding sequence for 6OMT are included. In some instances, the multiple copies are of a heterologous coding sequence for 4'OMT. In certain instances, two copies of a heterologous coding sequence for 4'OMT are included.

In some cases, the host cell is capable of producing an increased amount of reticuline from norcoclaurine relative to a control host cell that lacks multiple copies of the one or more heterologous coding sequences for the one or more methyltransferase. In certain instances, the increased amount of reticuline is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of reticuline from norlaudonosoline relative to a control host cell that lacks multiple copies of the one or more heterologous coding sequences for the one or more methyltransferase. In certain instances, the increased amount of reticuline is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some embodiments, the host cell is capable of producing a 10% or more yield of reticuline from norcoclaurine, such as 20% or more, 30% or more, 40% or more, 50% or more, 60% or more, 70% or more, 80% or more, or even 90% or more yield of reticuline from norcoclaurine.

In some embodiments, the host cell is capable of producing a 10% or more yield of reticuline from norlaudonosoline, such as 20% or more, 30% or more, 40% or more, 50% or more, 60% or more, 70% or more, 80% or more, or even 90% or more yield of reticuline from norlaudonosoline.

In certain embodiments, the host cell is an engineered strain that includes a biosynthetic pathway that incorporates any combination of the following alternative methylation routes and leads to increased production of reticuline. In some instances, the host cell is capable of producing reticuline from norlaudanosoline via a biosynthetic pathway of FIG. 2. In certain embodiments, the host cell is capable of producing reticuline from norcoclaurine via a biosynthetic pathway of FIG. 3. In some cases, when the starting material of the pathway is norlaudanosoline (FIG. 2, (1)), 6OMT, CNMT and/or 4'OMT may act on this compound to produce three distinctly methylated intermediates: BIA 2, which is initially methylated by 6OMT, is then methylated by either CNMT or 4'OMT; BIA 3, which is initially methylated by CNMT, is then methylated by either 6OMT or 4'OMT; BIA 4, which is initially methylated by 4'OMT, is then methylated by either 6OMT or CNMT; BIA 5, which is previously methylated by 6OMT and 4'OMT, is methylated by CNMT to produce reticuline; BIA 6, which is previously methylated by 6OMT and CNMT, is methylated by 4'OMT to produce reticuline; and BIA 7, which is previously methylated by CNMT and 4'OMT, is methylated by 6OMT to produce reticuline.

In some instances, when the starting material of the pathway is norcoclaurine, 6OMT or CNMT may act on this compound, to produce two distinctly methylated products (FIG. 3): BIA 10, which is initially methylated by 6OMT, is then methylated by CNMT; BIA 11, which is initially methylated by CNMT, is then methylated by 6OMT. BIA 12, also known as N-methylcoclaurine, which is previously methylated by 6OMT and CNMT, is then sequentially acted upon by CYP80B1 or CYP80B3 and 4'OMT to produce reticuline.

In certain instances, the host cell is a yeast strain. In some cases, the yeast strain is *S. cerevisiae*.

Sanguinarine and Sanguinarine Precursor-producing Host Cells

Figure 4:
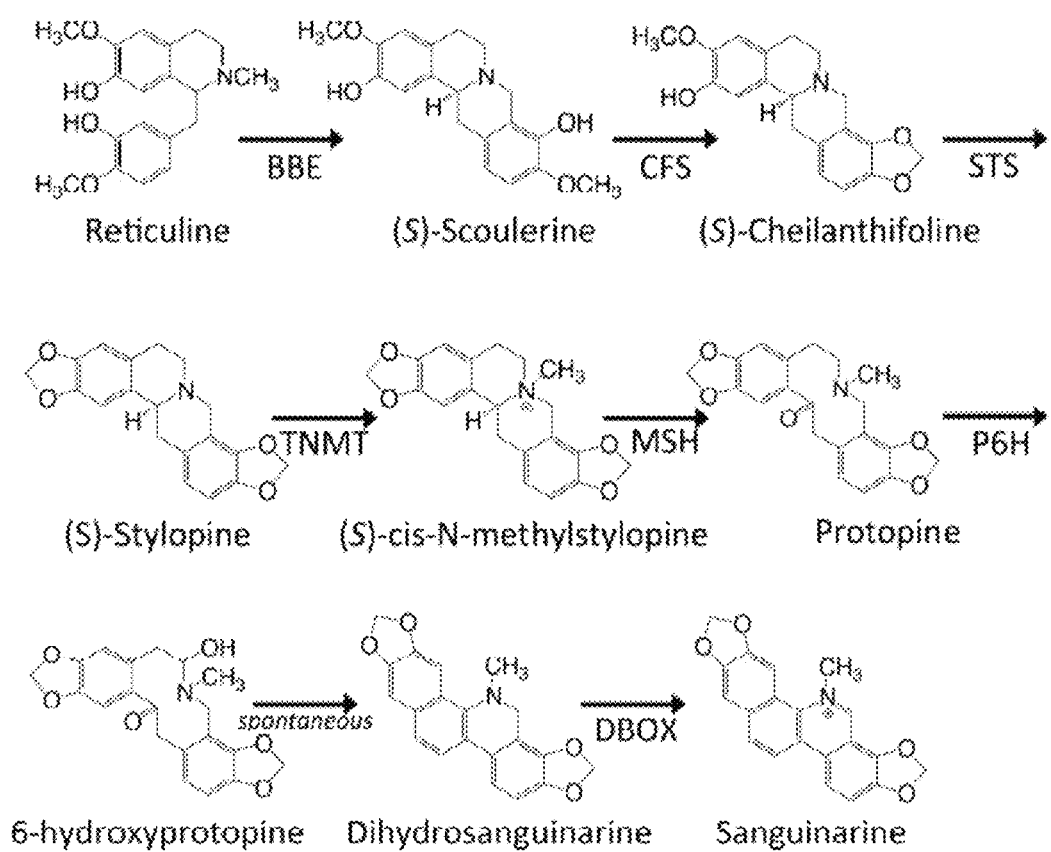
FIG. 4 depicts the biosynthetic steps to produce sanguinarine from reticuline.

Aspects of the invention include host cells that produce protoberberine and benzophenanthridine alkaloids, including, but not limited to, cheilanthifoline, stylopine, cis-N-methylstylopine, scoulerine, protopine, dihydrosanguinarine and sanguinarine. FIG. 4 depicts a synthetic pathway present in embodiments of host cells according to embodiments of the present invention. Although the pathway may be longer, starting from norlaudanosoline, norcoclaurine or any other convenient BIAs, e.g., as shown in other figures, this particular pathway depiction begins with reticuline and ends with sanguinarine. The pathway can include fewer enzymes than those displayed if the desired end result is one of the intermediates in the norlaudanosoline to sanguinarine pathway. The present invention includes biosynthetic pathways of multiple enzymatic steps, e.g., those catalyzed by the enzymes BBE (EC 1.21.3.3), CFS (EC 1.14.21.2), CPR (EC 1.6.2.4), STS (EC 1.14.21.1), TNMT (EC 2.1.1.122), MSH (EC 1.14.13.37), P6H (EC 1.14.13.55) and DBOX (EC 1.5.3.12), within an engineered yeast strain to produce a variety of protoberberine and benzophenanthridine compounds. In addition, the present invention includes tools and methods to optimize the production of protoberberine and benzophenanthridine compounds within the context of the engineered yeast strain.

In some embodiments, the host cell is capable of producing sanguinarine or a sanguinarine precursor, wherein the host cell comprises one or more heterologous coding sequences for one or more enzymes selected from BBE, CFS, CPR, STS, TNMT, MSH, P6H and DBOX, wherein the one or more enzymes is derived from a different source organism as compared to the host cell. In certain embodiments, the sanguinarine precursor is a protoberberine or a benzophenanthridine alkaloid.

In certain instances, the source organism is *P. somniferum, E. californica, Arabidopsis thaliana, Papaver bracteatum* or *A. mexicana*. In certain cases, the source organism is *P. somniferum*. In some instances, the source organism is *E. californica*. In some instances, the source organism is *A. thaliana*. In certain embodiments, the source organism is *P. bracteatum*. In some cases, the source organism is *A. mexicana*.

In some instances, the one or more enzymes is two or more enzymes that are derived from two or more different source organisms as compared to the host cell.

In some embodiments, the host cell comprises multiple copies of the one or more heterologous coding sequences. In certain embodiments, the multiple copies of the one or more heterologous coding sequences are derived from two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In some cases, the host cell comprises two or more, such as three or more, four or more, five or more, or even more, heterologous coding sequences for two or more enzymes selected from BBE, CFS, CPR, STS, TNMT, MSH, P6H and DBOX.

In certain instances, the host cell further comprises one or more gene deletions in comparison to a native host cell, wherein the one or more deleted genes is selected from IRE1, HAC1, OPI1, INO1, INO2, INO3, PDR1, STB5, PDR3, PDR5, SNQ2, YOR1, TPO1, TPO2, TPO3, TPO4, PDR10, PDR11, PDR15, PDR16, PDR17, QDR1, QDR2, QDR3, FLR1, AQR1, AQR2, and CIN5.

In some cases, the host cell is a yeast strain (e.g., as described herein).

In certain embodiments, the host cell is capable of producing the sanguinarine or sanguinarine precursor from norlaudanosoline via a biosynthetic pathway of FIG. 4. In some instances, the host cell is capable of producing the sanguinarine or sanguinarine precursor from norlaudanosoline via a biosynthetic pathway of FIG. 11.

In some instances, the host cell comprises a heterologous coding sequence for a BBE enzyme. The heterologous coding sequence for the BBE enzyme may be integrated into a host cell chromosome. In some instances, the host cell comprises a heterologous coding sequence for a CFS enzyme. In some instances, the host cell comprises a heterologous coding sequence for a CPR enzyme. In some instances, the host cell comprises a heterologous coding sequence for a STS enzyme. In some instances, the host cell comprises a heterologous coding sequence for a TNMT enzyme. In some instances, the host cell comprises a heterologous coding sequence for a MSH enzyme. In some instances, the host cell comprises a heterologous coding sequence for a P6H enzyme. In some instances, the host cell comprises a heterologous coding sequence for a DBOX enzyme.

In some cases, the host cell is a yeast strain that produces scoulerine, where berberine bridge enzyme (BBE; EC 1.21.3.3) (e.g., from *P. somniferum* or *E. californica*) is expressed on a low copy construct (e.g., a low copy plasmid, YAC or chromosomally integrated) in the yeast strain with, e.g., Ps6OMT, PsCNMT, and/or Ps4'OMT chromosomally integrated. Any convenient variants of the enzymes may be utilized, e.g., one of more of the enzyme variants depicted in Table 2.

In some cases, the sanguinarine precursor is cheilanthifoline. In certain instances, the host cell comprises heterologous coding sequences for cheilanthifoline synthase (CFS; EC 1.14.21.2) and a cytochrome P450 NADPH reductase (CPR; EC 1.6.2.4) enzyme. In some instances, the CPR enzyme is an ATR enzyme, e.g., ATR1. In some instances, the host cell is a yeast strain that produces cheilanthifoline, where cheilanthifoline synthase (CFS) (e.g., from *E. californica* (EcCFS), *P. somniferum* (PsCFS) and/or *A. mexicana* (AmCFS)) is expressed on a low copy construct (e.g., a low copy plasmid, YAC or chromosomally integrated) in the yeast strain with, e.g., Ps6OMT, PsCNMT, Ps4'OMT, PsBBE and/or ATR1 chromosomally integrated. Any convenient variants of the enzymes may be utilized, e.g., one of more of the enzyme variants depicted in Table 2.

In some embodiments, the host cell produces stylopine, where stylopine synthase (STS; EC 1.14.21.1) (e.g., from *E. californica* (EcSTS), *P. somniferum* (PsSTS) and/or *A. mexicana* (AmSTS)) is expressed in the host cell on a low copy construct (e.g., a low copy plasmid, YAC or chromosomally integrated) in a cheilanthifoline producing strain. Any convenient variants of the enzymes may be utilized, e.g., one of more of the enzyme variants depicted in Table 2.

In certain cases, the host cells produces cis-N-methylstylopine, where tetrahydroprotoberberine N-methyltransferase (TNMT; EC 2.1.1.122) (e.g., from *P. somniferum* (PsTNMT) or *E. californica* (EcTNMT)) is expressed in the host cell from a low copy construct (e.g., a low copy plasmid, YAC or chromosomally integrated) in a stylopine-producing strain. Any convenient variants of the enzymes may be utilized, e.g., one of more of the enzyme variants depicted in Table 2.

In some instances, the host cells produce protopine. In certain cases, cis-N-methylstylopine 14-hydroxylase (MSH, EC 1.14.13.37) (e.g., from *P. somniferum* (PsMSH)) is expressed in the host cell from a low copy construct (e.g., a low copy plasmid, YAC or chromosomally integrated) in a cis-N-methylstylopine producing strain. In certain instances, the host cell comprises heterologous coding sequences for a TNMT and a MSH enzyme. Any convenient variants of the enzymes may be utilized, e.g., one of more of the enzyme variants depicted in Table 2.

In some cases, the host cell produces dihydrosanguinarine, where protopine 6-hydroxylase (P6H; EC 1.14.13.55) (e.g., from *E. californica* (EcP6H) or *P. somniferum* (PsP6H)) is expressed in the host cell from a low copy construct (e.g., a low copy plasmid, YAC or chromosomally integrated) in a protopine producing strain. Any convenient variants of the enzymes may be utilized, e.g., one of more of the enzyme variants depicted in Table 2.

In some cases, the host cell produces sanguinarine, where dihydrobenzophenanthridine oxidase (DBOX; EC 1.5.3.12) (e.g., from *P. somniferum* (PsDBOX)) is expressed in the host cell from a low copy construct (e.g., a low copy plasmid, YAC or chromosomally integrated) in a dihydrosanguinarine producing strain. Any convenient variants of the enzymes may be utilized, e.g., one of more of the enzyme variants depicted in Table 2.

In some embodiments, the host cell is an engineered strain that produces more cheilanthifoline than a control strain, where additional copies of CFS are expressed in the engineered strain. By more is meant both the production of some amount of cheilanthifoline where the control has no cheilanthifoline production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some cheilanthifoline production. Varying the expression level of a cytochrome P450 of interest, through gene copy number, promoter strength or promoter regulation may improve the production of target compounds. In certain cases, expression from a high copy plasmid does not result in measureable cheilanthifoline production. In certain instances, when one or multiple copies of the CFS gene are expressed in a host cell from low copy constructs, cheilanthifoline production is higher. In some embodiments, when more copies of CFS gene are included in the host cell, the levels of cheilanthifoline are higher.

In certain instances, to produce more stylopine, variants of enzymes CFS and STS from different species are expressed in combination in a host cell. Increased levels of stylopine may be observed by comparison of the engineered host cell with a control cell that does not include the desired expression of enzymes of interest. By increased is meant both the production of some amount of stylopine where the control has no stylopine production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some stylopine production. For example, the measurement of stylopine production from different CFS variants expressed with different variants of STS is shown in FIG. 13(c). Any convenient combinations of enzymes may be utilized to produce increased levels of stylopine.

In some instances, to produce more cheilanthifoline, host cells (e.g., yeast strains) are engineered to include chromosomally integrated NADPH cytochrome P450 reductases from a variety of species to optimize the activity of cytochrome P450s. For example, the measurement of cheilanthifoline production from various cheilanthifoline synthase enzymes expressed with variants of cytochrome P450 NADPH reductase enzymes may be performed. Any convenient combinations of these enzymes may be utilized to produce increased levels of cheilanthifoline relative to a control.

In certain cases, to produce more cheilanthifoline or stylopine, host cells (e.g., yeast strains) that overexpress cytochrome $b_5$ are utilized to optimize the activity of cytochrome P450s. For example, the measurement of cheilanthifoline or stylopine production from host cells with and without cytochrome $b_5$ overexpressed may be performed. In some cases, the host cell overexpresses cytochrome $b_5$ and produces an increased level of cheilanthifoline or stylopine relative to a control cell.

In certain embodiments, to produce more protoberberine alkaloids, the host cell is cultured in conditions that provide for improved cytochrome P450 activity. Conditions of interest include, but are not limited to, growth at a reduced temperature (e.g., about 10° C., about 15° C., about 20° C., about 22° C., about 25° C., about 28° C., about 30° C., about 33° C., or about 35° C.) and in a vessel that provides high aeration (e.g., a flask such as a baffled flask). For example, a variety of protoberberine alkaloids from host cells grown in different culture conditions may be measured. In certain embodiments, the hosts cells are incubated at reduced temperature (e.g., about 25° C.) and under higher aeration conditions (e.g., in a flask). Under such conditions, the enzymes levels and/or enzyme activity (e.g., production of cheilanthifoline and stylopine) may be increased relative to a control.

In some embodiments, the host cells produce more protoberberine alkaloids where the host cell is optimized by the deletion of genes associated with the unfolded protein response and endoplasmic reticulum (ER) proliferation to improve BIA production. Gene deletions of interest include, but are not limited to, IRE1, HAC1, OPI1, INO1, INO2, and INO3 (e.g., Table 3. In some cases, the expression of cytochrome P450s induces the unfolded protein response and causes the ER to proliferate. Deletion of genes associated with these stress responses may control or reduce overall burden on the host cell and improve pathway performance. By more is meant both the production of some amount of protoberberine alkaloids where the control has no protoberberine alkaloids production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some protoberberine alkaloids production.

In certain instances, the host cell comprises one or more heterologous or endogenous coding sequences for one or more proteins involved in transport of compounds across the cell membrane. In certain cases, the one or more proteins involved in transport of compounds across the cell membrane is selected from PDR1, PDR5, SNQ2, YOR1, PDR3, CIN5, and PDR3.

In certain embodiments, genes involved in the pleiotropic drug response, including, but not limited to, ATP-binding cassette (ABC) transporters, multidrug resistance (MDR) pumps and associated transcription factors, are deleted in the host cell to reduce the export of BIA molecules into the culture medium. Examples of genes include, but are not limited to, PDR1, STB5, PDR3, PDR5, SNQ2, YOR1, TPO1, TPO2, TPO3, TPO4, PDR10, PDR11, PDR15, PDR16, PDR17, QDR1, QDR2, QDR3, FLR1, AQR1, AQR2, and CIN5. Gene deletions include single deletions or multiple deletions in any combination. In some instances, the host cell include one or more gene deletions of interest and produces lower levels of reticuline, scoulerine, cheilanthifoline or stylopine than control cells that do not include the one or more gene deletions of interest.

In another embodiment, in the subject host cells, a gene involved in the pleiotropic drug response, including but not limited to ATP-binding cassette (ABC) transporters, multidrug resistance (MDR) pumps and associated transcription factors, are placed under the control of a regulated (e.g., inducible or growth stage dependent) promoter to implement temporal control of BIA transport. In certain cases, a transporter gene is placed under the control of a stationary phase promoter which causes a BIA of interest to be retained within the cell until stationary phase. In such host cells, the conversion of starting materials to the desired end products may be increased.

Protoberberine-producing Host Cells

Aspects of the invention include engineered host cells that produce protoberberine alkaloids. In some cases, the protoberberine alkaloids have one of the following structures:

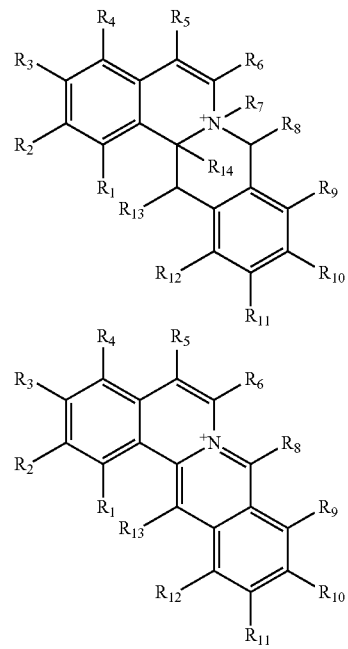

where $R_1$-$R_{14}$ are each independently selected from —H, an alkyl (e.g., a lower alkyl such as methyl ($CH_3$) or ethyl), a hydroxyl or an alkoxy (OR) (e.g., a lower alkoxy such as methoxy or ethoxy).

In certain instances, the protoberberine alkaloids are produced from reticuline or other analogs thereof, or derivatives thereof, e.g., present in the culture media (e.g., of a reticuline-producing cell, e.g., as described herein), or introduced to a cell lysate or lysate fraction. In certain cases, the host cells may include one or more heterologous coding sequences to express one or more of, or any combination of, the following enzymes: berberine bridge enzyme (BBE), scoulerine 9'-O-methyltransferase (S9OMT), canadine synthase (CAS), and (S)-tetrahydroprotoberberine oxidase (STOX), wherein the one or more enzymes is derived from a different source organism as compared to the host cell.

In some instances, the source organism is *P. somniferum, E. californica, C. japonica, T. flavum, Berberis stolonifer, T. flavum* subsp. *glaucum, Coptis chinensis, Thalictrum* spp, *Coptis* spp, *Papaver* spp, *Berberis wilsonae, A. mexicana*, or *Berberis* spp.

In certain embodiments, the host cell comprises multiple copies of the one or more heterologous coding sequences. In some case, the multiple copies of the one or more heterologous coding sequences are derived from two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In some instances, the host cell comprises two or more heterologous coding sequences for two or more enzymes selected from BBE, S9OMT, CAS and STOX. In some instances, the host cell comprises three or more heterologous coding sequences for three or more enzymes selected from BBE, S9OMT, CAS and STOX. In some instances, the host cell comprises heterologous coding sequences for each of the enzymes BBE, S9OMT, CAS and STOX.

In some embodiments, the host cell comprises the heterologous coding sequence for CAS and a heterologous coding sequence for ATR1. In certain embodiments, the host cell comprises the heterologous coding sequence for STOX.

Figure 5:
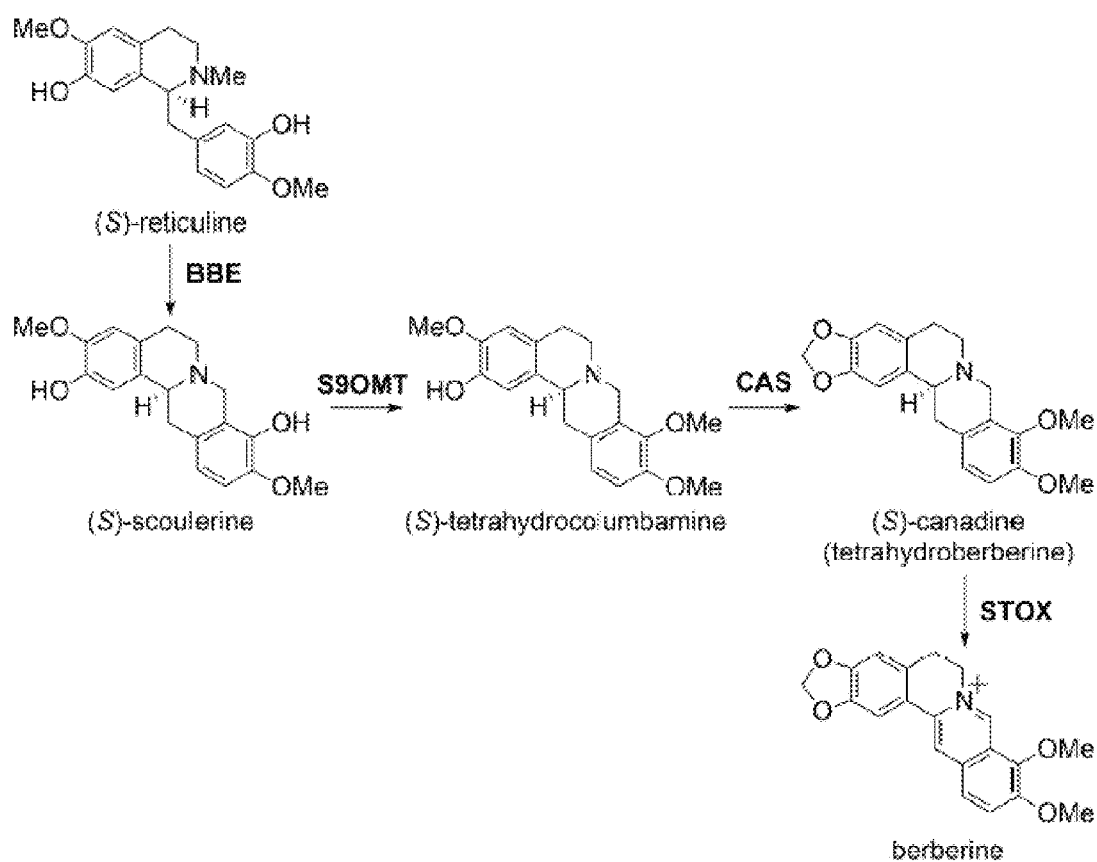
FIG. 5 depicts a biosynthetic pathway of interest from reticuline to berberine.

In some embodiments, the host cell (e.g., an engineered yeast strain) supports a biosynthetic pathway as depicted in FIG. 5.

In some instances, the host cell includes the gene STOX that shares 75% or more (e.g., 78%) nucleic acid sequence identity with the naturally occurring gene B. wilsonae (S)-tetrahydroprotoberberine oxidase (Table 3). The gene may be a non-natural nucleotide sequence, codon-optimized for yeast expression.

Aspects of the invention entail the functional expression of STOX or its homologues in live yeast culture. In certain embodiments, host cells are engineered to produce berberine from its precursor (S)-canadine.

In one embodiment of the invention, the expression levels for the enzymes are relatively low (e.g., CEN/ARS vector or genomic expression) for BBE, CAS, and STOX (see, e.g., FIG. 6a) and relatively high (e.g., 2 µm vector or multiple genomic copies) for S9OMT (see, e.g., FIG. 6b). The expression levels may be altered using any convenient method. Methods of interest include but are not limited to, changing the strength of the constitutive promoter, using an inducible promoter, changing the number of copies of each gene episomally or genomically (see, e.g., FIG. 6c), altering the selection marker, and/or culture conditions corresponding to promoter activity or selection.

Figure 10:
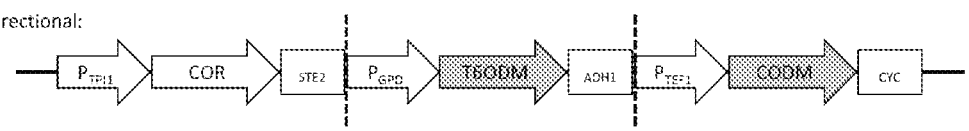
FIG. 10 depicts a design for a genetic construct which enhances promoter activity and prevents instability of two genes sharing sequence similarity, namely T6ODM and CODM.
Figure 10:
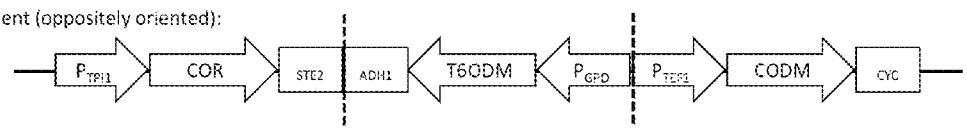
Figure 10:
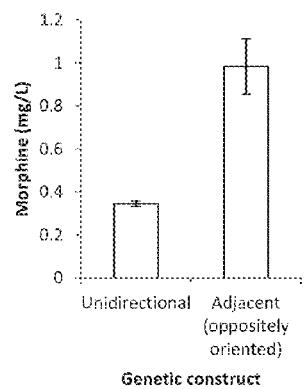
Figure 10:
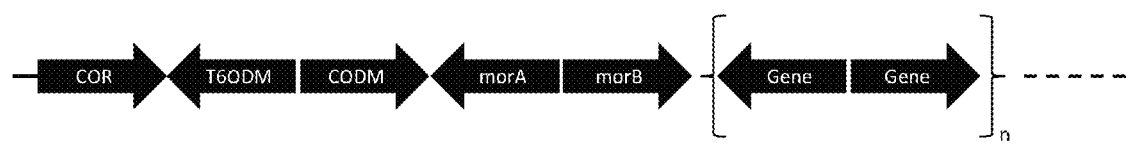

In some embodiments, the one or more enzymes are recombinantly expressed from a yeast artificial chromosome (e.g., FIG. 10).

Aspects of the invention include the functional expression of CAS or its homologues in live yeast culture as part of a larger biosynthetic pathway. In certain embodiments, the host strains are engineered to produce berberine from norlaudanosoline or its precursors (e.g., according to FIGS. 5, 7 or Table 2). In some instances, the host cell is capable of producing berberine from reticuline via a biosynthetic pathway of FIG. 5. In another embodiment of the invention, the host cell includes a cytochrome P450 reductase partner for CAS that is ATR1, the co-expression of which may result in higher CAS activity than E. californica CPR, A. thaliana ATR2, P. somniferum CPR, or endogenous yeast CPR (e.g., FIG. 6d).

Aspects of the invention entail the functional expression of STOX or its homologues in live yeast culture. In certain embodiments, host cells are engineered to produce (S)-canadine, the precursor of berberine, from norlaudanosoline. In some embodiments, the host cell is capable of producing (S)-canadine from norlaudanosoline.

In order to enhance the accumulation of BIAs within the yeast cell, heterologous transporters, including but not limited to plant ATP-binding cassette proteins from BIA-producing plants, may be expressed in the engineered strains. In some embodiments, one or more heterologous coding sequences for one or more transporters selected from CjABCB1, CjABCB2, and/or CjABCB2 may be included to accumulate berberine within the host cell.

In some cases, the host cell is a yeast strain.

Thebaine-producing Host Cells

Aspects of the invention include engineered host cells that produce thebaine, either as an intermediate or a final product, from reticuline or its precursors. The reticuline or its precursors may be produced by an existing strain, be present in the culture media, or introduced to a cell lysate or lysate fraction. In some instances, the host cells may include one or more heterologous coding sequences to express for one or more enzymes selected from salutaridine synthase (SalSyn), cytochrome P450 2D6 (CYP2D6), cytochrome P450 2D2 (CYP2D2), salutaridine reductase (SalR), and/or salutaridinol 7-O-acetyltransferase (SalAT). The one or more enzymes may be derived from a different source organism as compared to the host cell.

In some instances, the source organism is P. somniferum, P. bracteatum, Papaver orientale, Papaver spp, Homo sapiens, or Rattus norvegicus.

Figure 8:
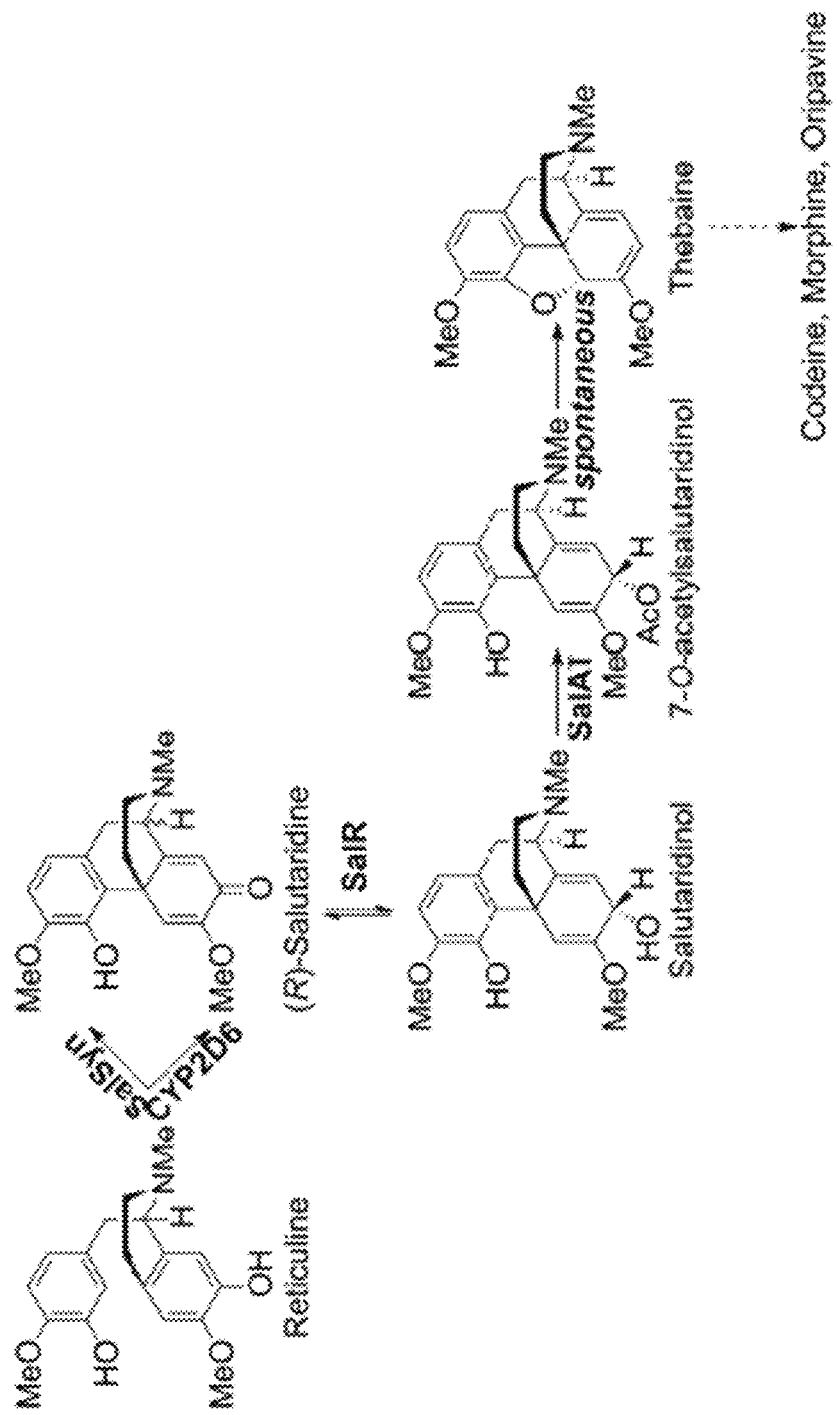
FIG. 8 depicts a biosynthetic pathway from reticuline to thebaine or its products.

In certain cases, the host cells are engineered yeast strains that support a biosynthetic pathway in a host as depicted in FIG. 8.

In certain embodiments, the host cell comprises multiple copies of the one or more heterologous coding sequences. In some case, the multiple copies of the one or more heterologous coding sequences are derived from two or more different source organisms as compared to the host cell.

In some instances, the host cell comprises two heterologous coding sequences. In certain instances, the two heterologous coding sequences are for the enzymes SalR and SalAT.

In some instances, the host cell includes the gene CYP2D6, CYP2D2, and/or SalSyn and/or another natural or engineered P450 that can produce salutaridine from reticuline. The gene may be a natural or non-natural nucleotide sequence, codon-optimized for yeast expression.

In some embodiments, the host cell includes a cytochrome P450 reductase partner for CYP2D6, CYP2D2, and/or SalSyn that is a mammalian CPR and/or ATR1, the co-expression of which may result in higher CYP2D6, CYP2D2, and/or SalSyn activity than E. californica CPR, A. thaliana ATR2, P. somniferum CPR, or endogenous yeast CPR.

In some embodiments, the host cell may include one or more heterologous coding sequences to express one or more of any SalR variant listed in Table 2. In some cases, the host cell may express one or more of any SalAT variant listed in Table 2. Additionally, the SalR variants may include the F104A and/or I275A mutations and/or any other convenient mutations (e.g., FIG. 9). Aspects of the invention include the functional expression of both SalR and SalAT, resulting in the production of thebaine from salutaridine.

Figure 9:
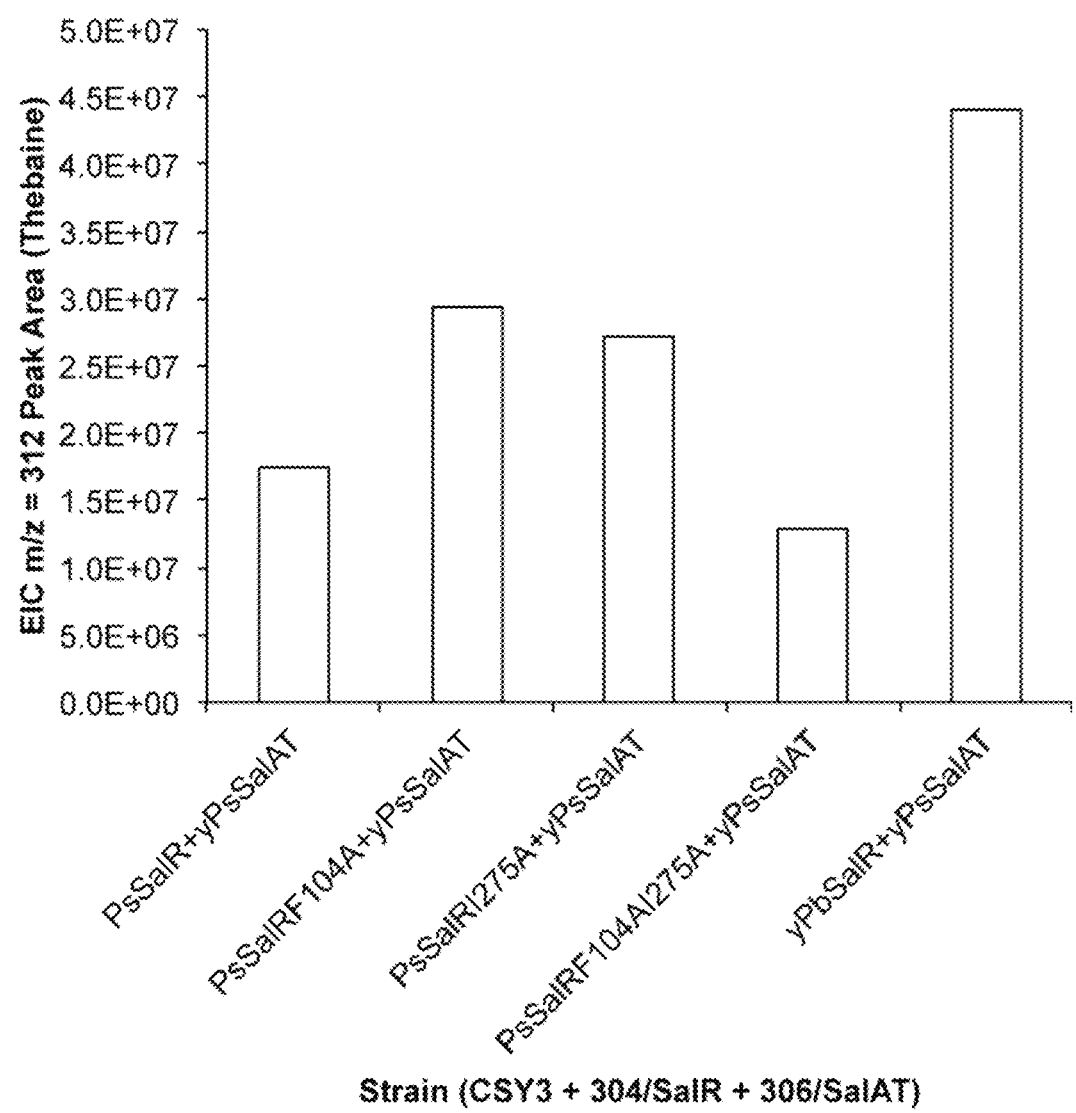
FIG. 9 depicts the results of combinations of salutaridine reductase (SalR) and salutaridinol 7-O-acetyltransferase (SalAT)variants in thebaine-producing strains.

In one embodiment of the invention, the host cell includes a combination of enzymes: codon-optimized P. bracteatum SalR with F104A or I275A mutations and any of the codon-optimized variants of SalAT (e.g., FIG. 9). The SalAT genes may share less than or equal to 80% nucleic acid sequence identity with their naturally occurring counterparts (Table 3). These genes may be non-natural nucleotide sequences, codon-optimized for yeast expression.

In another embodiment of the invention, the conversion of salutaridine to thebaine catalyzed by SalR and SalAT occurs in a crude lysate of the subject host cell expressing both enzymes supplemented by the cofactor NADPH. In another embodiment of the invention, SalAT and SalR may be expressed in an engineered host cell expressing any convenient additional enzymes such that the strain produces products for which thebaine is a precursor. In some cases, the strain may produce oripavine, morphine, codeine, hydromorphone, hydrocodone, oxycodone, and/or oxymorphone from thebaine.

In some instances, the host cell further comprises heterologous coding sequences for T6ODM and morB (e.g., morB or morB-E160G). In certain cases, the strain may produce one or more opiate compounds, such as hydrocodone.

In yet another embodiment of the invention, the conversion of reticuline to thebaine catalyzed by SalR and SalAT occurs in a host cell (e.g., an engineered yeast strain) that is modified to produce increased amounts of NADPH by comparison to a control host cell (e.g., a native yeast strain) (see, e.g., Table 2).

In one embodiment of the invention, SalR and/or SalAT and CYP2D2 or CYP2D6 or SalSyn or an engineered cytochrome P450 enzyme that catalyzes the conversion of reticuline to salutaridine are expressed from a yeast artificial chromosome.

In some cases, the host cell is a yeast strain. In certain instances, the host cell may be engineered to increase production of salutaridinol or thebaine or products for which thebaine is a precursor from reticuline or its precursors by localizing SalR and/or SalAT to organelles in the yeast cell. SalR and/or SalAT may be localized to the yeast endoplasmic reticulum in order to decrease the spatial distance between SalR and/or SalAT and CYP2D2 or CYP2D6 or SalSyn or an engineered cytochrome P450 enzyme that catalyzes the conversion of reticuline to salutaridine. By increased production is meant both the production of some amount of the compound of interest where the control has no production of the compound of interest, as well as an increase of 10% or more, such as 50% or more, including 2-fold or more, e.g., 5-fold or more, such as 10-fold or more in situations where the control has some production of the compound of interest.

Opiate-producing Host Cells

Aspects of the invention include engineered host cells expressing one or more of the following enzymes: thebaine 6-O-demethylase (T6ODM: EC 1.14.11.31), codeinone reductase (COR; EC 1.1.1.247), codeine O-demethylase (CODM: EC 1.14.11.32), morphine dehydrogenase (morA: EC 1.1.1.218 and EC 1.1.1.247) and morphinone reductase (morB: EC 1.3.1.-) (see, e.g., Table 2). The host cells may produce opiate compounds selected from including codeine, morphine, hydrocodone and hydromorphone, oxycodone, dihydrocodeine, 14-hydroxycodeine and dihydromorphine. By more is meant both the production of some amount of the compound of interest where the control has no production of the compound of interest, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some production of the compound of interest. The host cells may synthesize these products from thebaine, either supplied in the culture medium, or produced by the host cells itself, or produced by one or more strains co-cultured with the opiate-producing host cells. In some embodiments, the genetic modifications which comprise these host cells may be combined with those of thebaine-producing host cells to produce master strains capable of biosynthesizing opiates from upstream intermediates, tyrosine, or fermentable carbon sources.

The opiate compounds may be observed and measured using any convenient methods. Methods of interest include LC-MS methods (e.g., as described herein) where a sample of interest is analyzed by comparison with a known amount of a standard opiate compound. Identity may be confirmed, e.g., by m/z and MS/MS fragmentation patterns, and quantitation or measurement of the compound may be achieved via LC and/or EIC MS analysis by reference to a corresponding amount of standard of the compound.

Figure 15:
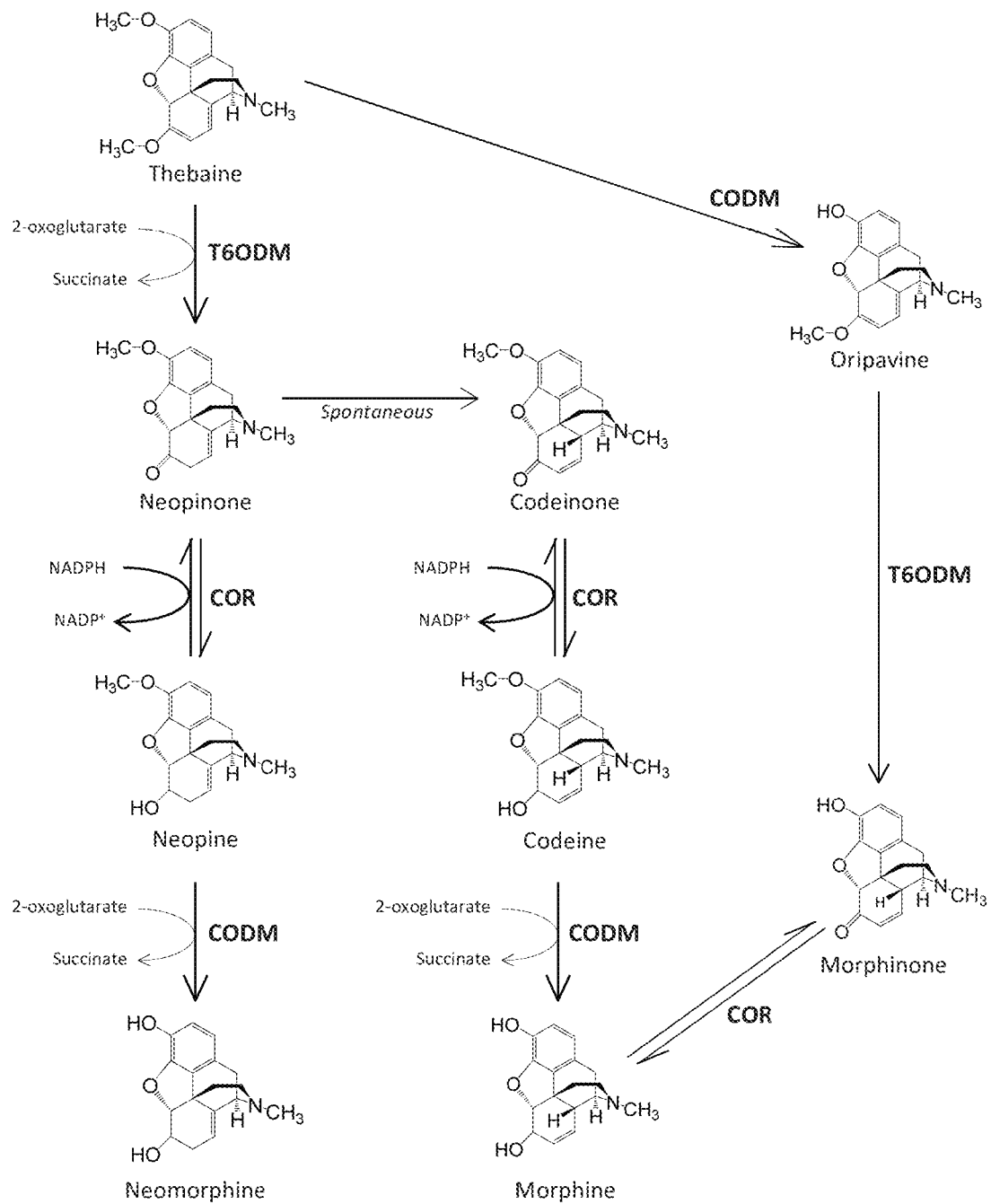
FIG. 15 depicts the engineering of a heterologous morphine biosynthesis pathway in yeast, including transformations of thebaine by the morphine biosynthesis enzymes—thebaine 6-O-demethylase (T6ODM), codeine O-demethylase (CODM), and codeinone reductase (COR) from opium poppy *P. somniferum*. Two routes to morphine which pass through intermediates codeinone and codeine (route i) and oripavine and morphinone (route ii). Additionally, a newly-identified route to neomorphine (iii), demonstrating a broader substrate range for COR and CODM.

In some embodiments, the host cell is capable of producing the opiate compound from thebaine via a biosynthetic pathway of FIG. 15.

In some cases, the host cell produces no oripavine or morphinone from thebaine. In certain instances, the host cell produces one or more of neopine and neomorphine.

In some instances, the host cell produces a yield of the opiate compound that is 10% or more of the total opiates, such as 20% or more, 30% or more, 40% or more, 50% or more, 50% or more, 50% or more, 50% or more, or even 90% or more of the total opiates in the host cell. In certain cases, the host cell produces a yield of the opiate compound that is 30% or more, such as 50% or more of the total opiates.

In some cases, the host cell is a cell that produces an opiate compound, wherein the host cell comprises four or more heterologous coding sequences for four or more enzymes selected from thebaine 6-O-demethylase (T6ODM), codeinone reductase (COR), codeine O-demethylase (CODM), morphine dehydrogenase (morA) and morphinone reductase (morB), wherein the four or more enzymes are derived from a different source organism as compared to the host cell.

In certain embodiments, the source organism is *P. somniferium*, *Papaver* spp. or *P. putida*.

In some embodiments, the host cell produces an opiate compound, wherein the host cell comprises: one or more heterologous coding sequences for one or more enzymes selected from T6ODM, COR, and CODM, wherein the one or more enzymes are derived from a different source organism as compared to the host cell; and one or more heterologous coding sequences for one or more enzymes selected from morA and morB, wherein the one or more enzymes are derived from a different source organism as compared to the host cell. In certain embodiments the morA is *P. putida* morA and the morB is *P. putida* morB. In certain embodiments, the host cell comprises four or more heterologous coding sequences.

In some instances, the host cell comprises heterologous coding sequences for T6ODM, COR, CODM and morA. In certain instances, the host cell comprises heterologous coding sequences for T6ODM, COR, CODM and morB. In certain instances, the host cell comprises heterologous coding sequences for T6ODM, CODM, morA and morB. In some embodiments, the host cell comprises heterologous coding sequences for the enzymes T6ODM, COR and CODM.

In certain cases, the host cell comprises multiple copies of one or more of the heterologous coding sequences. The multiple copies of the heterologous coding sequences may be derived from one or two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In some instances, host cell expresses one or more of the genes thebaine 6-O-demethylase (T6ODM), codeinone reductase (COR) and codeine O-demethylase (CODM). In certain cases, these genes (T6ODM, COR and CODM) share 76.2%, 76.8-77.7% and 75.2% nucleotide sequence similarity, respectively, with the naturally occurring genes from *P. somniferum* (see Table 3. In certain cases, the genes expressed in the engineered host cells represent non-natural nucleotide sequences which are optimized for the codon usage of the host cell, *S. cerevisiae*.

In some instances, the host cells support a metabolic pathway as depicted in FIG. 15. In certain cases, in the first step T6ODM acts on thebaine to make neopinone. However, some of the pool of neopinone in the yeast cell is then acted on by COR to make neopine, while some other molecules of neopinone spontaneously rearrange to form codeinone. Codeinone is also acted on by COR to make codeine. Neopine and codeine are then metabolized by CODM to make neomorphine and morphine respectively. This pathway may result in the production of non-target products neopine and neomorphine as well as the expected targets codeine and morphine. In some embodiments, the host cell provided a route to morphine utilizing the three enzymes T6ODM, COR and CODM (FIG. 15) where the engineered strains produce little or no oripavine or morphinone.

In one embodiment of the invention, the COR enzyme for the pathway is isoform 1.3 from *P. somniferum*. This isoform of COR may produce similar levels of codeine to other variants tested, but minimize the amount of non-target neopine.

In another embodiment, the host cell (e.g., a yeast strain) is engineered for selective production of codeine and morphine over neopine and neomorphine by localizing COR to compartments in the yeast cell. In one embodiment of the invention illustrated in FIG. 18, COR is localized to the yeast endoplasmic reticulum by fusing an ER2 targeting sequence to the C-terminus of the protein. T6ODM may be located in the cytoplasm of such a host cell such that neopinone produced by this enzyme spontaneously rearranges to codeinone before reaching the mitochondrial-localized COR enzyme. The spatial distance between the two enzymes may be selected to prevent COR from acting directly on neopinone to make neopine, and restrict production of non-target neopine and downstream neomorphine. In another embodiment of the invention, CODM is co-localized with COR to convert codeine produced by COR to morphine. In yet another embodiment, COR, either singularly or together with CODM, is be localized to any convenient compartment in the host cell (e.g., a yeast cell), including but not limited to the endoplasmic reticulum, Golgi, vacuole, nucleus, plasma membrane, and the periplasm (see FIG. 18).

In certain embodiments, the host cell (e.g., a yeast strain) has several copies of each heterologous coding sequence present in the cell either integrated in the chromosome or within episomal DNA. Any convenient ratios of heterologous coding sequences may be utilized in the subject host cells. In some instances optimized for the production of morphine, the ratio for the total number of copies of heterologous coding sequences for T6ODM:COR:CODM is 1:1:3, 2:1:2 or 2:1:3 (see, e.g., FIG. 17).

Figure 16:
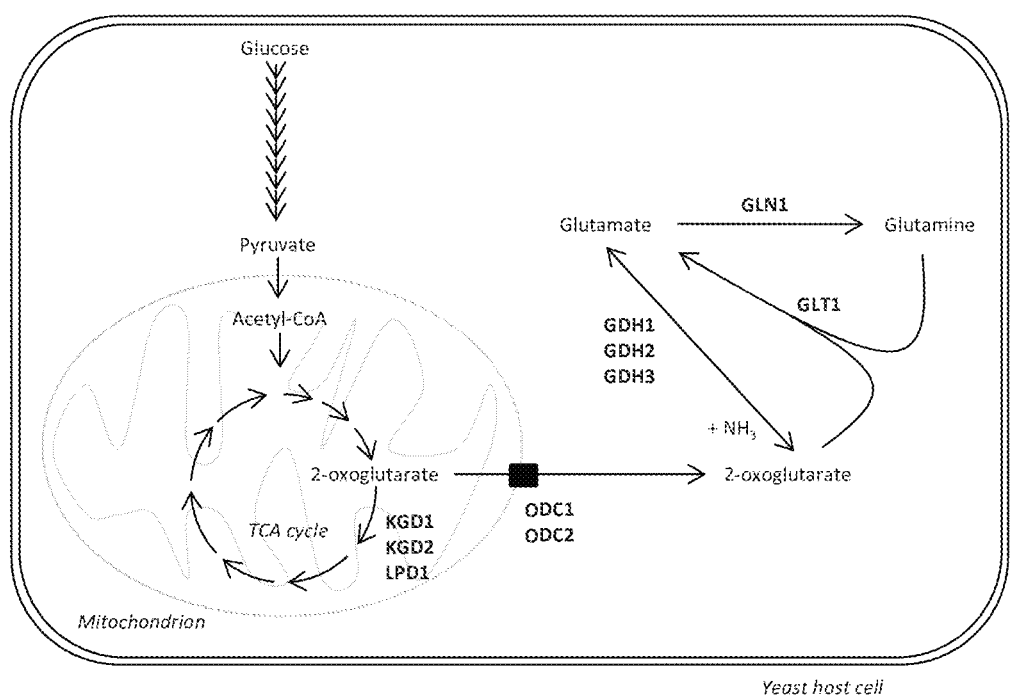
FIG. 16 depicts methods for (a) engineering the host yeast cell and (b) titrating additives in the culture medium to enhance morphine production by providing 2-oxoglutarate as a co-substrate for the morphine biosynthesis pathway.
Figure 16:
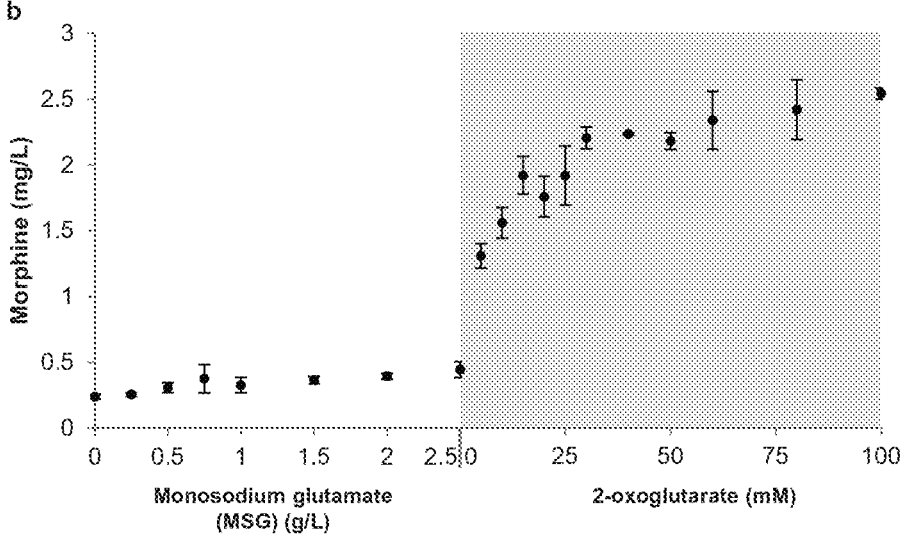

The culture medium may be optimized such that excess 2-oxoglutarate is available to support the activity of 2-oxoglutarate-dependent enzymes T6ODM and CODM. The culture medium may include any of the following additives used either individually or in combination: 2-oxoglutarate, glutamate, and glutamine (FIG. 16). In certain embodiments, the host cell is an engineered yeast strain capable of producing increased amounts of 2-oxoglutarate by comparison to a control yeast strain. In other embodiments, the 2-oxoglutarate is added directly to the culture media.

In some embodiments, the host cell further comprises increased amounts of 2-oxoglutarate by comparison to a control host cell (e.g., a yeast strain), wherein the increased amounts of 2-oxoglutarate are introduced via direct addition to the culture medium of the host cell. In some instances, the host cell further comprises increased amounts of one or two or three of glutamine, 2-oxoglutarate and glutamate by comparison to a control yeast strain.

In some instances, the host cell supports the activity of 2-oxoglutarate-dependent enzymes T6ODM and CODM such that additional co-substrate 2-oxoglutarate is made available to the heterologous enzymes from the host cell metabolism (see, e.g., FIG. 16). Such modifications of interest to the host cell genotype are detailed in Table 3 and may include any one or more of the following: (1) overexpression of glutamate dehydrogenase enzyme (GDH), either native or heterologous, to generate 2-oxoglutarate from glutamate, (2) deletion of glutamine synthase (GLN1) to prevent loss of glutamate in glutamine production, and/or deletion of glutamate synthase (GLT1) to prevent loss of 2-oxoglutarate in glutamate production, (3) deletion of one or several glutamate dehydrogenase genes (GDH1, GDH2, GDH3) to prevent the reversible conversion of glutamate to 2-oxoglutarate and ammonia, (4) deletion of one or several 2-oxoglutarate dehydrogenase genes (KGD1, KGD2, LPD1) to block loss of 2-oxoglutarate to succinyl-CoA, (5) and in addition, one or several mitochondrial 2-oxoglutarate transporters (including but not limited to ODC1 and ODC2) may be overexpressed or knocked out in the host cell.

In some instances, the host cell comprises one or more coding sequences for one or more proteins selected from GLN1, GLT1, GDH1, GDH2, GDH3, ODC1, ODC2, KGD1, KGD2 and LPD1.

In certain instances, in a production strain the promoters regulating expression of the pathway genes are positioned adjacent to each other and act in opposing directions such that two genes situated side-by-side are expressed from the sense and antisense strands (e.g., as illustrated in FIG. 10). Genetic cassettes comprising a promoter, gene and terminator may be arranged in pairs with such a back-to-back promoter design to increase expression and give a corresponding increase in morphine production over identical cassettes positioned unidirectionally. A DNA construct of interest having such an arrangement may be either incorporated in episomal DNA or chromosomal DNA or both. In some cases, when there is an odd number of genetic cassettes, the promoter of the gene without a pair is located adjacent to vector or chromosomal DNA.

In some embodiments, the host cell includes one or more of the enzymes that comprise a localization tag. In certain embodiments, one or more of the enzymes in the host cell is spatially localized to a compartment in the host cell. In certain case, the host cell is a yeast cell. Any convenient locations in a host cell may be utilized for localizing one or more enzymes. In certain cases, the host cellular compartment is selected from mitochondrion, endoplasmic reticulum (ER), Golgi, vacuole, nucleus, plasma membrane, and periplasm.

In some instances, the one or more enzymes is spatially localized to the outside of the compartment in the yeast cell. In certain instances, the one or more enzymes is spatially localized to the inside of the compartment in the yeast cell. In some cases, the one or more enzymes is COR. In some instances, the COR enzyme is localized to mitochondria in the yeast cell. In some embodiments, the host cell comprises COR and T6ODM enzymes that are spatially separated from each other in the cell.

In certain cases, if T6ODM and CODM, sharing a minimum of about 80% or more (e.g., 80.1%) similarity to each other, are expressed from the same DNA construct in the host cell, the genes are positioned back-to-back such that one is expressed from the sense strand and the other from the anti-sense strand. This design may enhance the stability of two sequences sharing homology.

In some instances, the movement of metabolites between the cell and culture medium may be altered to improve uptake or retention. For a single transformation such as the uptake of thebaine and conversion to neopinone by T6ODM (and spontaneous rearrangement to codeinone) up to 2% dimethyl sulfoxide (DMSO) may be included in the culture medium to enhance metabolite exchange with the culture medium such that more of the substrate is taken up by the cell and more of the product is released. For two or more transformations, plasma membrane transporters in the ATP-binding cassette class may be deleted such that intermediates in the heterologous pathway are retained in the subject host cell. This supports flux through the pathway and results in enhanced production of end-products. Alternatively, in some cases, the transporters may be temporally regulated such that expression is off during the exponential growth phase to in order retain intermediates, and then enhanced during the stationary phase to release end product metabolites to the culture medium.

Figure 20:
FIG. 20 depicts expansion of the opiate biosynthetic pathway in engineered yeast strains by incorporation of bacterial enzymes to allow for the biological synthesis of semi-synthetic opioids. Schematic depicting the extended transformations of thebaine in yeast by incorporating morA, morphine dehydrogenase, and morB, morphine reductase, from *Pseudomonas putida* M10 into the heterologous pathway.

In certain embodiments, the enzyme morphinone reductase (morB) (e.g., from *P. putida*) M10 is expressed in a host cell together with T6ODM to generate host cell strains that produce hydrocodone (see e.g., FIG. 20). The enzyme morB may include a mutation E160G.

In another embodiment of the invention, morphine dehydrogenase (morA), (e.g., from *P. putida* M10), is expressed in a host cell together with morB. Such host cells make hydromorphone from morphine both in vitro (e.g., in crude lysate) and in vivo (e.g, as live cells). In certain cases, morA includes mutation C81S. In some embodiments, a morA variant and morB are expressed together in the host cell with one or more of T6ODM, COR and CODM to make hydromorphone from thebaine. In certain embodiments, one or more variants of T6ODM, COR, CODM, morA and morB are expressed in thebaine-producing strains to form a total biosynthesis pathway for hydromorphone (FIG. 20).

In another embodiment of the invention, morA has enhanced supply of cofactors NADP+/NADPH to support activity of this enzyme. In certain embodiments, the nitrogen metabolism in the host cell is altered such that NADPH-dependent ammonia assimilation is decreased and replaced with NADH-dependent assimilation. Such host cells may include any one or more of the following genetic modifications: deletion of NADPH-dependent GDH1, deletion of NADPH-dependent GDH3, overexpression of NADH-dependent GDH2, or overexpression of a heterologous glutamate dehydrogenase (Table 3).

TABLE 1

Host Cell strains of interest

| Strain # | Enzyme Expression Cassettes | Starting compounds | BIA Products | Characteristics |
|---|---|---|---|---|
| 1 (FIG. 14) | Ps6OMT, PsCNMT, Ps4'OMT, PsBBE, EsCFS, ATR1, EcSTS, PsTNMT, PsMSH | Norlaudanosoline | Reticuline, scoulerine, cheilanthifoline, stylopine, cis-N-methylstylopine, protopine | Chromosomal integration and episomal |
| 2 (FIG. 7) | Ps6OMT, PsCNMT, Ps4'OMT, PsBBE, TfgS9OMT, TfgCAS, ATR1, BwSTOX | Norlaudanosoline | Reticuline, scoulerine, tetrahydrocolumbamine, canadine, berberine | Chromosomal integration, YAC, and episomal |
| 3 (FIG. 6A-B) | Ps6OMT, PsCNMT, Ps4'OMT, PsBBE, TfgS9OMT, TfgCAS, ATR1 | Norlaudanosoline | Reticuline, scoulerine, tetrahydrocolumbamine, canadine | Chromosomal integration and episomal |
| 4 (FIG. 6A and 6C) | BwSTOX | Canadine | Berberine | Episomal |
| 5 (FIG. 6A-B) | Ps6OMT, PsCNMT, Ps4'OMT, PsBBE, TfgS9OMT, TfgCAS, and one of ATR1, PsCPR, EcCPR, or no CPR | Norlaudanosoline | Reticuline, scoulerine, tetrahydrocolumbamine, canadine | Chromosomal integration and episomal |
| 6 (FIG. 8) | SalSyn, CYP2D2, or CYP2D6; PsSalR, PsSalR F105A, PsSalR I275A, or PbSalR and PsSalAT | Reticuline | Thebaine | Chromosomal integration, YAC, and episomal |
| 7 (FIG. 9) | PsSalR, PsSalR F105A, PsSalR I275A, or PbSalR and PsSalAT | Salutaridine | Thebaine | Chromosomal integration |

In some embodiments, the host cell is selected from one of the yeast strains 1-7 described in Table 1. In certain embodiments, the host cell is yeast strain 1, comprising heterologous coding sequences and capable of producing compounds as is described in the entry of Table 1. In certain embodiments, the host cell is yeast strain 2, comprising heterologous coding sequences and capable of producing compounds as is described in the entry of Table 1. In certain embodiments, the host cell is yeast strain 3, comprising heterologous coding sequences and capable of producing compounds as is described in the entry of Table 1. In certain embodiments, the host cell is yeast strain 4, comprising heterologous coding sequences and capable of producing compounds as is described in the entry of Table 1. In certain embodiments, the host cell is yeast strain 5, comprising heterologous coding sequences and capable of producing compounds as is described in the entry of Table 1. In certain embodiments, the host cell is yeast strain 6, comprising heterologous coding sequences and capable of producing compounds as is described in the entry of Table 1. In certain embodiments, the host cell is yeast strain 7, comprising heterologous coding sequences and capable of producing compounds as is described in the entry of Table 1. In some embodiments, the host cell is selected from one of the yeast strains described in Table 4. In certain embodiments, the host cell is yeast strain CSY905 (e.g., as described herein). In certain embodiments, the host cell is yeast strain CSY906 (e.g., as described herein). In certain embodiments, the host cell is yeast strain CSY950 (e.g., as described herein). In certain embodiments, the host cell is yeast strain CSY951 (e.g., as described herein). In certain embodiments, the host cell is yeast strain CSY952 (e.g., as described herein).

TABLE 2

Genes used as components of the engineered metabolic pathways in yeast

| Enzyme | Abbrev | Catalyzed Reactions | Source organisms | Similarity to naturally occurring gene | Modifications | Genbank # |
|---|---|---|---|---|---|---|
| Norcoclaurine 6-O-methyltransferase | 6OMT | Norcoclaurine → coclaurine Norlaudanosoline → 3'hydroxycoclaurine EC 2.1.1.128 | P. somniferum T. flavum C. japonica | 100% | | AY268894 AY610507 D29811 |
| Coclaurine-N-methyltransferase | CNMT | Coclaurine → N-methylcoclaurine 3'hydroxycoclaurine → 3'-hydroxy-N-methylcoclaurine EC 2.1.1.140 | P. somniferum T. flavum C. japonica | 100% | | AY217336 AY610508 AB061863 |
| 4'-O-methyltransferase | 4'OMT | 3'-hydroxy-N-methylcoclaurine → Reticuline EC 2.1.1.116 | P. somniferum T. flavum C. japonica | 100% | | AY217333, AY217334 AY610510 D29812 |
| Berberine bridge enzyme | BBE | Reticuline → scoulerine EC 1.21.3.3 | P. somniferum E. californica C. japonica T. flavum B. stolonifer | 100% | | AF025430 AF005655 AB747097 AY610511 AF049347 |
| Cheilanthifoline synthase | CFS | Scoulerine → cheilanthifoline EC 1.14.21.2 | P. somniferum E. californica A. mexicana | 79% 77% 78% | Codon optimized for expression in S. cerevisiae | GU325749 AB434654 EF451152 |
| Stylopine synthase | STS | Cheilanthifoline → stylopine EC 1.14.21.1 | P. somniferum E. californica A. mexicana | 79% 78% 76% | Codon optimized for expression in S. cerevisiae | GU325750 AB126257 EF451151 |
| Tetrahydroprotoberberine-N-methyltransferase | TNMT | Stylopine → cis-N-methylstylopine EC 2.1.1.122 | P. somniferum E. californica P. bracteatum A. mexicana | 100% | | DQ028579 EU882977 EU882994 HQ116698 |
| Cis-N-methylstylopine 14-hydroxylase | MSH | cis-N-methylstylopine → protopine EC 1.14.13.37 | P. somniferum | 79% | Codon optimized for expression in S. cerevisiae | KC154003 |
| Protopine-6-hydroxylase | P6H | Protopine → 6-hydroxyprotopine EC 1.14.13.55 | E. californica P. somniferum | 79% | Codon optimized for expression in S. cerevisiae | AB598834 AGC92397 |
| Dihydrobenzophenanthridine oxidase | DBOX | Dihydrosanguinarine → sanguinarine EC 1.5.3.12 | P. somniferum | 100% | Codon optimized for expression in S. cerevisiae | [not in genbank] |
| NADPH: hemoprotein oxidoreductase, also known as cytochrome P450 reductase | ATR1, CPR | NADPH + H$^+$ + n oxidized hemoprotein = NADP$^+$ + n reduced hemoprotein EC 1.6.2.4 | E. californica P. somniferum H. sapiens S. cerevisiae A. thaliana | 100% | Expressed from ARS/CEN vector, 2 µm vector, YAC and/or genome at various promoter strengths | AAC05022 AAC05021 P16435 P16603 Q9SB48, many others (see [27]) |
| (S)-tetrahydroprotoberberine oxidase | STOX | (S)-tetrahydroberberine + 2 O$_2$ = berberine + 2 H$_2$O$_2$ EC 1.3.3.8 | B. wilsonae C. japonica Berberis spp Coptis spp | 78% | Codon-optimized by GeneArt for expression in S. cerevisiae; Expressed from ARS/CEN vector, 2 µm vector, YAC and/ | HQ116697, AB564543 |

TABLE 2-continued

Genes used as components of the engineered metabolic pathways in yeast

| Enzyme | Abbrev | Catalyzed Reactions | Source organisms | Similarity to naturally occurring gene | Modifications | Genbank # |
|---|---|---|---|---|---|---|
| S-adenosyl-L-methionine: (S)-scoulerine 9-O-methyltransferase | S9OMT | S-adenosyl-L-methionine + (S)-scoulerine = S-adenosyl-L-homocysteine + (S)-tetrahydrocolumbamine EC 2.1.1.117 | T. flavum subsp. glaucum C. japonica C. chinensis P. somniferum Thalictrum spp. Coptis spp. Papaver spp. | 100% | or genome Expressed from ARS/CEN vector, 2 μm vector, YAC and/or genome | AY610512, D29809, EU980450, JN185323 |
| (S)-tetrahydrocolumbamine, NADPH: oxygen oxidoreductase (methylenedioxy-bridge-forming), also known as (S)-canadine synthase | CAS | (S)-tetrahydrocolumbamine + NADPH + H$^+$ + O$_2$ = (S)-canadine + NADP$^+$ + 2 H$_2$O EC 1.14.21.5 | T. flavum subsp. glaucum C. japonica Thalictrum spp. Coptis spp. | 100% | Expressed from ARS/CEN vector, 2 mm vector, and/or genome | AY610513, AB026122, AB374407, AB374408 |
| (S)-reticuline: oxygen oxidoreductase (methylene-bridge-forming), also known as berberine bridge enzyme | BBE | (S)-reticuline + O$_2$ = (S)-scoulerine + H$_2$O$_2$ EC 1.21.3.3 | P. somniferum A. mexicana E. californica B. stolonifera T. flavum subsp. Glaucum C. japonica Papaver spp. Eschscholzia spp. Berbis spp. Thalictrum spp. Coptis spp. | 99% | Expressed from ARS/CEN vector, 2 mm vector, and/or genome | AF025430, EU881889, EU881890, S65550 AF005655, AF049347, AY610511, AB747097 |
| salutaridinol: NADP$^+$ 7-oxidoreductase, also known as salutaridine reductase | SalR | salutaridinol + NADP$^+$ = salutaridine + NADPH + H$^+$ EC 1.1.1.248 | P. somniferum P. bracteatum Papaver spp. | 80-100% | Codon-optimized by DNA2.0 for expression in S. cerevisiae; site-directed mutants; expressed from ARS/CEN vector, 2 mm vector, and/ or genome | DQ316261, EF184229 |
| acetyl-CoA: salutaridinol 7-O-acetyltransferase | SalAT | acetyl-CoA + salutaridinol = CoA + 7-O-acetylsalutaridinol EC 2.3.1.150 | P. somniferum P. bracteatum P. orientale Papaver spp | 77-80% | Codon-optimized by Life Technologies or DNA2.0 for expression in S. cerevisiae; expressed from ARS/CEN vector, 2 mm vector, and/or genome | AF339913, FJ200355, FJ200358, FJ200356, JQ659008 |
| (R)-reticuline, NADPH: oxygen oxidoreductase (C-C phenol-coupling), also known as salutaridine synthase | SalSyn | (R)-reticuline + NADPH + H$^+$ + O$_2$ = salutaridine + NADP$^+$ + 2 H$_2$O EC 1.14.21.4 | P. somniferum, Papaver spp | 78% | Codon-optimized by DNA2.0 for expression in S. cerevisiae; expressed from ARS/CEN vector, 2 mm vector, and/or genome | EF451150 |
| Cytochrome P450, family 2, subfamily D, polypeptide2/6 | CYP2D6 CYP2D2 | Promiscuous oxidase, can perform (R)-reticuline + NADPH + H$^+$ + O$_2$ = salutaridine + NADP$^+$ + 2 H$_2$O among other reactions EC 1.14.14.1 | H. sapiens R. norvegicus | 73% 100% | Codon-optimized by DNA2.0 for expression in S. cerevisiae; expressed from ARS/CEN vector, 2 mm vector, and/or genome | BC067432 BC078897 |
| Thebaine 6-O demethylase | T6ODM | thebaine → neopinone EC 1.14.11.31 | P. somniferum Papaver spp. | 76.2% | Codon optimized for expression in S. cerevisiae | GQ500139.1 |
| Codeinone reductase | COR | codeinone → codeine EC 1.1.1.247, neopinone → neopine | P. somniferum Papaver spp. | 77.7% 76.8% 77.3% 77.0% | Codon optimized, addition of targeting sequences for mitochondria, vacuole, ER. | AF108432.1 AF108433.1 AF108434.1 AF108435.1 |
| Codeine O-demethylase | CODM | codeine → morphine EC 1.14.11.32, | P. somniferum P. spp. | 75.2% | Codon optimized, addition of | GQ500141.1 |

TABLE 2-continued

Genes used as components of the engineered metabolic pathways in yeast

| Enzyme | Abbrev | Catalyzed Reactions | Source organisms | Similarity to naturally occurring gene | Modifications | Genbank # |
|---|---|---|---|---|---|---|
| Morphine dehydrogenase | morA | neopine → neomorphine<br>morphine → morphinone<br>EC 1.1.1.218,<br>codeinone → codeine<br>EC 1.1.1.247 | *P. putida* | 73.7% | targeting sequence for mitochondria Codon optimized, introduced mutation morA$^{C81S}$ | M94775.1 |
| Morphinone reductase | morB | codeinone → hydrocodone<br>morphinone → hydromorphone<br>EC 1.3.1.— | *P. putida* | 67.2% | Codon optimized, introduced mutation morB$^{E160G}$ | U37350.1 |

TABLE 3

Modifications of the host cell metabolic processes

| Protein | Abbrev | Function | Deleted or altered expression | Locus |
|---|---|---|---|---|
| Pleiotropic drug resistance 1 | PDR1 | Transcription factor that regulates the pleiotropic drug response | Both | YGL013C |
| Pleiotropic drug resistance 5 | PDR5 | Plasma membrane ATP-binding cassette (ABC) transporter | Both | YOR153W |
| Sensitivity to 4-Nitro-Quinoline-N-oxide 2 | SNQ2 | Plasma membrane ATP-binding cassette (ABC) transporter | Both | YDR011W |
| Yeast Oligomycin Resistance 1 | YOR1 | Plasma membrane ATP-binding cassette (ABC) transporter | Both | YGR281W |
| Pleiotropic drug resistance 3 | PDR3 | Transcriptional activator of the pleiotropic drug resistance network | Both | YBL005W |
| Chromosome instability 5 | CIN5 | Basic leucine zipper (bZIP) transcription factor; mediates pleiotropic drug resistance and salt tolerance; | Both | YOR028C |
| Over-producer of inositol 1 | OPI1 | Transcriptional regulator of a variety of genes | Delete | YHL020C |
| Inositol-requiring 1 | IRE1 | transmembrane protein that mediates the unfolded protein response | Delete | YHR079C |
| Glutamate dehydrogenase 1 | GDH1 | Reversible synthesis of glutamate from 2-oxoglutarate and ammonia (NADPH-dependent) | Both | YOR375C |
| Glutamate dehydrogenase 2 | GDH2 | Reversible synthesis of glutamate from 2-oxoglutarate and ammonia (NADH-dependent) | Both | YDL215C |
| Glutamate dehydrogenase 3 | GDH3 | Reversible synthesis of glutamate from 2-oxoglutarate and ammonia (NADPH-dependent) | Both | YAL062W |
| Glutamate synthase | GLT1 | Synthesizes glutamate from glutamine and 2-oxoglutarate | Delete | YDL171C |
| Glutamine synthase | GLN1 | Synthesizes glutamine from glutamate and ammonia | Both | YPR035W |
| α-ketoglutarate dehydrogenase 1 | KGD1 | Component of the α-ketoglutarate dehydrogenase which decarboxylates 2-oxoglutarate to form succinyl-CoA | Delete | YIL125W |
| α-ketoglutarate dehydrogenase 2 | KGD2 | Component of the α-ketoglutarate dehydrogenase which decarboxylates 2-oxoglutarate to form succinyl-CoA | Delete | YDR148C |
| Lipoamide dehydrogenase | LPD1 | Component of the α-ketoglutarate dehydrogenase which decarboxylates 2-oxoglutarate to form succinyl-CoA | Delete | YFL018C |
| Oxodicarboxylate carrier 1 | ODC1 | Mitochondrial 2-oxoglutarate transporter | Both | YPL134C |
| Oxodicarboxylate carrier 2 | ODC2 | Mitochondrial 2-oxoglutarate transporter | Both | YOR222W |
| *Clostridium symbiosum* glutamate dehydrogenase | CsGDH | Heterologous glutamate dehydrogenase | Expression of heterologous gene | GenBank: Z11747.1 |
| *E. coli* glutamate dehydrogenase | EcGDH, gdhA | Heterologous glutamate dehydrogenase | Expression of heterologous gene | GenBank: K02499.1 |
| *H. sapiens* glutamate dehydrogenase | HsGDH, GLUD1 | Heterologous glutamate dehydrogenase | Expression of heterologous gene | GenBank: X07769.1 |
| *A. thaliana* glutamate dehydrogenase | AtGDH | Heterologous glutamate dehydrogenase | Expression of heterologous gene | GenBank: AED92515.1, AED91158.1 |

TABLE 4

Engineered *S. cerevisiae* strains utilized

| Strain | FIG. | x-axis label | Expression cassettes included in pYES1L plasmid | Genome modifications |
|---|---|---|---|---|
| CSY907* | 1, 2 | Strain CSY907 | $P_{GPD}$-T6ODM-$T_{ADH1}$, $P_{TPI1}$-COR1.3-$T_{STE2}$, $P_{TEF1}$-CODM-$T_{CYC1}$ | |
| CSY908 | Sup. 1 | Empty Vector Control | None | |
| CSY905 | Sup. 4 | — | $P_{GPD}$-T6ODM-$T_{ADH1}$ | |
| CSY906 | Sup. 4 | — | $P_{GPD}$-T6ODM-$T_{ADH1}$, $P_{TPI1}$-COR1.3-$T_{STE2}$ | |
| CSY921 | 3 | 1:3:1 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-COR1.3-$T_{CYC1}$, his3Δ::$P_{GPD}$-COR1.3-$T_{CYC1}$ |
| CSY922 | 3 | 1:2:1 | $P_{GPD}$-T6ODM-$T_{ADH1}$, $P_{TPI1}$-COR1.3-$T_{STE2}$, $P_{TEF1}$-CODM-$T_{CYC1}$ | his3Δ::$P_{GPD}$-COR1.3-$T_{CYC1}$ |
| CSY923 | 3 | 2:2:1 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-T6ODM-$T_{CYC1}$, his3Δ::$P_{GPD}$-COR1.3-$T_{CYC1}$ |
| CSY924 | 3 | 3:2:1 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-T6ODM-$T_{CYC1}$, his3Δ::$P_{GPD}$-T6ODM-$T_{CYC1}$, leu2Δ::$P_{GPD}$-COR1.3-$T_{CYC1}$ |
| CSY925 | 3 | 2:1:1 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-T6ODM-$T_{CYC1}$ |
| CSY907* | 3 | 1:1:1 | $P_{GPD}$-T6ODM-$T_{ADH1}$, $P_{TPI1}$-COR1.3-$T_{STE2}$, $P_{TEF1}$-CODM-$T_{CYC1}$ | |
| CSY928 | 3 | 3:1:1 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-T6ODM-$T_{CYC1}$, his3Δ::$P_{GPD}$-T6ODM-$T_{CYC1}$ |
| CSY927 | 3 | 1:1:2 | $P_{GPD}$-T6ODM-$T_{ADH1}$, $P_{TPI1}$-COR1.3-$T_{STE2}$, $P_{TEF1}$-CODM-$T_{CYC1}$ | his3Δ::$P_{GPD}$-CODM-$T_{CYC1}$ |
| CSY928 | 3 | 1:1:3 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-CODM-$T_{CYC1}$, his3Δ::$P_{GPD}$-CODM-$T_{CYC1}$ |
| CSY929 | 3 | 2:1:2 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-T6ODM-$T_{CYC1}$, his3Δ::$P_{GPD}$-CODM-$T_{CYC1}$ |
| CSY930 | 3 | 2:1:3 | $P_{GPD}$-T6ODM-$T_{ADH1}$, $P_{TPI1}$-COR1.3-$T_{STE2}$, $P_{TEF1}$-CODM-$T_{CYC1}$ | ura3Δ::$P_{GPD}$-T6ODM-$T_{CYC1}$, his3Δ::$P_{GPD}$-CODM-$T_{CYC1}$, leu2Δ::$P_{GPD}$-CODM-$T_{CYC1}$ |
| CSY907* | 4 | Untagged | $P_{GPD}$-T6ODM-$T_{ADH1}$, $P_{TPI1}$-COR1.3-$T_{STE2}$, $P_{TEF1}$-CODM-$T_{CYC1}$ | |
| CSY934 | 4 | ER1 | $P_{GPD}$-T6ODM-$T_{ADH1}$, $P_{TPI1}$-COR1.3-ER1-$T_{STE2}$, $P_{TEF1}$-CODM-$T_{CYC1}$ | |
| CSY935 | 4 | ER2 | $P_{GPD}$-T6ODM-$T_{ADH1}$, $P_{TPI1}$-COR1.3-ER2-$T_{STE2}$, $P_{TEF1}$-CODM-$T_{CYC1}$ | |
| CSY936 | 4 | ER3 | $P_{GPD}$-T6ODM-$_{ADH1}$, $P_{TPI1}$-ER3-COR1.3-HDEL-$_{STE2}$, $P_{TEF1}$-CODM-$_{CYC1}$ | |
| CSY937 | 4 | V1 | $P_{GPD}$-T6ODM-$T_{ADH1}$, $P_{TPI1}$-COR1.3-V1-$T_{STE2}$, $P_{TEF1}$-CODM-$T_{CYC1}$ | |
| CSY938 | 4 | PM1 | $P_{GPD}$-T6ODM-$T_{ADH1}$, $P_{TPI1}$-COR1.3-PM1-$T_{STE2}$, $P_{TEF1}$-CODM-$T_{CYC1}$ | |
| CSY941 | 4 | MT1 | $P_{GPD}$-T6ODM-$T_{ADH1}$, $P_{TPI1}$-MT1-COR1.3-$T_{STE2}$, $P_{TEF1}$-CODM-$T_{CYC1}$ | |
| CSY931 | 4 | COR1.1 | $P_{GPD}$-T6ODM-$T_{ADH1}$, $P_{TPI1}$-COR1.1-$T_{STE2}$, $P_{TEF1}$-CODM-$T_{CYC1}$ | |
| CSY932 | 4 | COR1.2 | $P_{GPD}$-T6ODM-$T_{ADH1}$, $P_{TPI1}$-COR1.2-$T_{STE2}$, $P_{TEF1}$-CODM-$T_{CYC1}$ | |
| CSY907* | 4 | COR1.3 | $P_{GPD}$-T6ODM-$T_{ADH1}$, $P_{TPI1}$-COR1.3-$T_{STE2}$, $P_{TEF1}$-CODM-$T_{CYC1}$ | |
| CSY933 | 4 | COR1.4 | $P_{GPD}$-T6ODM-$T_{ADH1}$, $P_{TPI1}$-COR1.4-$T_{STE2}$, $P_{TEF1}$-CODM-$T_{CYC1}$ | |
| CSY939 | 4 | COR1.1 (+MT1 tag) | $P_{GPD}$-T6ODM-$T_{ADH1}$, $P_{TPI1}$-MT1-COR1.1-$T_{STE2}$, $P_{TEF1}$-CODM-$T_{CYC1}$ | |
| CSY940 | 4 | COR1.2 (+MT1 tag) | $P_{GPD}$-T6ODM-$T_{ADH1}$, $P_{TPI1}$-MT1-COR1.2-$T_{STE2}$, $P_{TEF1}$-CODM-$T_{CYC1}$ | |
| CSY941 | 4 | COR1.3 (+MT1 tag) | $P_{GPD}$-T6ODM-$T_{ADH1}$, $P_{TPI1}$-MT1-COR1.3-$T_{STE2}$, $P_{TEF1}$-CODM-$T_{CYC1}$ | |
| CSY942 | 4 | COR1.4 (+MT1 tag) | $P_{GPD}$-T6ODM-$T_{ADH1}$, $P_{TPI1}$-MT1-COR1.4-$T_{STE2}$, $P_{TEF1}$-CODM-$T_{CYC1}$ | |
| CSY943 | 5 | T6ODM, CODM, COR1.3, morA, morB | $P_{GPD}$-T6ODM-$T_{ADH1}$, $P_{TPI1}$-COR1.3-$T_{STE2}$, $P_{TEF1}$-CODM-$T_{CYC1}$, $P_{PYK1}$-morA-$T_{MFa1}$, $P_{PGK1}$-morB-$T_{PHO5}$ | |
| CSY944 | 5 | T6ODM, CODM, morA, | $P_{GPD}$-T6ODM-$T_{ADH1}$, $P_{TEF1}$-CODM-$T_{CYC1}$, $P_{TPI1}$-morA-$T_{STE2}$ | |
| CSY945 | 5 | T6ODM, CODM, morA, morB | $P_{GPD}$-T6ODM-$T_{ADH1}$, $P_{TEF1}$-CODM-$T_{CYC1}$, $P_{PYK1}$-morA-$T_{MFa1}$, $P_{PGK1}$-morB-$T_{PHO5}$ | |
| CSY946 | 5 | T6ODM, morB | $P_{GPD}$-T6ODM-$T_{ADH1}$, $P_{PGK1}$-morB-$T_{PHO5}$ | |

TABLE 4-continued

Engineered *S. cerevisiae* strains utilized

| Strain | FIG. | x-axis label | Expression cassettes included in pYES1L plasmid | Genome modifications |
|---|---|---|---|---|
| CSY947 | 5 | mor A$^{C81B}$ morB | P$_{GPD}$-T6ODM-T$_{ADH1}$, P$_{TEF1}$-CODM-T$_{CYC1}$, P$_{PYK1}$-morA$^{C81S}$-T$_{MFa1}$, P$_{PGK1}$-morB-T$_{PHO5}$ | |
| CSY948 | 5 | mor A morB$^{E160G}$ | P$_{GPD}$-T6ODM-T$_{ADH1}$, P$_{TEF1}$-CODM-T$_{CYC1}$, P$_{PYK1}$-morA-T$_{MFa1}$, P$_{PGK1}$-morB$^{E160G}$-T$_{PHO5}$ | |
| CSY949 | 5 | mor A$^{C81B}$ morB$^{E160G}$ | P$_{GPD}$-T6ODM-T$_{ADH1}$, P$_{TEF1}$-CODM-T$_{CYC1}$, P$_{PYK1}$-morA$^{C81S}$-T$_{MFa1}$, P$_{PGK1}$-morB$^{E160G}$-T$_{PHO5}$ | |
| CSY950 | 6 | CSY950 | P$_{GPD}$-T6ODM-$_{ADH1}$, P$_{TPI1}$-COR1.3-ER2-$_{STE2}$, P$_{TEF1}$-CODM-$_{CYC1}$ | ura3Δ::P$_{GPD}$-T6ODM-T$_{CYC1}$, his3Δ::P$_{GPD}$-CODM-T$_{CYC1}$, leu2Δ::P$_{GPD}$-CODM-T$_{CYC1}$ |
| CSY951 | 6 | CSY951 | P$_{GPD}$-T6ODM-T$_{ADH1}$, P$_{TEF1}$-CODM-T$_{CYC1}$, P$_{PYK1}$-morA-T$_{MFa1}$, P$_{PGK1}$-morB$^{E160G}$-T$_{PHO5}$ | ura3Δ::P$_{GPD}$-T6ODM-T$_{CYC1}$, his3Δ::P$_{GPD}$-CODM-T$_{CYC1}$, leu2Δ::P$_{GPD}$-CODM-T$_{CYC1}$ |
| CSY952 | 6 | CSY952 | P$_{GPD}$-T6ODM-T$_{ADH1}$, P$_{PGK1}$-morB-T$_{PHO5}$ | ura3Δ::P$_{GPD}$-T6ODM-T$_{CYC1}$, his3Δ::P$_{GPD}$-T6ODM-T$_{CYC1}$ |

Abbreviations: P promoter, T terminator.
CSY907 is repeated in this table to sow its use as a control strain.

Methods

As summarized above, aspects of the invention include methods of preparing a benzylisoquinoline alkaloid (BIA) of interest. As such, aspects of the invention include culturing a host cell under conditions suitable for protein production such that the heterologous coding sequences are functionally expressed and convert starting compounds of interest into product BIAs of interest.

In some instances, the method is a method of preparing a benzylisoquinoline alkaloid (BIA), include culturing a host cell (e.g., as described herein) under conditions suitable for protein production; adding a starting compound to the cell culture; and recovering the BIA from the cell culture.

In some embodiments of the method, the starting compound, BIA product and host cell are described by one of the entries of Table 1. In certain embodiments, the host cell is described by one of the strains of Table 4. In certain embodiments, the host cell comprises one or more heterologous coding sequences for one or more enzymes described in Table 2.

Any convenient methods of culturing host cells may be employed for producing the BIAs of interest. The particular protocol that is employed may vary, e.g., depending on host cell, the heterologous coding sequences, the desired BIAs, etc. The cells may be present in any convenient environment, such as an environment in which the cells are capable of expressing one or more functional heterologous enzymes. In vitro, as used herein, simply means outside of a living cell, regardless of the location of the cell. As used herein, the term in vivo indicates inside a cell, regardless of the location of the cell. In some embodiments, the cells are cultured under conditions that are conducive to enzyme expression and with appropriate substrates available to allow production of BIAs in vivo. In some embodiments, the functional enzymes can be extracted from the host for production of BIAs under in vitro conditions. In some instances, the host cells can be placed back into a multicellular host organism. The host cells can be in any phase of growth, including, but not limited to, stationary phase and log-growth phase, etc. In addition, the cultures themselves may be continuous cultures or they may be batch cultures.

Any convenient cell culture conditions for a particular cell type may be utilized. In certain embodiments, the host cells that comprise the various heterologous coding sequences can be cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids can be grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells can be grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory. Culture volumes can also be scaled up for growth in larger fermentation vessels, for example, as part of an industrial process.

Any convenient codon optimization techniques for optimizing the expression of heterologous polynucleotides in host cells may be adapted for use in the subject host cells and methods, see e.g., Gustafsson, C. et al. (2004) *Trends Biotechnol,* 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., a mM to μM amount such as between about 1-5 mM of starting compound. It is understood that the amount of starting material added, the timing and rate of addition, the form of material added, etc., may vary according to a variety of factors. The starting material may be added neat or pre-dissolved in a suitable solvent (e.g., cell culture media, water or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

The subject methods may also include recovering the BIA from the cell culture. Any convenient methods of separation and isolation (e.g., chromatography methods or precipitation methods) may be adapted for use in the subject methods to recover the BIA of interest from the cell culture. Filtration methods may be used to separate soluble from insoluble fractions of the cell culture. In some cases, liquid chromatography methods (e.g., reverse phase HPLC, size exclusion, normal phase chromatography) are used to separate the BIA from other soluble components of the cell culture.

Also included are methods of engineering host cells for the purpose of producing BIAs of interest. Inserting DNA into host cells may be achieved using any convenient methods. The methods are used to insert the heterologous coding sequences into the host cells such that the host cells functionally express the enzymes and convert starting compounds of interest into product BIAs of interest.

Any convenient promoters may be utilized in the subject host cells and methods. The promoters driving expression of the heterologous coding sequences may be constitutive promoters or inducible promoters, provided that the promoters can be active in the host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the *B. subtilis* tsr gene (encoding fructose bisphosphate aldolase) or GAPDH promoter from yeast *S. cerevisiae* (coding for glyceraldehyde-phosphate dehydrogenase), the ADH1 promoter of baker's yeast, the phosphate-starvation induced promoters such as the PHO5 promoter of yeast, the alkaline phosphatase promoter from *B. licheniformis*, yeast inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-α promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as a factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, e.g., *E. coli*. One can also use promoter selection to optimize transcript, and hence, enzyme levels to maximize production while minimizing energy resources.

Any convenient vectors may be utilized in the subject host cells and methods. Vectors of interest include vectors for use in yeast and other cells. Yeast vectors can be broken up into 4 general categories: integrative vectors (Yip), autonomously replicating high copy-number vectors (YEp), autonomously replicating low copy-number vectors (YCp) and vectors for cloning large fragments (YACs). Vector DNA can be introduced into prokaryotic or eukaryotic cells via any convenient transformation or transfection techniques.

Utility

The host cells and methods of the invention, e.g., as described above, find use in a variety of applications. Applications of interest include, but are not limited to: research applications and therapeutic applications. Methods of the invention find use in a variety of different applications including any convenient application where the production of BIAs is of interest.

The subject host cells and methods find use in a variety of therapeutic applications. Therapeutic applications of interest include those applications in which the preparation of pharmaceutical products that include BIAs is of interest. As such, the subject host cells find use in the supply of therapeutically active BIAs or precursors thereof. In some instances, the host cells and methods are used to produce commercial scale amounts of BIAs where chemical synthesis of these compounds is low yielding and not a viable means for large-scale production. In certain cases, the host cells and methods are utilized in a fermentation facility that would comprise bioreactors (fermenters) of e.g., 5,000-200,000 liter capacity allowing for rapid production of BIAs of interest for therapeutic products. Such applications may include the industrial-scale production of BIAs of interest from fermentable carbon sources such as cellulose, starch, and free sugars.

The subject host cells and methods find use in a variety of research applications. The subject host cells and methods may be used to analyze the effects of a variety of enzymes on the biosynthetic pathways of a variety of BIAs of interest. In addition, the host cells may be engineered to produce BIAs that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards BIAs of interest, or precursors thereof. In certain cases, research applications include the production of precursors for therapeutic molecules of interest that can then be further chemically modified or derivatized to desired products or for screening for increased therapeutic activities of interest. In some instances, host cell strains are used to screen for enzyme activities that are of interest in such pathways, which may lead to enzyme discovery via conversion of BIA metabolites produced in these strains.

The subject host cells and methods may be used to as a production platform for plant specialized metabolites.

The subject host cells and methods may be used as a platform for drug library development as well as plant enzyme discovery. For example, the subject host cells and methods may find use in the development of natural product based drug libraries by taking yeast strains producing interesting scaffold molecules, such as protopine, and further functionalizing the compound structure through combinatorial biosynthesis or by chemical means. By producing drug libraries in this way, any potential drug hits are already associated with a production host that is amenable to large-scale culture and production. As another example, these subject host cells and methods can be find use in plant enzyme discovery. The subject host cells provide a clean background of defined metabolites to express plant EST libraries to identify new enzyme activities. The subject host cells and methods provide expression methods and culture conditions for the functional expression and increased activity of plant enzymes in yeast.

Kits and Systems

Aspects of the invention further include kits and systems, where the kits and systems may include one or more components employed in methods of the invention, e.g., host cells, starting compounds, heterologous coding sequences, vectors, culture medium, etc., as described herein. In some embodiments, the subject kit includes a host cell (as described herein), and one or more components selected from a starting compounds, a heterologous coding sequence and/or a vector including the same, and a culture medium.

Any of the components described herein may be provided in the kits, e.g., host cells comprising one or more heterologous coding sequences, starting compounds, components suitable for use in expression systems (e.g., cells, cloning vectors, multiple cloning sites (MCS), bi-directional promoters, an internal ribosome entry site (IRES), etc.), culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

In some cases, the kit includes a host cell selected from a reticuline-producing host cell, a sanguinarine precursor-producing host cell, a protoberberine-producing host cell, a thebaine-producing host cell and an opiate-producing host cell. The host cells may include one or more heterologous coding sequences (e.g., as described herein). In certain cases, the cell expresses a BIA of interest (e.g., as described herein).

Aspects of the invention include systems for producing a BIA of interest, where the systems may include engineered host cells including heterologous coding sequences (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of BIA compounds produced by the fermented host cells. In certain embodiments, one or more starting compounds (e.g., as described herein) are added to the system, under conditions by which the engineered host cells in the fermenter produce one or more desired BIA products. In certain cases, the BIA products of interest are opioid products, such as codeine, neopine, morphine, neomorphine, hydrocodone, oxycodone, hydromorphone, dihydrocodeine, 14-hydroxycodeine, or dihydromorphine.

In some cases, the system includes means for monitoring and or analyzing one or more BIA compounds produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to BIA products of interest is complete, the fermentation may be halted and purification of the BIA products may be done. As such, in some cases, the subject system includes a purification component suitable for purifying the BIA products of interest from the host cell medium into which it is produced. The purification component may include any convenient means may be used to purify the BIA products of fermentation, including but not limited to, silica chromatography, reverse-phase chromatography, ion exchange chromatography, HIC chromatography and size exclusion chromatography. In some cases, the subject system provides for the production and isolation of BIA fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

I. Reticuline-producing Yeast Strains

Strains of S. cerevisiae were developed with improved reticuline production through overexpression of 6OMT, CNMT or 4'OMT genes from several different species.

FIG. 1 depicts the in vivo methylation of norlaudanosoline by methyltransferases from P. somniferum and T. flavum. In each panel, cultures of host cells expressing each methyltransferase individually were grown in the presence of norlaudanosoline and methylation products were detected with LCMS. The data demonstrate that methyltransferases have broad substrate specificity providing support to alternative methylation pathways. (a) 6OMT enzymes from both species show similar methylation activity on norlaudanosoline. Fragmentation of methylation product shown in inset. (b) PsCNMT displays higher methylation activity than TfCNMT on norlaudanosoline as a substrate. Fragmentation of methylation product shown in inset. (c) 4'OMT enzymes from both species show similar methylation activity on norlaudanosoline. Fragmentation of methylation product is shown in inset.

Figure 2:
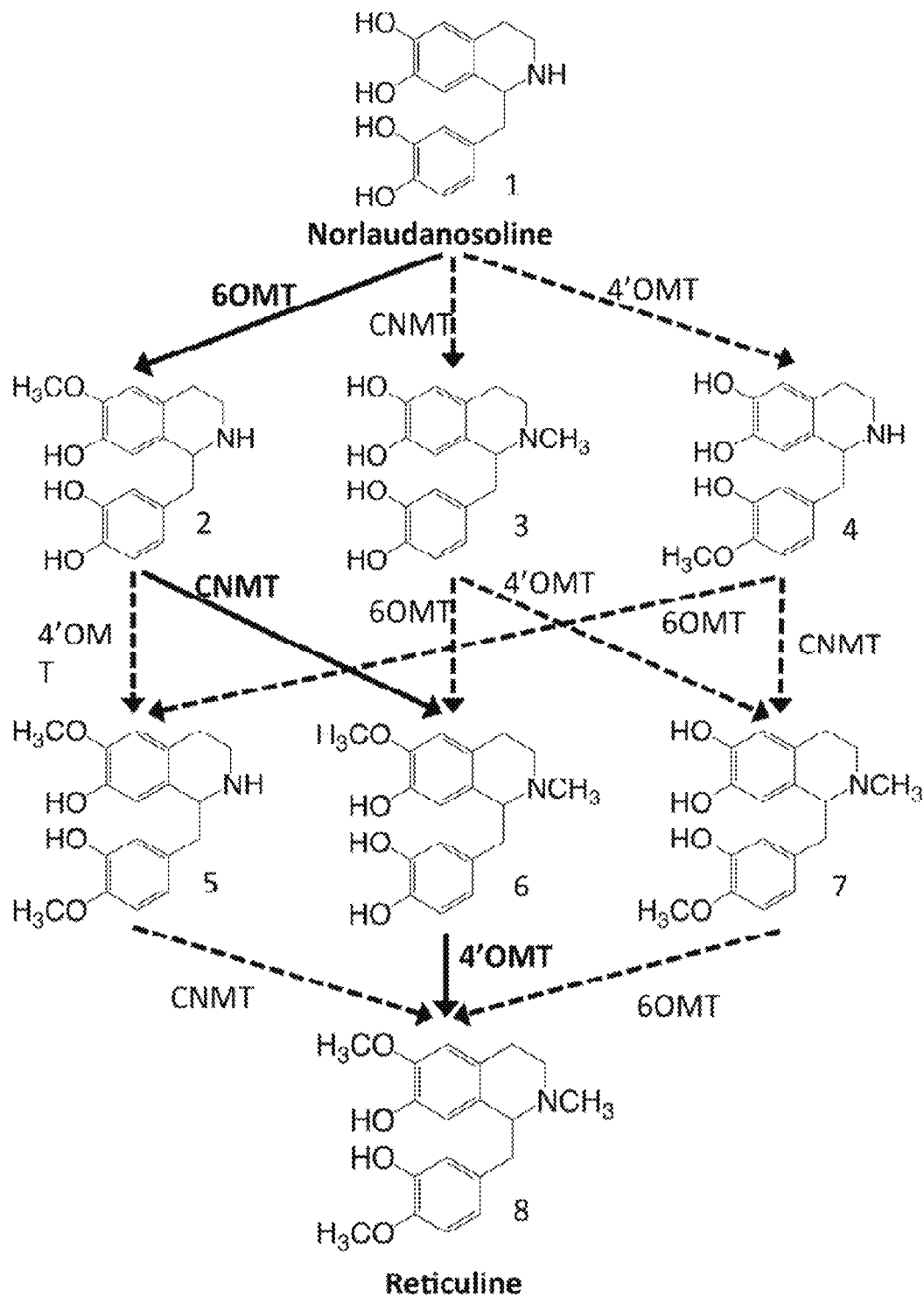
FIG. 2 depicts alternative methylation routes to reticuline from norlaudanosoline.

FIG. 2 depicts alternative methylation routes to reticuline from norlaudanosoline. When the starting material of the pathway is norlaudanosoline (1), 6OMT, CNMT or 4'OMT can act on this compound, thereby creating three distinctly methylated intermediates. BIA 2, which is initially methylated by 6OMT, can then be methylated by either CNMT or 4'OMT. Likewise, BIA 3, which is initially methylated by CNMT, can then be methylated by either 6OMT or 4'OMT. Similarly, BIA 4, which is initially methylated by 4'OMT, can then be methylated by either 6OMT or CNMT. BIA 5, which is previously methylated by 6OMT and 4'OMT, can be methylated by CNMT to produce reticuline. BIA 6, which is previously methylated by 6OMT and CNMT, can be methylated by 4'OMT to produce reticuline. BIA 7, which is previously methylated by CNMT and 4'OMT, can be methylated by 6OMT to produce reticuline.

Figure 3:
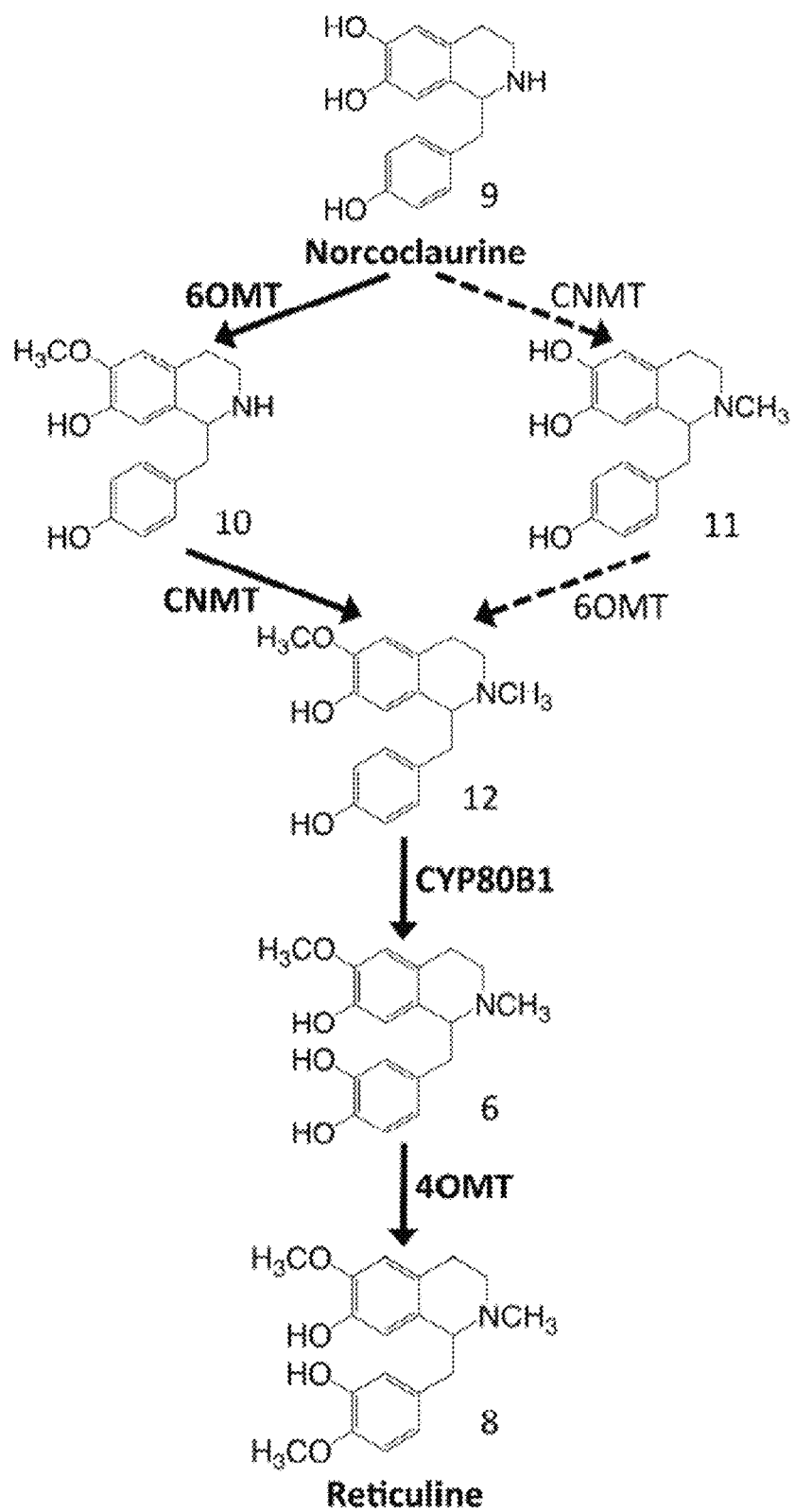
FIG. 3 depicts alternative methylation routes to reticuline from norcoclaurine.

FIG. 3 depicts alternative methylation routes to reticuline from norcoclaurine. When the starting material of the pathway is norcoclaurine, either 6OMT or CNMT can act on this compound, thereby creating two distinctly methylated products. BIA 10, which is initially methylated by 6OMT, can then be methylated by CNMT. BIA 11, which is initially methylated by CNMT, can then be methylated by 6OMT. BIA 12, also known as N-methylcoclaurine, which is previously methylated by 6OMT and CNMT, is then sequentially acted upon by CYP80B1 and 4'OMT to produce reticuline.

N-methylcoclaurine production: expression titration of PsCNMT. The measurement of N-methylcoclaurine (BIA 12) production when PsCNMT gene copy number is varied with either Tf6OMT or Ps6OMT in a strain fed norcoclaurine was performed. N-methylcoclaurine (BIA 12) production is shown when PsCNMT gene copy number is varied with either Tf6OMT or Ps6OMT in a strain fed norcoclaurine. Crude cell lysates of host cells expression either Ps6OMT or Tf6OMT and one or two copies of PsCNMT were incubated with norcoclaurine. The doubly methylated product, N-methylcoclaurine, was measured using LCMS. With Ps6OMT, the ion count increased from $2 \times 10^7$ to $5.5 \times 10^7$ when 2×PsCNMT used instead of 1×PsCNMT. With Tf6OMT, the ion count increased from $1.5 \times 10^7$ to $6 \times 10^7$ when 2×PsCNMT used instead of 1×PsCNMT. The data demonstrates that higher gene copy number of a methyltransferase CNMT can increase N-methylcoclaurine production.

II. Sanguinarine Precursor-producing Yeast Strains

Strains were developed that produce protoberberine and benzophenanthridine alkaloids, including cheilanthifoline, stylopine, cis-N-methylstylopine, protopine and dihydrosanguinarine.

FIG. 4 depicts a synthetic pathway present in the host cells to make sanguinarine from reticuline. Although the pathway may be longer, starting from norlaudanosoline or norcoclaurine as shown in other figures, this particular pathway depiction begins with reticuline and ends with sanguinarine. The pathway can include fewer enzymes than those displayed if the desired end result is one of the intermediates in the norlaudanosoline to sanguinarine pathway. The addition of multiple enzymatic steps, specifically those catalyzed by the enzymes CFS, STS, TNMT, MSH, P6H and DBOX, within an engineered yeast strain produces a variety of protoberberine and benzophenanthridine compounds.

1. Introduction

Figure 11:
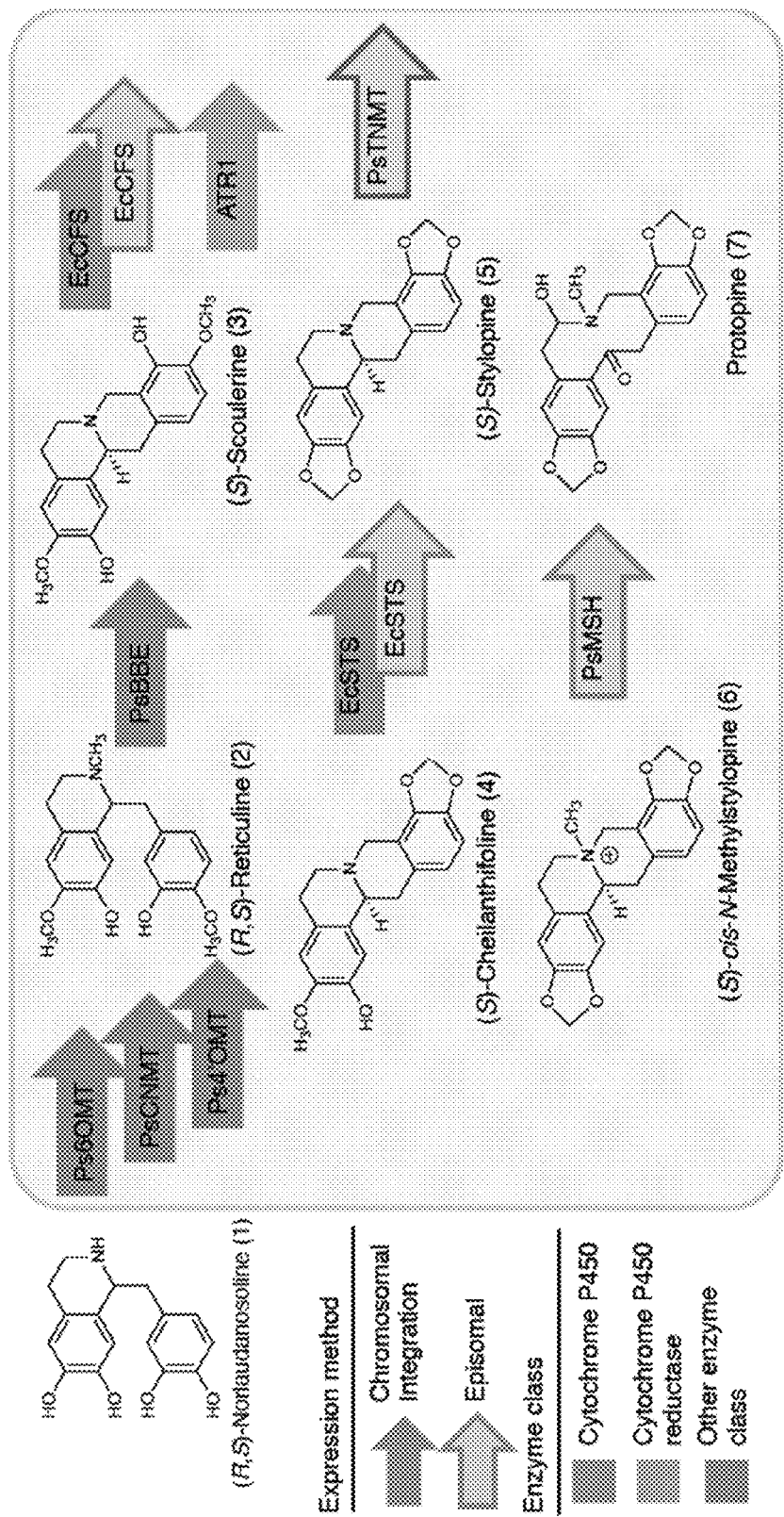
FIG. 11 depicts a route for engineering protoberberine and protopine alkaloid biosynthesis in *S. cerevisiae* from the precursor molecule norlaudanosoline via the branch point intermediate reticuline. The final engineered protopine production strain contains 11 heterologous expression cassettes (seven integrated enzymes and four enzymes expressed from a yeast artificial chromosome), including Cytochrome P450s (EcSTS, PsMSH, EcCFS), Cytochrom P450 reductases (ATR1) and other enzyme class (Ps6OMT, PsCNMT, Ps4'OMT, PsBBE, PsTNMT).

Microbial production hosts have been engineered for several protoberberine and protopine alkaloids in the sanguinarine branch of the BIA biosynthetic pathway. Specifically, yeast strains were engineered to produce the compounds cheilanthifoline (4), stylopine (5), (S)-cis-N-methylstylopine (6), and protopine (7) from the fed substrate norlaudanosoline (1) (FIG. 11). These pathways show complex plant natural products pathways reconstructed in a microbial host, based on number of heterologous enzymes and types of enzymes. In particular, a pathway comprising eight enzymatic steps, including three catalyzed by cytochrome P450s, and 11 total heterologous expression cassettes, was demonstrated. Several pathway optimization strategies were developed for the reconstruction of these complex pathways in yeast for an efficient microbial platform for the biosynthesis of plant specialized metabolites. In particular, strategies supporting the functional expression of multiple plant cytochrome P450 enzymes in the context of a large multi-step pathway were used, including expression balancing, CPR matching, and culture condition optimization. These general design strategies can be applied more broadly to support the engineering of diverse plant natural product pathways in yeast.

FIG. 11 depicts engineering protoberberine and protopine alkaloid biosynthesis in *S. cerevisiae*. The optimized protopine production strain is fed the precursor molecule norlaudanosoline, which is converted to the key branch point intermediate reticuline by three chromosomally integrated methyltransferase enzymes (Ps6OMT, PsCNMT, Ps4'OMT). Chromosomally integrated berberine bridge enzyme (PsBBE) transforms (S)-reticuline to (S)-scoulerine. Two copies (one chromosomally integrated, one expressed from a yeast artificial chromosome) of the cytochrome P450s cheilanthifoline synthase (EcCFS) and stylopine synthase (EcSTS) are expressed with a chromosomally integrated copy of a cytochrome P450-NADPH reductase from *A. thaliana* (ATR1) to produce the compounds (S)-cheilanthifoline and (S)-stylopine, respectively. Next, tetrahydroprotoberberine-N-methyltransferase (PsTNMT) converts (S)-stylopine to (S)-cis-N-methylstylopine, then the cytochrome P450 cis-N-methylstylopine 14-hydroxylase (PsMSH) produces protopine from cis-N-methylstylopine. Both PsTNMT and PsMSH were expressed from a yeast artificial chromosome. The final engineered protopine production strain contains 11 heterologous expression cassettes (seven integrated enzymes and four enzymes expressed from a yeast artificial chromosome). Cytochrome P450s (EcSTS, PsMSH, EcCFS), Cytochrome P450 reductases (ATR1), other enzyme class (Ps6OMT, PsCNMT, Ps4'OMT, PsBBE, PsTNMT).

2. Results a. Engineering an Optimized Microbial Scaffold-producing Strain for the Protoberberine and Protopine Alkaloids The reconstruction of the sanguinarine branch of the BIA biosynthetic pathway was targeted, which encompasses several protoberberine and protopine alkaloids, in a yeast production host. The sanguinarine branch is comprised of ten enzymatic steps, four of which are catalyzed by plant cytochrome P450s, to reach sanguinarine (the end-product of the pathway) from norlaudanosoline (a commercially-available, fed substrate). Several downstream enzymes in this pathway have been cloned and characterized, allowing the engineering of a microbial production strain for intermediate metabolites along the sanguinarine branch.

The BIA metabolite scoulerine is a scaffold from which one can access the protoberberine and protopine alkaloid structures in the sanguinarine branch. A yeast strain that had been previously engineered to produce scoulerine from the fed substrate norlaudanosoline was used (Hawkins, K. & Smolke, C. Production of benzylisoquinoline alkaloids in *Saccharomyces cerevisiae*. Nat. Chem. Biol. 4, 564-573 (2008)). This strain expressed four plant enzymes; the three methyltransferase (Papaver somniferum norcoclaurine 6-O-methyltransferase, Ps6OMT; *P. somniferum* coclaurine-N-methyltransferase, PsCNMT; *P. somniferum* 3' hydroxy-N-methylcoclaurine 4'-O-methyltransferase, Ps4'OMT) expression cassettes were integrated into the chromosome, and the expression cassette encoding the enzyme that converts the key branch point metabolite reticuline to the scaffold scoulerine (*P. somniferum* berberine bridge enzyme, PsBBE) was placed into a high-copy plasmid.

To optimize the strain for greater flux through the sanguinarine branch, scoulerine production was increased by integrating the PsBBE expression cassette into the yeast chromosome. The strains were fed 4 mM norlaudanosoline and grown for 96 hours. Samples of the growth media were analyzed using high pressure liquid chromatography coupled to mass spectrometry (LC-MS) and production of scoulerine was confirmed by comparison of the fragmentation pattern (MS-MS) to reported fragmentation patterns (Schmidt, J. & Raith, K. Analysis of benzylisoquinoline-type alkaloids by electrospray tandem mass spectrometry and atmospheric pressure photoionization. Eur. J. Mass Spectrom. 11, 325-333 (2005)). By changing expression of PsBBE from a high-copy plasmid to the chromosome, the production of scoulerine was increased by 3-fold to 1.5 mg/L and improved the conversion efficiency of reticuline to scoulerine from 20% to 64%.

b. Engineering an Optimized Microbial Production Host for Cheilanthifoline

The first dedicated step in the sanguinarine branch is the conversion of the scaffold molecule scoulerine to cheilanthifoline by the enzyme cheilanthifoline synthase (CFS), the first cytochrome P450 in this pathway (FIG. 12a). As plant cytochrome P450s have been a challenge to functionally express in microbial hosts, various strategies were examined to support functional heterologous expression of this P450 enzyme and optimize its activity in yeast.

The pairing of various plant cytochrome CPRs with CFS variants expressed at different levels was first examined. Variants of CFS from three native plant hosts were codon optimized and synthesized—E. californica (EcCFS), A. mexicana (AmCFS), and P. somniferum (PsCFS). The CFS variants were expressed on either a high-copy or low-copy plasmid from a strong yeast promoter (pGPD). Three plant CPR expression cassettes, encoding A. thaliana (ATR1), E. californica (EcCPR), and P. somniferum (PsCPR)CPRs, were integrated into the yeast chromosome and tested with each of the CFS variants. Although EcCPR and PsCPR originate from the same plant species as the CFS variants, plants have multiple CPR variants and the particular CPRs selected may not support CFS activity. While ATR1 originates from a plant species that does not produce BIA molecules, this CPR has been used to support heterologous P450 activity in yeast (Urban, P., Mignotte, C., Kazmaier, M., Delorme, F. & Pompon, D. Cloning, yeast expression, and characterization of the coupling of two distantly related Arabidopsis thaliana NADPH-cytochrome P450 reductases with P450 CYP73A5. J. Biol. Chem. 272, 19176-86 (1997)). Strains harboring all combinations of CPR variants and CFS variants were fed 2 mM norlaudanosoline and grown for 96 hours. Samples of the growth media were analyzed using LC-MS. Cheilanthifoline production was confirmed through comparison of the observed fragmentation pattern to reported fragmentation patterns (FIG. 12b).

The data demonstrates that the specific CPR pairing and P450 expression level can substantially impact the functional activity of the plant P450 in a heterologous microbial host. Specifically, ATR1 supported activity of all CFS variants was 20-50 fold better than any of the other tested CPR variants and produced up to 600 μg/L cheilanthifoline (FIG. 12c). While the native yeast CPR and EcCPR were able to support a low level of activity from EcCFS and AmCFS, the PsCPR did not couple with any of the expressed P450s. All CFS variants resulted in cheilanthifoline production when paired with an appropriate CPR; however, EcCFS and AmCFS were substantially more active than PsCFS. The difference in activity observed between the EcCFS and AmCFS variants in yeast is supported by the difference in the reported $K_m$ values for these enzymes (EcCFS, 900 nM; AmCFS, 1.9 NM; PsCFS, no reported $K_m$). The data also demonstrates that cheilanthifoline production levels were substantially higher when the CFS variants were expressed from low-copy plasmids than when expressed from high-copy plasmids.

P450s naturally localize to the endoplasm reticulum (ER), and overexpression of these enzymes in yeast can cause a stress response in which the ER membranes proliferate. The activity data, suggests that high-level expression of plant P450s in yeast can overwhelm the ER and impair the activity of the enzymes. To examine P450 concentration and subcellular localization as a function of expression level in live cells, the CFS variants were C-terminally tagged with EGFP in high-copy and low-copy plasmids and cells harboring these constructs were analyzed by confocal microscopy. ER localization of the tagged enzymes was confirmed by co-localization with the ER marker DsRed-Kar2-HDEL (FIG. 12d).

Two major differences were observed between the cells expressing the tagged CFS variants from high-copy or low-copy plasmids. First, a significant reduction in the number of GFP positive cells was observed in cells harboring a P450-GFP fusion construct compared to a GFP-only construct, and the difference was more significant when the fusion was expressed from a high-copy plasmid (27%) than from a low-copy plasmid (56%). The data suggest that the cell's ability to maintain a plasmid expressing a cytochrome P450 enzyme is reduced in comparison to a plasmid expressing a fluorescent reporter, and that expression of plant P450s from low-copy plasmids results in more stable expression across the cell population and thus may result in higher bulk activity. Second, the morphology of the ER was distinct between cells harboring the P450-GFP expression cassettes in high- and low-copy plasmids. In cells harboring the high-copy plasmids, the P450-GFP fusion proteins were generally observed in highly concentrated bright patches adjacent to the nucleus or plasma membrane. In contrast, in cells harboring the low-copy plasmids, the ER membranes remained distributed throughout the cell and GFP fluorescence levels were dim, indicating a lower concentration of P450s. Thus, under conditions in which the plant P450 was expressed at lower levels the morphology of the ER membrane in these engineered cells was more similar to that of wild type cells. Taken together, the confocal microscopy and functional activity data suggest that high-level expression of plant P450s can cause extreme ER proliferation, which is highly stressful to the yeast host and is detrimental to the activity of the enzyme. Thus, the optimal expression strategy for plant P450s in a heterologous yeast host is from low-copy plasmids or stable integrations into the chromosome (FIG. 12e).

Finally, the impact of plant P450 expression level and regulation on cheilanthifoline production in the yeast host was examined. Cheilanthifoline production was examined from engineered pathway variants in which CFS was expressed in a low-copy plasmid under the control of five different promoters: pGPD (level: strong, regulation: early), pTEF1 (strong, constitutive), pPGK1 (medium, early), pTPI1 (medium, early), and pHXT7 (strong, late). As before, strains harboring the indicated constructs were fed 2 mM norlaudanosoline and grown for 96 hours at the indicated conditions. Samples of the growth media were analyzed with LC-MS. The GPD promoter provided up to a 12-fold improvement in cheilanthifoline production compared to the other promoters tested (FIG. 12f). The data indicate that both expression level and regulation strategy play roles in optimizing the activity of plant P450s in a heterologous yeast host. For example, the TEF promoter exhibits similar strength as pGPD, with a different regulatory profile and pPGK1 exhibits a similar regulatory profile as pGPD with a different strength; however, each of these promoters resulted in different cheilanthifoline production levels. These results indicate that an optimized cheilanthifoline-producing yeast strain was engineered to express the plant P450 EcCFS at low levels (either from a low-copy plasmid or chromosomally integrated under the control of a GPD promoter) and to pair this plant P450 with the ATR1 CPR. This engineered strain produced up to 600 μg/L cheilanthifoline and was able to convert up to 38% of the scoulerine.

Figure 12:
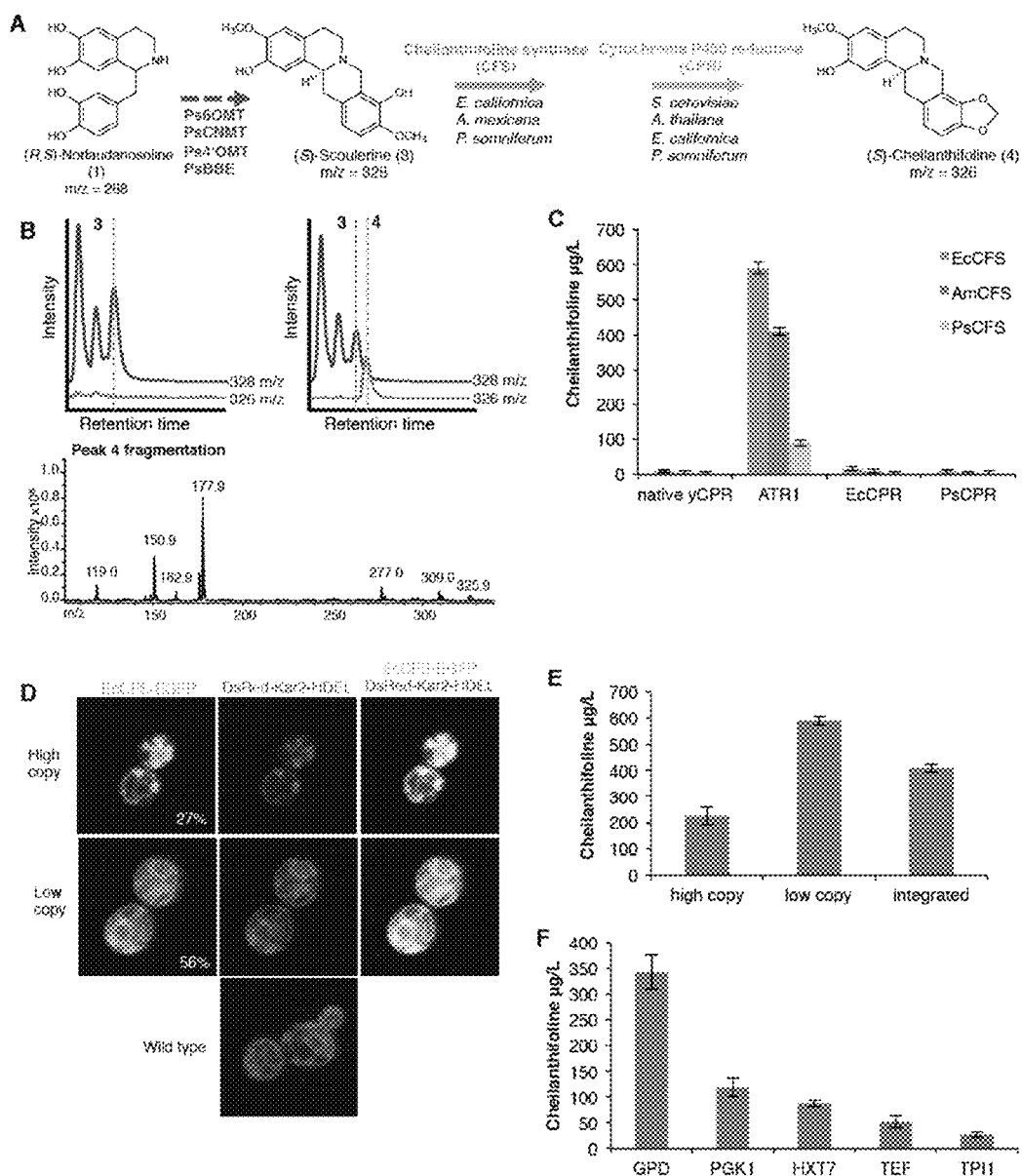
FIG. 12 depicts the microbial production of (S)-cheilanthifoline. (a) Schematic depicting the transformation of norlaudanosoline to (S)-cheilanthifoline. (b) LC-MS analysis of growth media of yeast strains fed with norlaudanosoline, showing the vector control strain (left) produces scoulerine (peak 3, m/z=328). When the EcCFS enzyme is expressed (right), the metabolite cheilanthifoline is detected (m/z=326, peak 4), confirmed by MS-MS fragmentation (below). (c) (S)-cheilanthifoline production with various enzyme variant and cytochrome P450 NADPH reductase partner pairing. (d) P450 expression level results in distinct ER morphology. EcCFS C-terminally tagged with GFP on high copy (top) or low copy (middle) plasmids localize to the endoplasmic reticulum, but show distinct morphologies of ER proliferation. Wild type ER (no heterologous P450 expressed) is shown for comparison (bottom). Percentages indicate GFP positive proportion of the yeast. (e) Stable expression of CFS improves cheilanthifoline production and conversion efficiency of scoulerine. (f) Promoter choice affects CFS activity. EcCFS expressed from a low copy plasmid with URA selection under the control of 5 different promoters.

FIG. 12 depicts microbial production of (S)-cheilanthifoline. (a) Schematic depicting the transformation of norlaudanosoline to (S)-cheilanthifoline with an emphasis on the enzymatic steps optimized. Dashed arrows indicate multiple enzymatic steps. Scheme labels follows that depicted in FIG. 11. (b) LC-MS analysis of growth media of yeast strains fed 2 mM norlaudanosoline and grown for 96 hours. LC-MS traces show the vector control strain (left) produces scoulerine (peak 3) but no peak in 326 EIC. When the EcCFS enzyme is expressed (right), a peak is detected in the 326 EIC (peak 4), and the fragmentation (MS-MS, below) confirms the identity of the metabolite as cheilanthifoline. (c) (S)-cheilanthifoline production is dependent on enzyme variant and cytochrome P450 NADPH reductase partner pairing. Variants of cheilanthifoline synthase (CFS) from *E. californica* (EcCFS), *A. mexicana* (AmCFS) and *P. somniferum* (PsCFS) were expressed from low copy plasmids in yeast strains with cytochrome P450 reductase enzymes (CPRs) from either the native yeast or various plant sources (*A. thaliana*, *E. californica*, *P. somniferum*) integrated into the TRP locus. (d) P450 expression level results in distinct ER morphology. EcCFS C-terminally tagged with GFP on high copy (top) or low copy (middle) plasmids localize to the endoplasmic reticulum, but show distinct morphologies of ER proliferation. Wild type ER (no heterologous P450 expressed) is shown for comparison (bottom). Percentages indicate proportion of the yeast population that are GFP positive under the indicated expression condition. (e) Stable expression (low copy plasmid or chromosomal integration) of CFS improves cheilanthifoline production and conversion efficiency of scoulerine. EcCFS was expressed either on a high copy plasmid (2 micron, TRP selection marker), low copy plasmid (CEN/ARS, TRP selection marker), or integrated into the MET15 locus of the yeast chromosome. (f) Promoter choice affects CFS activity. EcCFS was expressed form a low copy plasmid with URA selection under the control of 5 different promoters (GPD, HXT7, PGK1, TEF, TPI1). Data in (c, d) are representative of at least 3 independent experiments, and data in (e, f) are reported as mean±s.d. of at least 3 independent experiments.

c. Engineering an Optimized Microbial Production Host for Stylopine

Figure 13:
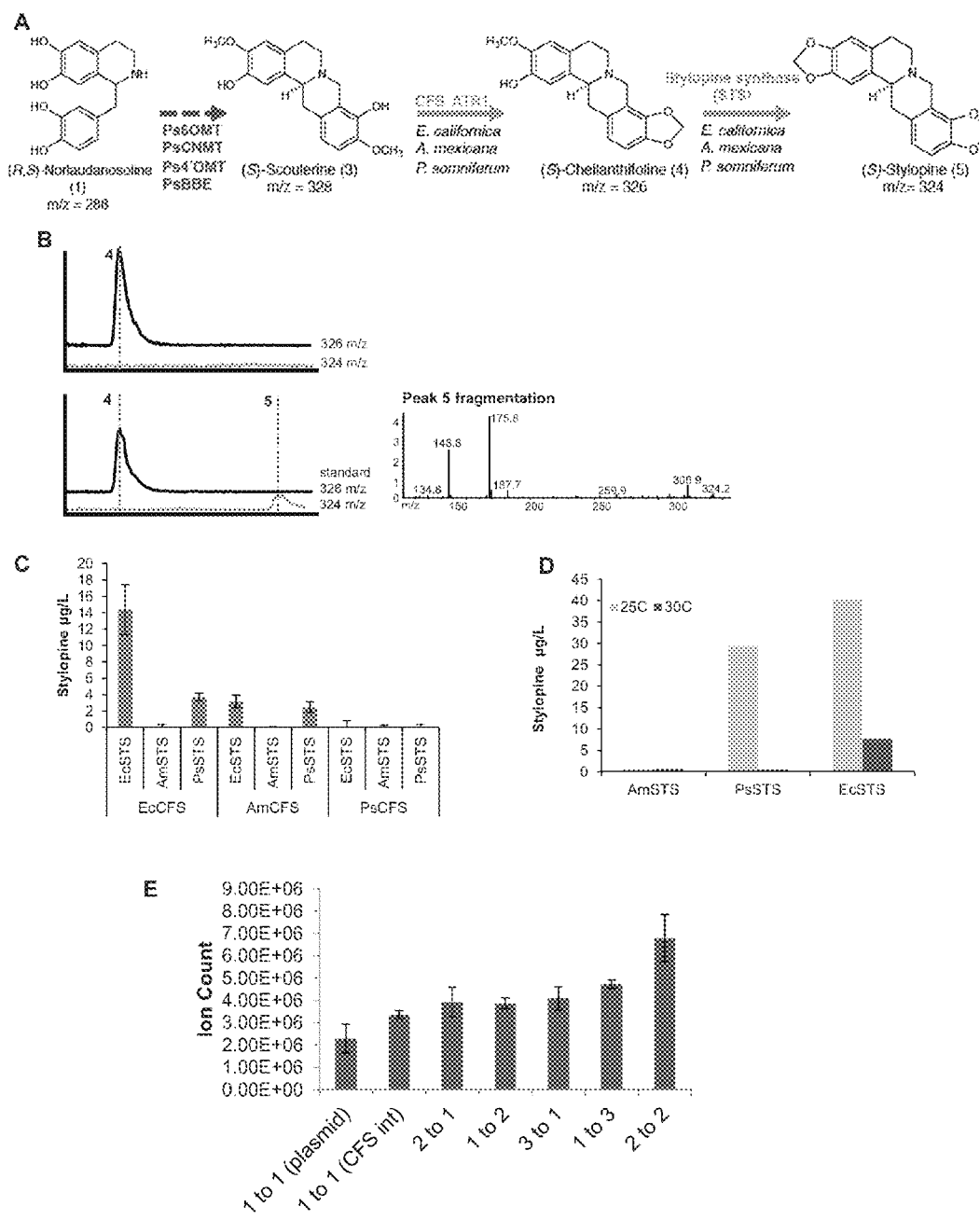
FIG. 13 depicts optimization of (S)-stylopine production. (A) Schematic depicting the transformation of norlaudanosoline to (S)-stylopine. (B) LC-MS analysis of growth media of yeast strains fed 2 mM norlaudanosoline, showing vector control strain produces cheilanthifoline (peak 4, m/z=326). When the EcSTS enzyme is expressed, stylopine is detected (peak 5, m/z=324) by comparison to standard. (C) Stylopine production varies with the combination of the species variants of CFS and STS, expressed from separate low copy plasmids. (D) Growth of the engineered yeast strains at 25° C. improves STS activity. (E) Gene copy number of CFS and STS affects stylopine production.

The next step in the sanguinarine branch is the conversion of cheilanthifoline to stylopine by stylopine synthase (STS), a plant cytochrome P450 closely related to CFS (FIG. 13). As a starting point in engineering stylopine-producing strains, the P450 optimization strategies elucidated with CFS were utilized; specifically, (i) expressing the plant P450 from a low-copy plasmid, (ii) controlling the expression of the P450 from the GPD promoter, and (iii) pairing the P450 with the ATR1 CPR. However, since the biosynthetic pathway to stylopine includes two plant P450s, additional strategies were examined for further optimizing the activities of these enzymes within the context of the multi-step pathway.

The pairings of plant variants of STS and CFS were first examined to explore any synergistic effects between particular pairings. Variants of STS from *E. californica* (EcSTS), *A. mexicana* (AmSTS), and *P. somniferum* (PsSTS) were yeast codon optimized and synthesized. Yeast strains with the ATR1 CPR expression cassette integrated into the chromosome and harboring different combinations of CFS and STS variants on low-copy plasmids were fed 2 mM norlaudanosoline and grown for 96 hours. Samples of the growth media were analyzed with LC-MS. Stylopine production was confirmed through comparison of the elution time and fragmentation pattern to a standard (ChromoDex) and reported fragmentation patterns (FIG. 13b). The data demonstrate that heterologous expression of both EcSTS and PsSTS result in stylopine production in the engineered yeast strains, whereas AmSTS was not active under these conditions. AmSTS is also reported to convert scoulerine to nandinine; however, this product was not detected. The most productive P450 enzyme pairing was EcCFS and EcSTS, which produced 14 µg/L stylopine, up to a 6-fold improvement over the other combinations of enzymes (FIG. 13c). The difference in activity observed between the STS variants in yeast is supported by the difference in the reported $K_m$ values for these enzymes (EcSTS, 400 nM; AmSTS, 5.2 NM; PsSTS, no reported $K_m$). However, even with the most productive P450 pairings, the conversion efficiency of cheilanthifoline to stylopine was only 25%.

Methods were next investigated to improve the conversion efficiency of cheilanthifoline to stylopine. The effect of growth temperature on plant P450 activity in our heterologous yeast host was examined. Yeast strains harboring the biosynthetic pathway with EcCFS paired with each STS variant were grown at 30° C. and 25° C. As before, strains harboring the indicated constructs were fed 2 mM norlaudanosoline and grown for 96 hours at the indicated conditions. Samples of the growth media were analyzed using LC-MS. Stylopine production in strains expressing EcCFS and EcSTS increased by 3-fold to a titer of 40 µg/L when the strains were grown at 25° C. compared to 30° C. (FIG. 13d). The data indicate the strains are more productive on a per OD basis, meaning that the improved production of stylopine is due to an increase in the bulk activity of the enzymes, not due to higher cell density. It is likely that the effects on general yeast cellular processes as a result of changing these conditions resulted in improved folding and localization of the P450s, and thus improved activities.

Varying the gene copy number ratio of CFS and STS was examined. Experiments expressing the enzymes from plasmids indicated that a 2:2 ratio of CFS to STS resulted in a 3-fold increase in stylopine production compared to a 1:1 ratio (FIG. 13e). Taken together, the data indicates that an optimized stylopine-producing yeast strain was engineered to express EcCFS and EcSTS with an optimal gene copy number ratio of 2:2 and when grown at 25° C. produced stylopine and improved the conversion efficiency of scoulerine to cheilanthifoline and the conversion of cheilanthifoline to stylopine.

FIG. 13 depicts optimization of (S)-stylopine production. (A) Schematic depicting the transformation of norlaudanosoline to (S)-stylopine with an emphasis on the enzymatic steps optimized. Dashed arrows indicate multiple enzymatic steps. Scheme labels follows that depicted in FIG. 11. (B) LC-MS analysis was performed of the growth media of yeast strains fed 2 mM norlaudanosoline and grown for 96 hours. LC-MS traces show the vector control strain produces cheilanthifoline (peak 4, m/z=326) but no peak in the m/z=324 EIC. When the EcSTS enzyme is expressed, a peak is detected in the m/z=324 EIC (peak 5), which elutes at the same time as the stylopine standard. The fragmentation of the stylopine standard (MS-MS) matches the fragmentation of peak 5, confirming the identity of the metabolite as stylopine. LC-MS traces were representative of at least three independent experiments. (C) Stylopine production varies with the combination of the species variants of CFS and STS. All pairings of CFS and STS variants were expressed from separate low copy plasmids. (D) Growth of the engineered yeast strains at 25° C. improves STS activity. Each variant of STS was expressed with EcCFS (on separate low copy plasmids) and grown at either 25° C. or 30° C. Gene copy number of CFS and STS affects stylopine production. (E)

Gene copy number was varied by integrating a copy of the EcCFS expression cassette into the chromosome in the MET15 locus and expressing additional copies of EcCFS and EcSTS on low-copy plasmids. The strain variants in this experiment all harbored three plasmids regardless of P450 copy number to ensure that plasmid load and media composition were consistent. The data demonstrate that increasing copies of the two plant P450s generally resulted in increased stylopine production. The highest stylopine production resulted from two copies of EcCFS and two copies of EcSTS, which improved production levels be approximately 3-fold compared to the original expression system (one copy of each enzyme).

d. Engineering a Microbial Production Host for (S)-cis-N-methylstylopine and Protopine The next step in the pathway is the conversion of stylopine to (S)-cis-N-methylstylopine by the enzyme tetrahydroprotoberberine-N-methyltransferase (TNMT) (FIG. 14a). TNMT was added to a YAC containing EcCFS and EcSTS, which was expressed in a strain with integrated copies of EcCFS and EcSTS. Strains harboring the indicated construct were fed 2 mM norlaudanosoline and grown for 96 hours at 25° C., and samples of the growth media were analyzed with LC-MS. The production of cis-N-methylstylopine was confirmed by comparison of the fragmentation pattern to reported fragmentation patterns (FIG. 14b). When TNMT is expressed in the optimized stylopine-producing strain, cis-N-methylstylopine is produced and stylopine cannot be detected in the media, suggesting that TNMT is highly efficient and able to reach 100% conversion efficiency.

The final step in protopine synthesis is the hydroxylation of (S)-cis-N-methylstylopine by the cytochrome P450 (S)-cis-N-methylstylopine 14-hydroxylase (MSH). The optimization techniques for cytochrome P450s were applied to MSH expression, including expression from a stable construct, in this case a YAC, and pairing with the ATR1 reductase partner. Strains harboring the indicated construct were fed 2 mM norlaudanosoline and grown for 96 hours at 25° C. Protopine production was confirmed through comparison of the elution time and fragmentation pattern to a standard and reported fragmentation patterns (FIG. 14c). The data indicates that MSH is a highly efficient enzyme, such that the optimized protopine-producing strain protopine and achieves conversion of cis-N-methylstylopine to protopine.

Figure 14:
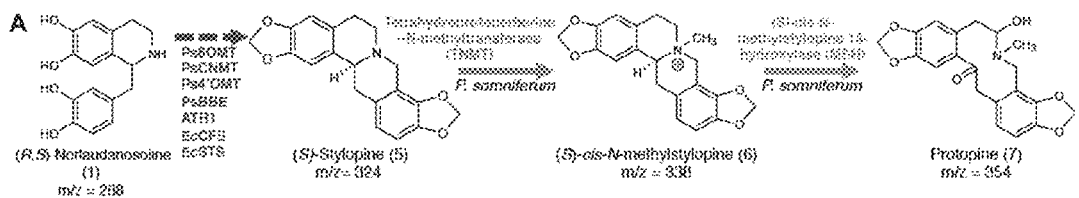
FIG. 14 depicts engineering of a heterologous protopine biosynthesis pathway. (A) Schematic depicting the transformation of norlaudanosoline to protopine. (B) LC-MS analysis of growth media of yeast strains fed 2 mM norlaudanosoline showing the vector control strain produces stylopine (peak 5, m/z=324). When the TNMT enzyme is expressed, the metabolite cis-N-methylstylopine is detected (m/z=338, peak 6) as confirmed by MS-MS fragmentation. (C) When MSH is added, protopine is detected (m/z=354), as confirmed by comparison to a standard and MS-MS fragmentation.
Figure 14:
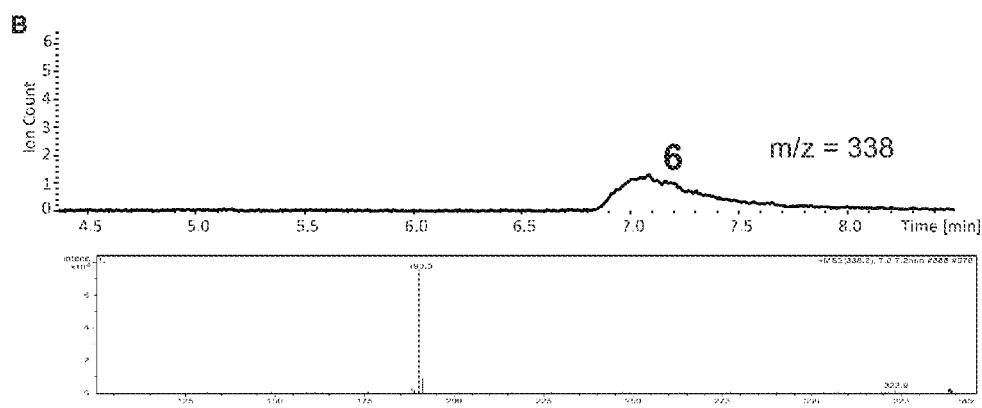
Figure 14:
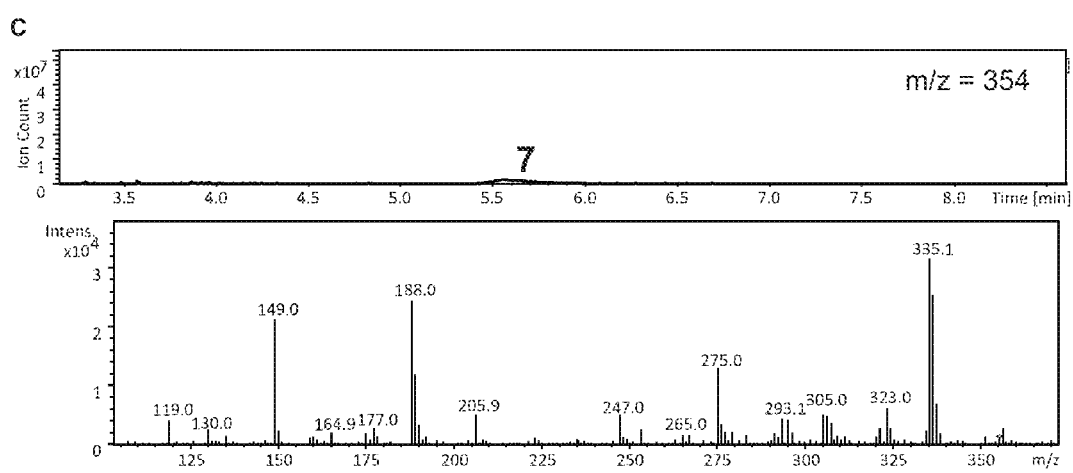

FIG. 14 depicts engineering of a heterologous protopine biosynthesis pathway. (A) Schematic depicting the transformation of norlaudanosoline to protopine with an emphasis on the enzymatic steps optimized. Dashed arrows indicate multiple enzymatic steps. Scheme labels follows that depicted in FIG. 11. (B) LC-MS analysis was performed of growth media of yeast strains fed 2 mM norlaudanosoline and grown for 96 hours. LC-MS traces showed that the vector control strain produces stylopine (peak 5, m/z=324) but no peaks in the m/z=338 or 354 EICs. When the TNMT enzyme is expressed, a peak is detected in the m/z=338 EIC (peak 6) and the fragmentation (MS-MS) confirms the identity of the metabolite as cis-N-methylstylopine. (C) When MSH is added, a peak is detected in the m/z=354 EIC, which elutes at the same time as the protopine standard and the fragmentation (MS-MS) of the protopine standard matches the fragmentation of peak 7 (m/z=354), confirming the identity of the metabolite as protopine. LC-MS traces were representative of at least three independent experiments.

5. Optimization of Culture Conditions for Protoberberine and Protopine Alkaloid Production To produce more cheilanthifoline or stylopine, yeast strains were constructed to overexpress cytochrome $b_5$ to optimize the activity of cytochrome P450s. Cytochrome $b_5$ with CFS and STS. Cheilanthifoline and/or stylopine production from host cells with and without cytochrome $b_5$ overexpressed was measured. Cultures were grown in the presence of norlaudanosoline and products were detected in the media with LCMS. The data demonstrate that in some cases the levels of cheilanthifoline (e.g., with AmCFS) and/or stylopine (e.g., with EcCFS/AmSTS) is increased when cytochrome $b_5$ is expressed.

To produce more protoberberine alkaloids the yeast strain is optimized by the deletion of genes associated with the unfolded protein response and endoplasmic reticulum (ER) proliferation to improve BIA production. Examples of gene deletions include IRE1, HAC1, OPI1, INO1, INO2, and INO3 (Table 3). Expression of cytochrome P450s induces the unfolded protein response and causes the ER to proliferate. Deletion of genes associated with these stress responses can control or reduce overall burden on the host cell and improve pathway performance.

Genes involved in the pleiotropic drug response, including ATP-binding cassette (ABC) transporters, multidrug resistance (MDR) pumps and associated transcription factors, are deleted in the host strain to reduce the export of BIA molecules into the culture medium. Examples of genes include PDR1, STB5, PDR3, PDR5, SNQ2, YOR1, TPO1, TPO2, TPO3, TPO4, PDR10, PDR11, PDR15, PDR16, PDR17, QDR1, QDR2, QDR3, FLR1, AQR1, AQR2, and CIN5.ABstract deletions include single deletions or multiple deletions in any combination.

BIA production in transporter knockouts. The measurement of reticuline, scoulerine, cheilanthifoline and stylopine production from host cells with modification of various proteins involved in transport of compounds across the cell membrane was performed: dPDR1, dPDR5, dsNQ2, dYOR1, dPDR3, dCIN5 and dPDR1 dPDR3 knockouts were compared to a WT control. Cultures were grown in the presence of norlaudanosoline and products were detected in the media with LCMS after growing for 96 hours. The data demonstrate that some modifications (e.g., deletions) produce higher levels of reticuline, scoulerine, cheilanthifoline or stylopine than others.

Genes involved in the pleiotropic drug response, including ATP-binding cassette (ABC) transporters, multidrug resistance (MDR) pumps and associated transcription factors, are placed under the control of a regulated (inducible or growth stage dependent) promoter to implement temporal control of BIA transport. One example is to put an important transporter gene under the control of a stationary phase promoter which would cause BIAs to be retained within the cell until stationary phase, thereby increasing the likelihood starting materials are converted to end products.

4. Methods a. Plasmid and Yeast Strain Construction

Oligonucleotides were synthesized using conventional methods. Cloning was performed with chemically competent E. coli (TOP10, LifeTech, F-mcrA Δ(mrr-hsdRMS-mcrBC) φ80lacZΔM15 ΔlacX74 nupG recA1 araD139 Δ(ara-leu)7697 galE15 galK16 rpsL($Str^R$) endA1 λ⁻). E. coli were cultured in Luria-Bertani media (EMD Chemicals) with appropriate antibiotic: 100 μg/mL ampicillin (EMD Chemicals) or 50 µg/mL kanamycin (EMD Chemicals). Spin columns were used to purify plasmids from *E. coli* cultures according to the manufacturer's instructions (Epoch Life Science). Sequencing was performed by Elim Biopharmaceuticals (Hayward, Calif.). The *S. cerevisiae* strains described in this work are all derived from W303α (MATα leu2-3, 112 trp1-1 can1-100 ura3-1 ade2-1 his3-11,15). A standard lithium acetate protocol was used for yeast transformations. Yeast were cultured in either YPD or appropriate synthetic drop out media for plasmid maintenance and supplemented with 2% dextrose (w/v).

Gene sequences for EcCFS (BAG75113), EcCPR (AAC05022), EcSTS (BAD98250), and AmSTS (ABR14721) were yeast codon optimized and assembled from oligonucleotides designed with DNAWorks (Hoover, D. M. & Lubkowski, J. DNAWorks: an automated method for designing oligonucleotides for PCR-based gene synthesis. Nucleic Acids Res. 30, e43 (2002)). AmCFS (ABR14722), PsCFS (ADB89213), PsSTS (ADB89214), and PsMSH (AGC92398) were yeast codon optimized and synthesized by GeneArt (Life Technologies).

Most yeast expression vectors described in this work were constructed with Gateway Cloning Technology (Life Technologies). Enzymes were PCR amplified using PfuUltraII Fusion HS DNA Polymerase (Life Technologies) or Expand High Fidelity Polymerase (Roche), cleaned up using QIAquick PCR purification kit (Qiagen) and cloned into the pENTR vector through either TOPO cloning or a BP recombination reaction using BP clonase II and the pDONR221 vector (Life Technologies). All genes were subsequently recombined into selected pAG expression vectors from the Lindquist lab (available through Addgene) (Alberti, S., Gitler, A. D. & Lindquist, S. A suite of Gateway® cloning vectors for high-throughput genetic analysis in *Saccharomyces cerevisiae*. 913-919 (2007). doi:10.1002/yea) using LR Clonase II (Life Technologies). A variety of primers and plasmid were used in this work. For the assays testing various promoters with EcCFS, pCS2238 was digested with SacI/SpeI to remove the GPD promoter and TEF1, PGK1, TPI1 or HXT7 promoters were ligated into this site using standard ligation technique Yeast artificial chromosomes (YACs) were constructed with the GeneArt Higher Order Genetic Assembly System (Life Technologies). DNA fragments were generated through PCR reactions using primers designed with the DNA Designer for Higher Order Genetic Assembly and Expand High Fidelity Polymerase (Roche). DNA fragments were cleaned with QIAquick PCR purification kit (Qiagen) and 100 ng of each DNA fragment and the linear pYES1L vector were transformed via electroporation into engineered yeast strains containing appropriate upstream enzymes. Assembled YACs were recovered from yeast cells according to the manufacturer's instructions.

For chromosomal integrations, the gene of interest was recombined into pCS2643 or pCS2644 using LR clonase II (Life Technologies), and the complete integration cassette (gene expression cassette and selection marker) was PCR amplified with the appropriate integration primers and Expand High Fidelity Polymerase (Roche) to add approximately 80 nucleotides of homology. The PCR products from two 100 µL reactions were ethanol precipitated and transformed into yeast using a standard lithium acetate procedure. Integration was verified through PCR screening across the junctions of the targeted locus and the expression cassette. The integration selection markers were flanked by loxP sites to facilitate selection marker rescue and strains were transformed with pCS277 (pSH63) which encodes expression of CRE recombinase (Güldener et al. A new efficient gene disruption cassette for repeated use in budding yeast. Nucleic Acids Res. 24, 2519-24 (1996)). The strains were grown in YPD for 36 hours with 100× back-dilutions every 12 hours then plated to single colonies. Loss of the selection marker and the plasmid were verified through restreaking colonies on appropriate selective media.

b. Imaging P450 Localization in Live Cells with Confocal Microscopy

Yeast cell cultures were inoculated into 3 mL of selective media and grown for 8-12 hours, to an approximate OD600 of 0.1. 1 mL of culture was pelleted at 6000 rpm for 30 seconds, the supernatant discarded and the cells resuspended in 25-50 µL media. 1-3 µL of culture were mounted on 2% agarose pads made with appropriate drop-out media to provide cells with nutrients to facilitate live cell imaging. Live yeast cells were imaged with Leica SP5 multiphoton/ confocal microscope equipped with a 63.0× glycerine immersion objective.

c. Growth Conditions for Assays

Overnight yeast cultures were started in drop-out medium with 2% dextrose (w/v) in 3 mL test tube cultures and grown at 30° C., 260 rpm or in 500 µL cultures in deep well 96 well plates covered with AeraSeal film and grown at 30° C., 480 rpm, 80% humidity in a Kuhner Lab-Therm LX-T 96-well plate shaker.

Overnight cultures were back-diluted 75-100× into appropriate dropout media supplemented with 2-4 mM norlaudanosoline. More specifically, some assays were conducted with 500 µL cultures in deep well 96 well plates covered with AeraSeal film and grown at 30° C., 480 rpm, 80% humidity in a Kuhner Lab-Therm LX-T 96-well plate shaker. Other assays were conducted using 5 mL cultures grown in 125 mL baffled flasks at 25° C., 260 rpm in a New Brunswick Scientific I24 shaking incubator. Unless otherwise indicated, cultures were sampled 96 hours following back-dilution.

e. Analysis of Metabolite Production

Aliquots of yeast cultures were centrifuged at 6000 rpm for 10 minutes and growth media samples were taken for analysis by LC-MS/MS. Samples were run on Agilent ZORBAX SB-Aq 4.6×50 mm, 5 µm column with 0.1% acetic acid as solvent A and methanol with 0.1% acetic acid as solvent B. The following method for the separation of metabolites of interest was used with a constant flow rate of 0.5 mL/min: 0-1 min, 0% to 27.5% B; 1-2 min, 27.5% B; 2-8 min, 27.5% to 60% B; 8-8.5, 35 to 100% B; 8.5-14 min, 100% B; followed by a 6 minute equilibration at 0% solvent B. After separation by HPLC, metabolites were injected into an Agilent 6320 ion trap mass spectrometer for detection and identification.

Quantification of metabolites was based on integrated peak area of the extracted ion chromatogram peaks calculated using DataAnalysis for 6300 Series Ion Trap LC/MS version 3.4 (Bruker Daltonik GmbH) and reported as the mean±s.d. We generated standard curves for reticuline, stylopine, and berberine and used the most similar standard chemical structure to estimate concentration of intermediates for which no standard was available.

III. Protoberberine-producing Yeast Strains

Strains of *S. cerevisiae* were developed that produce protoberberine alkaloids; including (S)-tetrahydrocolumbamine, (S)-canadine, and berberine; as intermediates or final products, from (S)-scoulerine or its precursors produced by an existing engineered strain, present in the culture media, or introduced to a cell lysate or lysate fraction. More specifically, these strains express any combination of (S)- scoulerine 9-O-methyltransferase (S9OMT), (S)-canadine synthase (CAS), (S)-tetrahydroprotoberberine oxidase (STOX).

The structure of protoberberine alkaloids produced by engineered yeast strains is described above, where —R may be —H, —CH$_3$, —OH, or —OR. These protoberberine alkaloids are produced from reticuline or other similar chemical species produced by an existing engineered strain, present in the culture media, or introduced to a cell lysate or lysate fraction. These strains may express any combination of the following enzymes: berberine bridge enzyme (BBE), scoulerine 9'-O-methyltransferase (S9OMT), canadine synthase (CAS), and S-tetrahydroprotoberberine oxidase (STOX).

FIG. 5 depicts the heterologous biosynthetic pathway supported by the engineered yeast strains. The gene STOX shares 78% nucleic acid sequence identity with the naturally occurring gene B. wilsonae (S)-tetrahydroprotoberberine oxidase (Table 2). This gene is a non-natural nucleotide sequence, codon-optimized for yeast expression.

Figure 6:
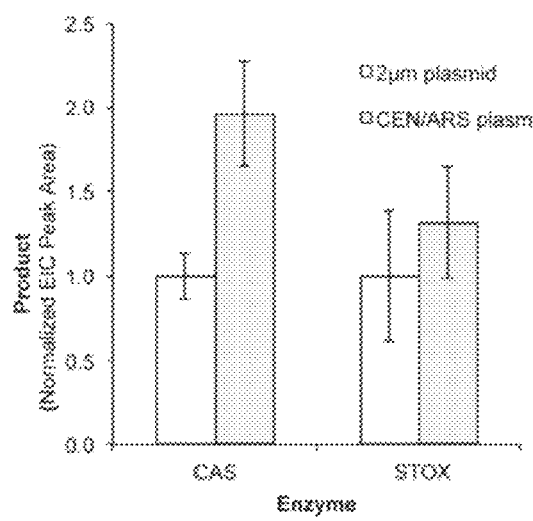
FIG. 6 depicts the effect of episomal gene copy number and expression of various cytochrome P450-NADPH reductase enzymes on protoberberine production in yeast cultures.
Figure 6:
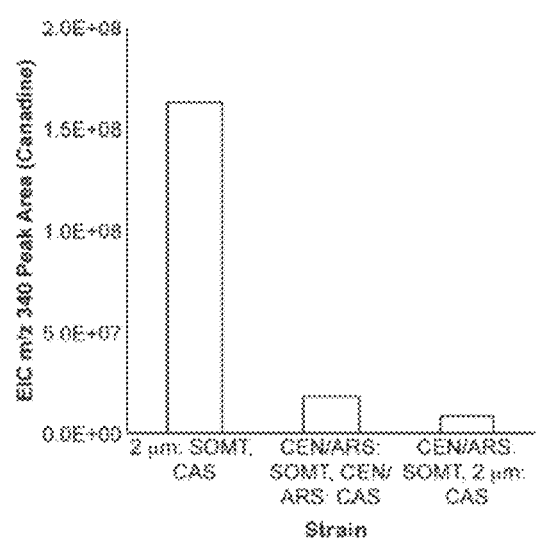
Figure 6:
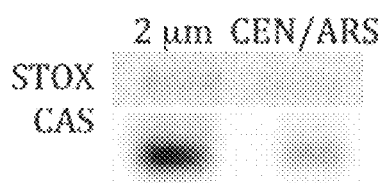
Figure 6:
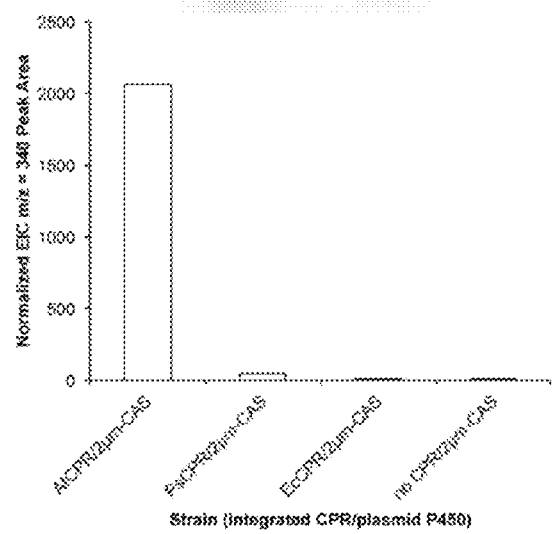

FIG. 6 depicts the effect of episomal gene copy number on protoberberine production in yeast cultures. The favored expression levels for the enzymes are relatively low (e.g., CEN/ARS vector or genomic expression) for BBE, CAS, and STOX (FIG. 6a) and relatively high (e.g., 2 μm vector or multiple genomic copies) for S9OMT (FIG. 6b). The expression levels may be altered by changing the strength of the constitutive promoter, using an inducible promoter, changing the number of copies of each gene episomally or genomically (FIG. 6c), altering the selection marker, and/or culture conditions corresponding to promoter activity or selection.

The effect of episomal gene copy number on protoberberine production was determined by assays performed in yeast cultures (FIG. 6). (a) For CAS, 4 mM norlaudanosoline was added to the media of a tetrahydrocolumbamine-producing strain with CAS expressed from either a multi-copy 2 μm plasmid or a single copy CEN/ARS plasmid. For STOX, 250 μM canadine was added to the media of a strain expressed from either a multi-copy 2 um plasmid or a single copy CEN/ARS plasmid. (b) 4 mM norlaudanosoline was added to the media of scoulerine-producing strains expressing the listed plasmids. For both experiments, after 72 h growth yeast were pelleted by centrifugation and the media was analyzed by LC-MS. Positive ion electrospray ionization (ESI) mass spectra were obtained with an Agilent 6320 Ion Trap (electrospray capillary voltage -3.5 kV; heated capillary temperature 350° C.; sheath gas: nitrogen) coupled to an Agilent 1200 Series HPLC equipped with an Agilent Zorbax SB-Aq column (3.0×50 mm 1.8 micron) and an Agilent Zorbax SB-Aq guard column (2.1×12.5 mm 5 micron). The LC separation method was isocratic elution with H20 for 1 min, gradient elution to H2O:CH$_3$OH 75:25 over 3 min, gradient elution to 100% CH$_3$OH over 1 min, and finally isocratic elution for 4 min with a flow rate of 0.6 mL min-1. Both solvents were 0.1% acetic acid. Extracted ion chromatograms for the product extracted ion chromatograms for the molecular ion were plotted and manually integrated. Error bars are S.D. of three biological replicates. (c) Copy number is rank-order correlated with expression level. Samples were prepared from overnight cultures of yeast strains with the indicated plasmid as described by Kushnirov et al. (2000). Yeast 16, 857-860, which is incorporated by reference in its entirety. Following SDS-PAGE, proteins were transferred to a nitrocellulose membrane, which was blocked for 1 hour in 5% BSA and then probed with HRP-conjugated anti-HA antibody overnight. The membrane was imaged following incubation with enhanced chemiluminescent HRP substrate.

The effect of cytochrome P450-NADPH reductase partners on CAS activity was investigated (FIG. 6d). The co-expression of the cytochrome P450 reductase ATR1 with CAS resulted in higher CAS activity than E. californica CPR, A. thaliana ATR2, P. somniferum CPR, or endogenous yeast CPR. Assays were performed in vivo with 4 mM norlaudanosoline in yeast expressing CAS from a multi-copy plasmid. Positive ion electrospray ionization (ESI) mass spectra were obtained as described herein. Extracted ion chromatograms for the product standard molecular ion were plotted and manually integrated. The data were normalized such that the peak area in the absence of CPR=1.

Functional expression of STOX in yeast culture was observed. Assays were performed in vivo with 250 μM canadine (m/z=340) in yeast expressing STOX from CEN/ARS plasmid. Positive ion electrospray ionization (ESI) mass spectra were obtained as described for FIG. 6. Extracted ion chromatograms for the berberine product (m/z=336) and a 1 uM berberine standard molecular ion were plotted and smoothed using the Gauss processing tool for 1 cycle at the default smoothing width in DataAnalysis for 6300 Series Ion Trap LC/MS v. 3.4.

In order to enhance the accumulation of BIAs within the yeast cell, heterologous transporters, for example plant ATP-binding cassette proteins from BIA-producing plants, are expressed in the engineered strains. These transporters are CjABCB1, CjABCB2, and/or CjABCB2 and act to accumulate berberine within the yeast cell.

Figure 7:
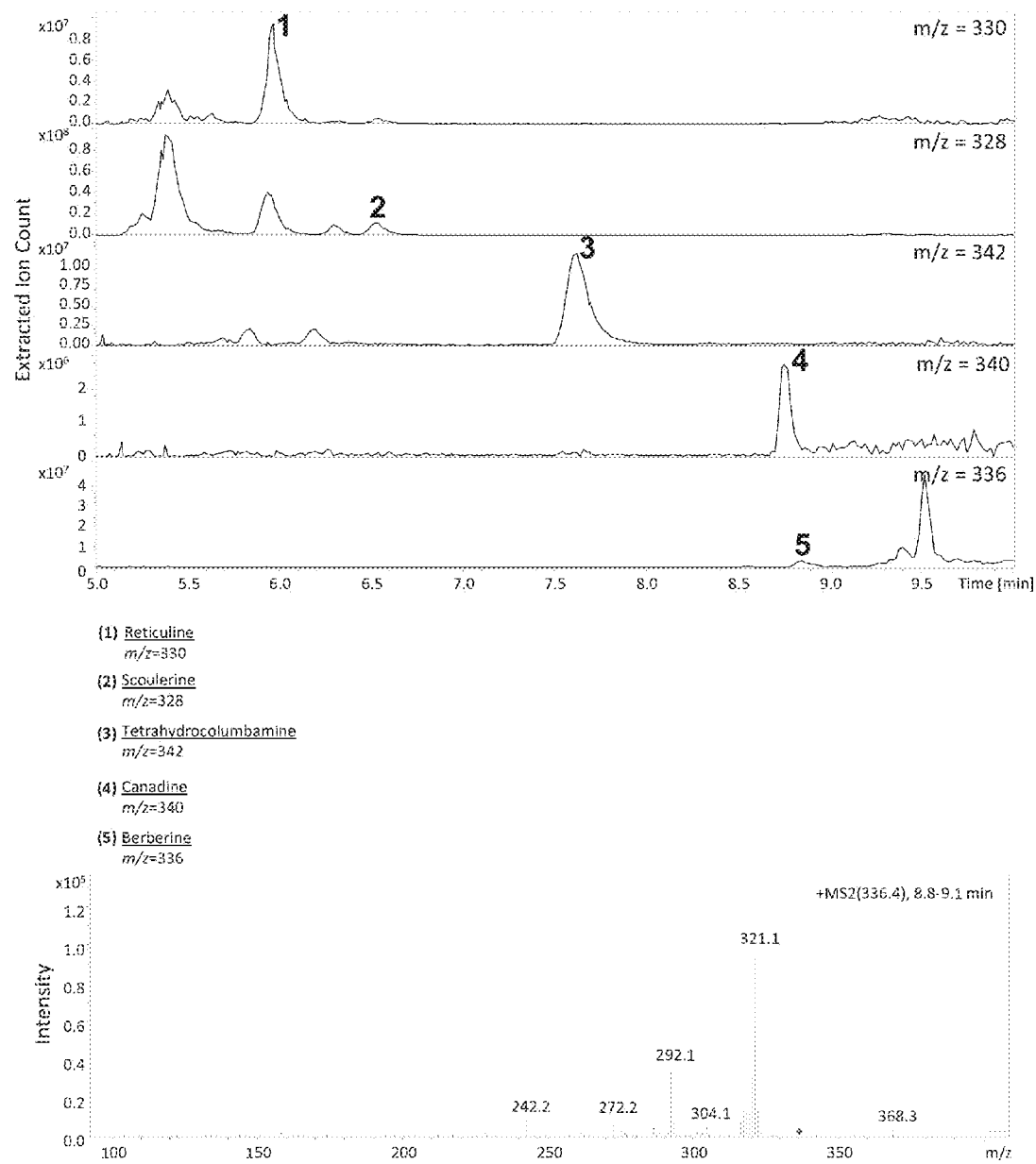
FIG. 7 depicts the microbial production of berberine from norlaudanosoline.

FIG. 7 depicts in vivo production of berberine from norlaudanosoline. The production of reticuline, scoulerine, tetrahydrocolumbamine, canadine, and berberine was demonstrated from cultures of host cells expressing SOMT, CAS, BBE, and STOX from a YAC; having a second copy of SOMT on a high copy 2 μm plasmid; ATR1 integrated; and three enzymes to convert norlaudanosoline to reticuline integrated. Assays were performed with 4 mM norlaudanosoline in yeast cultures for 96 h. Products were identified in media by LC-MS as described for FIG. 6: Reticuline m/z 330, scoulerine m/z 328, tetrahydrocolumbamine m/z 342, canadine m/z 340 and berberine m/z 336. The MS/MS spectra for m/z 336 demonstrates that product 5 is berberine, as this spectra matched the spectra of a berberine standard.

IV. Thebaine-producing Yeast Strains

Yeast strains were engineered that produce thebaine, as an intermediate or final product, from salutaridine or its precursors produced by an existing engineered strain, present in the culture media, or introduced to a cell lysate or lysate fraction. More specifically, these strains express any combination of salutaridine reductase (SalR) and salutaridinol 7-O-acetyltransferase (SalAT).

FIG. 8 depicts the heterologous biosynthetic pathway supported by the engineered yeast strains.

FIG. 9 depicts the conversion of salutaridine to thebaine in crude lysate of engineered yeast. The functional expression of both SalR and SalAT was observed by monitoring ion counts (EIC) m/z=312 peak areas, which results in the production of thebaine from salutaridine. Strains containing P. bracteatum SalR produced greater thebaine than strains containing, P. somniferum SalR. Strains containing SalR with the F104A or I275A mutation produced greater thebaine than strains containing SalR without these mutations. The combination of enzymes may also include any of the codon-optimized variants of SalAT listed in Table 2. Assays were performed with 100 μM salutaridine and 50 μM NADPH in crude lysate of yeast expressing SalR and SalAT from the genome. Positive ion electrospray ionization (ESI) mass spectra were obtained as described for FIG. 6. Extracted ion chromatograms for the product standard molecular ion were plotted and manually integrated.

The SalAT genes share less than or equal to 80% nucleic acid sequence identity with their naturally occurring counterparts (Table 3). These genes are non-natural nucleotide sequences, codon-optimized for yeast expression.

The conversion of salutaridine to thebaine catalyzed by SalR and SalAT occurs in a crude lysate of the yeast strain expressing both enzymes supplemented by the cofactor NADPH (FIG. 9).

SalAT and SalR are also expressed in engineered strains expressing additional enzymes such that the strain produces products for which thebaine is a precursor. For example, the strain may produce oripavine, morphine, codeine, hydromorphone, hydrocodone, oxycodone, and/or oxymorphone.

The conversion of salutaridine to thebaine catalyzed by SalR and SalAT occurs in an engineered yeast strain modified to produce increased amounts of NADPH (Table 2).

The yeast strain is engineered to increase production of salutaridinol or thebaine or products for which thebaine is a precursor from reticuline or its precursors by localizing SalR and/or SalAT to organelles in the yeast cell. For example, SalR and/or SalAT may be localized to the yeast endoplasmic reticulum in order to decrease the spatial distance between SalR and/or SalAT and CYP2D6 or SalSyn or an engineered cytochrome P450 enzyme that catalyzes the conversion of reticuline to salutaridine.

V. Opiate-producing Yeast Strains

A. Example 1

1. Introduction

The following section describes the production and characterization of yeast to support the final steps in opiate biosynthesis, yielding strains that can produce naturally occurring opiates and semi-synthetic opioids. The results described herein highlight that the loss of native regulation strategies upon transfer of a plant biosynthetic pathway to a microbial host can result in new pathway branches that direct flux toward undesired byproducts. To restore and control pathway specificity, a general organelle routing toolkit was created that directs enzymes to specific native cellular compartments. This toolkit was used in a novel spatial engineering approach to actively delocalize plant pathway enzymes to yeast endomembranes, thus increasing specificity of morphine production over the byproduct neomorphine from 44% up to 96%. Heterologous morphine biosynthesis was further optimized by increasing supply of the co-substrate 2-oxoglutarate and titrating gene copy number to balance pathway flux. By incorporating bacterial enzymes within the heterologous pathway, we demonstrated the biosynthesis of a panel of valuable semi-synthetic opiates, including up to 51 mg/L hydrocodone, 70 mg/L oxycodone, and 1 mg/L hydromorphone, which are typically produced by chemical modification of natural opiates. Optimized engineered yeast strains produced 31-132 mg/L total opioid products, demonstrating the development of a microbial biomanufacturing platform to supply natural and semi-synthetic opioids to the pharmaceuticals industry.

2. Results a. Constructing a Morphine Biosynthetic Pathway in Yeast

The biosynthesis of morphine from thebaine is catalyzed by three enzymes in *P. somniferum*: the 2-oxoglutarate/$Fe^{2+}$-dependent dioxygenases T6ODM and CODM, and NADPH-dependent aldo-keto reductase COR. These enzymes form two biosynthetic routes from thebaine to morphine. One route (i) includes a non-enzymatic rearrangement and generates intermediates neopinone, codeinone (1), codeine (2), and morphine (4) (FIG. 15). Based on reported substrate affinities of T6ODM and CODM, this is the predominant pathway in poppy. The minor route (ii) generates oripavine and morphinone as intermediates to morphine (FIG. 15).

FIG. 15 depicts engineering a heterologous morphine biosynthesis pathway in yeast. The schematic depicts observed transformations of thebaine by the morphine biosynthesis enzymes—thebaine 6-O-demethylase (T6ODM), codeine O-demethylase (CODM), and codeinone reductase (COR) from opium poppy *P. somniferum*. Two routes to morphine which pass through intermediates codeinone and codeine (route i) and oripavine and morphinone (route ii) occur in opium poppy. Route (i) and a newly-identified route to neomorphine (iii) occur in the heterologous context of a yeast cell, demonstrating a broader substrate range for COR and CODM.

To reconstruct a morphine biosynthetic pathway in *S. cerevisiae*, we expressed yeast codon-optimized T6ODM, COR1.3, and CODM each flanked by unique yeast promoters and terminators and assembled into a single yeast artificial chromosome (YAC) vector (pYES1L). From the four characterized *P. somniferum* COR isoforms, COR1.3 was selected because it had the highest affinity for codeinone. After culturing this strain with thebaine for 96 h, we observed codeinone, codeine, and morphine in the culture medium, demonstrating that these heterologous plant enzymes are capable of catalyzing transformations of opiates in yeast (FIG. 15). However, the detected opiate levels were low, with morphine production as low as 0.2 mg/L, suggesting that optimization efforts would be required to increase conversion efficiencies. Neopinone was not detected in this assay, likely because this intermediate is unstable and rearranges to codeinone over the course of the experiment.

Additional opiates detected in the culture medium indicated differences between the biosynthetic routes observed in the natural and heterologous systems. Intermediates from the minor route to morphine observed in plants—oripavine and morphinone—were not detected in the engineered yeast strain, suggesting that the low activities of each of these enzymes on their alternative substrates precluded detectable levels. However, two other products were observed in similar quantities to codeine and morphine. The first had the same mass/charge (m/z) ratio as codeine and was determined to be neopine (3) by MS/MS analysis. Neopine may be produced by the activity of COR on the direct product of T6ODM, neopinone, before it rearranges to codeinone (FIG. 15). The second unknown product had the same m/z ratio as morphine and was determined to be neomorphine (5), produced by the CODM-catalyzed demethylation of neopine. Therefore, the analysis uncovered a novel, but undesired, opiate pathway (iii) in the engineered yeast strain (FIG. 15).

b. Increasing Supply of the Co-substrate 2-oxoglutarate for Morphine Biosynthesis It was examined whether supply of a key co-substrate, 2-oxoglutarate, was limiting in the heterologous morphine biosynthesis pathway. The dioxygenases T6ODM and CODM require 2-oxoglutarate to accept one oxygen atom in the oxidative demethylation of thebaine and codeine, respectively. Thus, it was examined whether increasing 2-oxoglutarate supply would enhance flux through our engineered biosynthetic pathway.

In endogenous yeast nitrogen metabolism, glutamate dehydrogenase (GDH) enzymes catalyze the interconversion of glutamate and 2-oxoglutarate (FIG. 16). Thus, increasing glutamate supply can increase the intracellular 2-oxoglutarate pool. Monosodium glutamate (MSG), a common nitrogen source, was titrated into the yeast culture medium. Glutamine was included in the culture medium as a nitrogen source to ensure the cultures were not nitrogen-limited and hence prevent positive growth effects due to MSG supplementation. No differences in final cell densities were observed with varying levels of MSG. Upon increasing MSG concentration from 0 to 2.5 g/L an increase in morphine production was observed from 0.24 to 0.45 mg/L after 96 h growth (FIG. 16b).

It was next examined whether direct addition of the co-substrate 2-oxoglutarate to the culture medium would further enhance flux through the pathway. 2-oxoglutarate was titrated into the culture medium up to concentrations of 100 mM. Supplying this co-substrate directly, in addition to 2.5 g/L MSG, increased morphine titers to 2.5 mg/L, a more than 10-fold increase over the titer observed in standard medium (FIG. 16b). All subsequent opiate-producing cultures were grown in this optimized culture medium supplemented with 0.5 g/L glutamine, 2.5 g/L MSG, and 50 mM 2-oxoglutarate.

FIG. 16 depicts enhanced co-substrate 2-oxoglutarate supply increases morphine biosynthesis titers. (a) In yeast metabolism 2-oxoglutarate participates in the tricarboxylic acid (TCA) cycle and in nitrogen assimilation where it is reversibly converted to glutamate by the activity of glutamate dehydrogenases Gdh1p, Gdh2p and Gdh3p. (b) Synthetic complete medium containing 0.5 g/L glutamine as a nitrogen base was supplemented with monosodium glutamate (MSG) up to 2.5 g/L, and then with 2-oxoglutarate up to 100 mM. A yeast strain (CSY907) expressing T6ODM, COR1.3, and CODM from a pYES1L vector was cultured at the indicated culture medium compositions for 96 h in deep-well plates with 1 mM thebaine. Morphine production levels were determined by LC-MS analysis of the culture medium. Error bars show ±1 SD of three biological replicates.

c. Balancing Enzyme Expression Levels to Increase Morphine Titer

It was next examined whether optimizing relative enzyme expression levels would increase pathway flux to morphine. The enzyme COR catalyzes the reversible reduction of codeinone to codeine in morphine biosynthesis. COR also catalyzes the reversible reduction of neopinone to neopine in yeast (FIG. 15). The presence of these reversible reactions suggested that pathway flux toward the production of codeine, and consequently morphine, could be further increased by titrating the expression levels of pathway enzymes.

To examine the combinatorial design space around T6ODM, COR, and CODM expression levels, strains with varied gene copy numbers were constructed for each of the enzymes. In all strains, single copies of T6ODM, COR, and CODM were expressed from a YAC vector. Additional copies of one or more genes were integrated with a constitutive GPD promoter into the host cell genome at auxotrophic loci. The strains were cultured with 1 mM thebaine in optimized medium (0.5 g/L glutamine, 2.5 g/L MSG, and 50 mM 2-oxoglutarate) for 96 h in 96-well plates. Morphine and neomorphine titers were compared to those of the control strain with only the YAC vector (T6ODM:COR: CODM gene ratio of 1:1:1).

Figure 17:
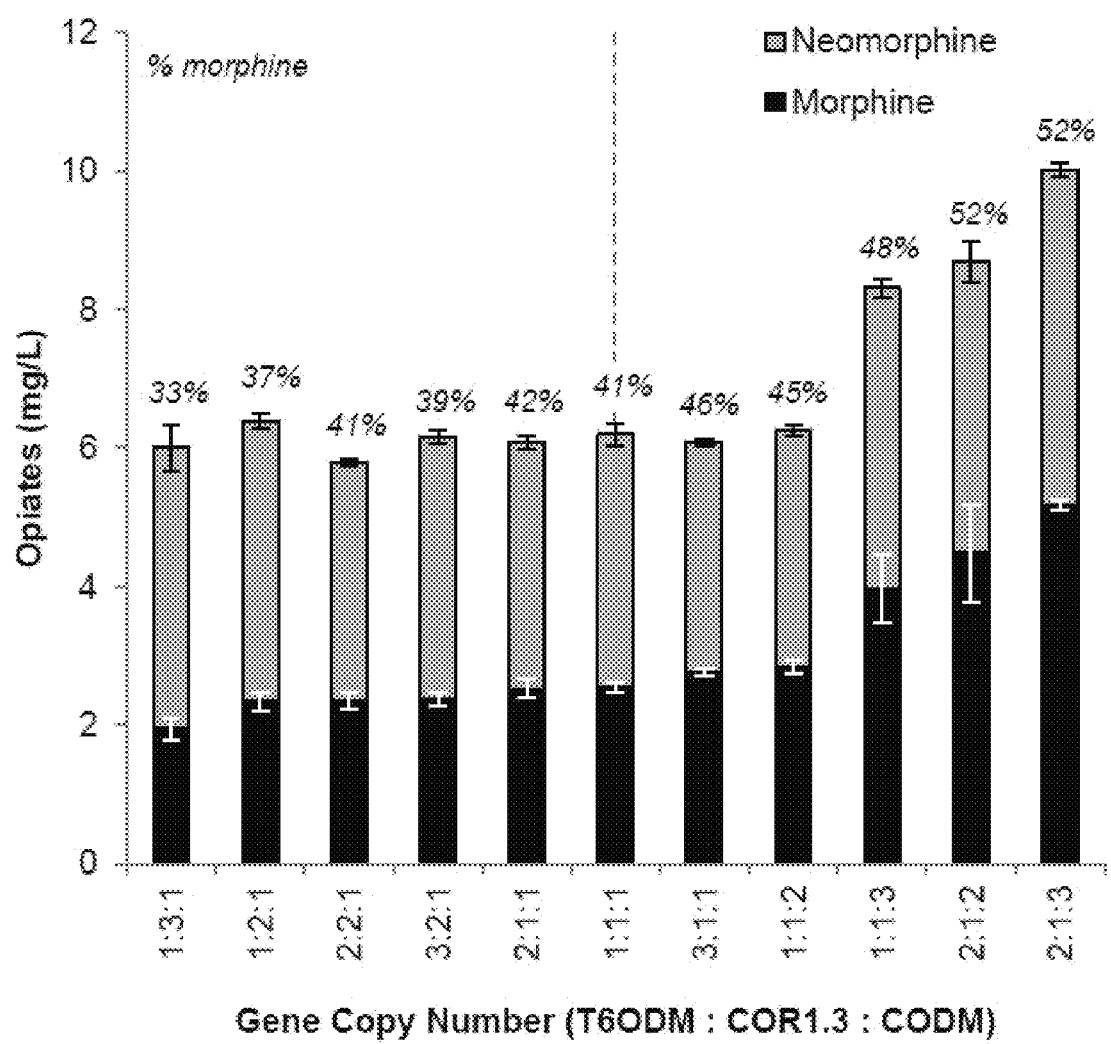
FIG. 17 depicts a design to alter gene copy number to increase pathway flux to morphine. Titers of the target product morphine (black bars) and non-target neomorphine (grey bars) were analyzed from strains harboring different numbers of copies of T6ODM, COR1.3, and CODM. The culture medium was analyzed by LC-MS for opiate production after 96 h growth in deep-well plates with 1 mM thebaine. Each strain expressed one copy of T6ODM, COR1.3, and CODM, on a pYES1L vector. Additional gene copies were integrated into the host cell genome. The control strain expressing one copy of each gene from the pYES1L vector (gene ratio 1:1:1) produced an intermediate level of morphine and is indicated in the graph by a broken line. Error bars show ±1 SD of three biological replicates.

Altering the copy numbers of pathway genes changed the overall opiate titers and relative levels of morphine and neomorphine. Increasing the copy number of COR alone (e.g., 1:3:1) or together with T6ODM (e.g., 2:2:1) decreased morphine production while increasing neomorphine production, such that overall opiate production was similar but differed in the ratio of end products (FIG. 17). For example, the control 1:1:1 strain produced 2.5 mg/L morphine and 3.7 mg/L neomorphine, a total of 6.2 mg/L end product opiates. In contrast, the 1:3:1 strain produced 2.0 mg/L morphine and 4.1 mg/L neomorphine; a different ratio of morphine to neomorphine, but a similar total end product titer. Other gene copy number combinations within the design space provided increases in morphine and total end product titers. For example, increased CODM copy number resulted in higher production levels of both morphine and neomorphine (FIG. 17). This effect was enhanced by additional gene copies of T6ODM such that one ratio of interest of T6ODM: COR:CODM was 2:1:3, which produced 5.2 mg/L morphine and 4.8 mg/L neomorphine, a total of 10.0 mg/L end product opiates in culture medium (FIG. 17).

Figure 18:
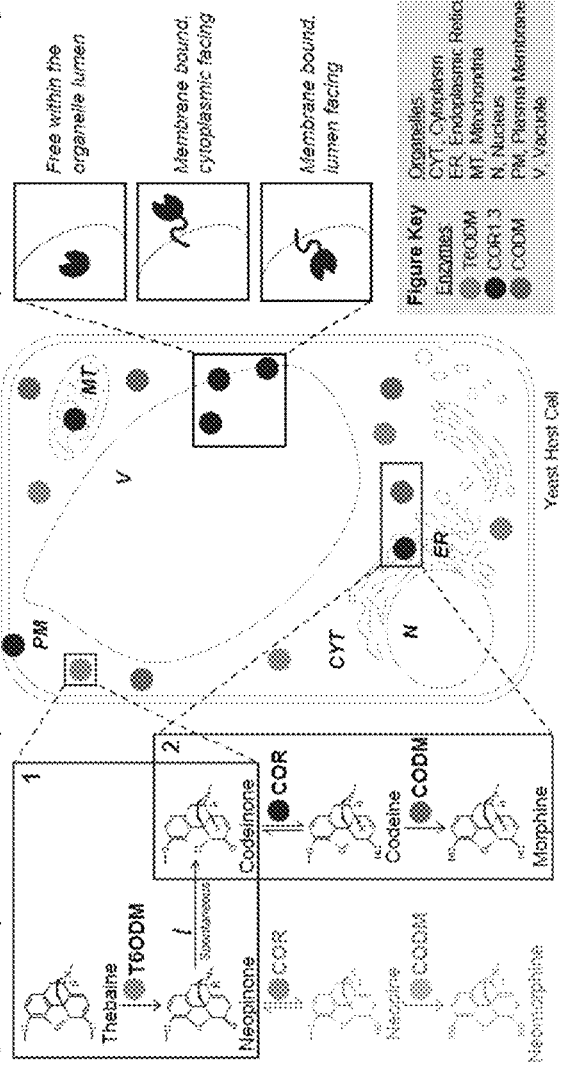
FIG. 18 depicts a spatial engineering approach to improve pathway specificity for morphine. (a) Schematic depicting the rationale for using a spatial engineering approach based on enzyme delocalization to improve pathway specificity for the target product morphine. Localizing COR1.3 to an organelle can isolate this enzyme from the non-target substrate neopinone (produced by cytoplasmic T6ODM activity) and allow additional time for the intervening spontaneous isomerization of neopinone to the target substrate codeinone to occur. In such a scheme the heterologous pathway is divided into two parts: (1) cytoplasmic T6ODM (circle) converts thebaine to neopinone, which subsequently rearranges to codeinone at an unknown rate; and as a result (2) isolated COR1.3 (circle) has greater access to codeinone than neopinone and converts this substrate to codeine, which is then irreversibly demethylated by CODM (circle) to morphine. The overall effect of this localization scheme is to direct pathway flux toward the target end-product morphine. As a design consideration for COR1.3 localization, the enzyme may be directed to an organelle in one of three configurations: free within the organelle lumen, membrane localized with the enzyme extending into the cytoplasm, or membrane localized with the enzyme extending into the organelle lumen. (b) An organelle routing toolkit allows for modular routing of proteins to specified organelles in the yeast host cell. A set of modular localization tags (ER1: SEQ ID NO:1, ER2: SEQ ID NO:2, ER3: SEQ ID NO:3 and 4, V1: SEQ ID NO:5, PM1: SEQ ID NO:6, and MT1: SEQ ID NO:7) was designed to fuse to any enzyme via a 7 amino acid linker of either Gly$_6$SerThr (SEQ ID NO:8) at the N-terminus or ProGly$_6$ (SEQ ID NO:9) at the C-terminus. To validate the tags, each was fused to the fluorescent protein GFP and imaged in live yeast cells. Organelle markers KAR2-DsRed-HDEL (SEQ ID NO:4) and COX4-mCherry were included in the organelle routing toolkit as ER3 and MT1, respectively. Untagged COR1.3 (COR1.3-GFP) localized to the cytoplasm in yeast cells. Scale bars, 4 μm.
Figure 18:
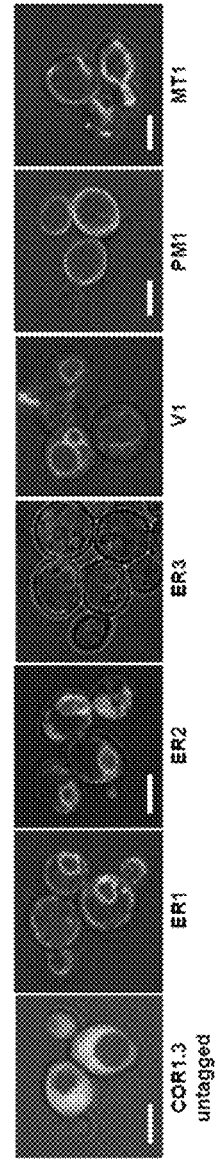

The observed relationship between morphine titers and gene copy number ratios suggested two mechanisms of improvement in the engineered strains. First, providing additional gene copies of the final enzyme CODM increased the total amount of end products produced, e.g., by increasing the rate of conversion of codeine and neopine to morphine and neomorphine, respectively, and thus increasing the forward rate of the reversible COR reaction. Second, expression level changes that improved overall end product titers also improved specificity for the target product morphine over the byproduct neomorphine. Specifically, in the lower yielding 1:3:1 strain morphine comprised 33% of the total end product opiates, while in a higher yielding 2:1:3 strain morphine comprised 52%. An analysis of pathway conversion efficiencies showed that CODM favors codeine as a substrate and thus biases the pathway for morphine production at high copy number. In some cases of balanced copy number strains, non-target neomorphine still accounted for almost half the final product.

d. Developing and Implementing a Localization Toolkit to Improve Pathway Specificity Earlier engineering efforts indicated that nearly half of the potential morphine yield was shunted to the unwanted side-product neomorphine (FIG. 18), making pathway specificity an important engineering challenge. Conversion efficiencies were examined across the engineered pathway and determined that one cause of the branching from morphine to non-target neomorphine is the intervening spontaneous step between the reactions catalyzed by T6ODM and COR. An engineering strategy in which T6ODM and COR is spatially separated in the cell may allow additional time for the intervening spontaneous rearrangement of neopinone to codeinone (FIG. 18). Specifically, by isolating COR to a yeast organelle it is possible to restrict access of this enzyme to the neopinone produced by cytoplasmic T6ODM, providing neopinone additional time to rearrange to codeinone and ultimately be converted to morphine.

To address this specificity challenge and more broadly enable spatial engineering approaches in yeast, a modular organelle routing toolkit was developed. The toolkit is composed of 6 validated localization tags derived from endogenous yeast proteins. These tags route to a variety of yeast organelles: the endoplasmic reticulum (ER), mitochondria (MT), plasma membrane (PM), and vacuole (V) (FIG. 21a, b). An ER routing tag ER1, a vacuole tag V1, and a plasma membrane tag P1 were developed based on transmembrane domains from three proteins within the tail-anchored class of proteins. These 31-35 amino acid tags are sufficient to direct the post-transcriptional localization of a target protein, such that the C-terminus inserts into the endomembrane of the assigned organelle and the protein is extended into the cytoplasm. To access the internal organelle environment, a second ER routing tag called ER2 was designed based on the 28 amino acid transmembrane domain of integral membrane protein calnexin. Two additional sequences to localize proteins free within the ER lumen (ER3) and the mitochondrial matrix (MT1) were taken from the established ER and mitochondrial markers KAR2-DsRed-HDEL and COX4-mCherry, respectively. To confirm the targeted localization, each member of the organelle routing toolkit was fused to GFP and examined by confocal microscopy (FIG. 18b).

Figure 19:
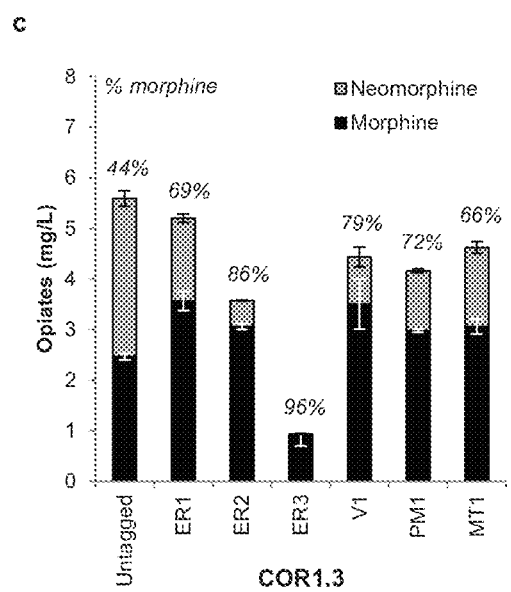
FIG. 19 illustrates that the organelle routing toolkit may be used to localize the heterologous COR1.3 enzyme to yeast organelles to enhance titer and selectivity for morphine. Localized COR1.3 variants were expressed together with untagged T6ODM and CODM in a yeast host cell. Strains were cultured in optimized media with 1 mM thebaine, grown for 96 h, and culture medium analyzed for morphine (black bars) and neomorphine (grey bars) by LC-MS.

The organelle routing toolkit was applied to the COR enzyme in the morphine pathway to determine whether physical delocalization of pathway enzymes could increase flux to the desired product (morphine) and decrease flux to the undesired product (neomorphine). A control strain in which COR1.3 was untagged and thus localized to the cytoplasm (CYT) with T6ODM and CODM produced 2.5 mg/L morphine with 44% specificity after 96 h growth (FIG. 19). When the organelle routing toolkit was employed fusing each localization tag to COR to actively route this enzyme to different cellular compartments increased specificity (relative production of the desired product) and titer (absolute production levels of the desired product) were observed for morphine. COR localization to the ER (ER1 tag) and vacuole (V1 tag) facing into the cytoplasm resulted in strains with high morphine titers at approximately 3.5 mg/L. In contrast, the strain with ER3 tagged COR, localized to the ER lumen, had nearly 100% specificity for morphine, but at reduced titers of less than 1 mg/L. The localization of COR to the ER-lumen with the ER2 tag provided a balance of enhanced yields and specificity, resulting in morphine titers of 3.1 mg/L at 86% specificity, and was carried forward in subsequent experiments.

Table 5 (below) depicts Organelle Routing Toolkit. Modular targeting sequences were used to localize enzymes to organelles in engineered yeast strains. An enzyme selected for localization was fused to the targeting sequence using an intervening 7 amino acid linker of either $Gly_6SerThr$ (SEQ ID NO:8) at the N-terminus or $ProGly_6$ (SEQ ID NO:9) at the C-terminus.

TABLE 5

Abbreviations: ER, endoplasmic reticulum; MT, mitochondria; PM, plasma membrane

| Tag | Gene | GenBank ID | Encodes | Organelle | Length | Tag Type |
|---|---|---|---|---|---|---|
| ER1 | CYB5 | AAA67468.1 | Cytochrome b5 | ER | 31 | Tail anchor |
| ER2 | CNE1 | AAA65967.1 | Cainexin | ER | 28 | Type I TM |
| ER3 | KAR2 | AAA34713.1 | Chaperone | ER | 42 | Lumenal |
| V1 | NYV1 | EDN59638.1 | v-SNARE | V | 35 | Tail anchor |
| PM1 | SNC1 | EEU07245.1 | v-SNARE | PM (ER, golgi) | 32 | Tail anchor |
| MT1 | COX4 | EEU04676.1 | Cytochrome c oxidase subunit 4 | MT | 22 | Mitochondrial import |
| * | FIS1 | AAS56177.1 | Fission protein | MT | 27 | Tail anchor |
| * | PRC1 | AAA34902.1 | Carboxypeptidase Y | V | 50 | Vacuole import |

| Tag Type | TM | C- or N- terminus | Facing | Amino Acid Sequence |
|---|---|---|---|---|
| Tail anchor | Yes | C | Cytoplasmic | STSENQSKGSGTLVVILAILMLGVAYYLLNE |
| Type I TM | Yes | C | ER lumen | ILEQPLKFVLTAAVVLLTTSVLCCVVFT |
| Lumenal | No | N | ER lumen | MFFNRLSAGKLLVPLSVVLYALFVVILPLQ NSFHSSNVLVRG |
| Tail anchor | Yes | C | Cytoplasmic | NIKEIMWWQKVKNITLLTFTIILFVSAAFM FFYLW |
| Tail anchor | Yes | C | Cytoplasmic | WYKDLKMKMCLALVIILLVVIIVPIAVHFSR |
| Mitochondrial import | No | N | Mitochondrial matrix | MLSLRQSIRFFKPATRTLCSSR |
| Tail anchor | Yes | C | Cytoplasmic | LKGVVVAGGVLAGAVAVASFFLRNKRR |

TABLE 5-continued

Abbreviations: ER, endoplasmic reticulum;
MT, mitochondria; PM, plasma membrane

| | | | | |
|---|---|---|---|---|
| Vacuole import | No | N | V lumen | MKAFTSLLCGLGLSTTLAKAISLQRPLGLDKD VLLQAAEKFGLDLDLDHL |

*Unnamed tags did not confer modular, stable localization to the predicted compartment plasma membrane;
TM, transmembrane domain;
V, vacuole.
predicted compartment.
ER1 (SEQ ID NO: 1)
ER2 (SEQ ID NO: 2)
ER3 (SEQ ID NO: 3)
V1 (SEQ ID NO: 5)
PM1 (SEQ ID NO: 6)
MT1 (SEQ ID NO: 7)
* FIS1 (SEQ ID NO: 10)
* PRC1 (SEQ ID NO: 11)

e. Incorporating Microbial Enzymes to Achieve Biological Synthesis of Semi-synthetic Opioids Bacterium strain *Pseudomonas putida* M10, identified in waste from an opium-poppy processing factory, performs enzymatic transformations of opioids. Two characterized enzymes from this strain—$NADP^+$-dependent morphine dehydrogenase (morA) and NADH-dependent morphinone reductase (morB)—catalyze many of these reactions. MorA, an aldo-keto reductase, and morB, an α/β-barrel flavoprotein oxidoreductase, are heterologously expressed in *E. coli* to convert morphine to hydromorphone.

It was examined whether morA and morB extend the biosynthetic capabilities of the morphine-producing yeast strains to the valuable end products hydrocodone, oxycodone and hydromorphone (FIG. 20). In a single YAC, the *P. somniferum* genes T6ODM, COR, and CODM and the *P. putida* genes morA and morB were included. A yeast strain transformed with this YAC and cultured with 1 mM thebaine produced only a trace amount of hydrocodone and no detectable hydromorphone after 96 h growth.

Engineered yeast strains expressing different combinations of the *P. somniferum* and *P. putida* M10 enzymes from a pYES1L vector produce different levels of target opioids.

| | Opiates (mg/L) in Culture Medium | | | | |
|---|---|---|---|---|---|
| Genes Expressed: | Morphine | Neomorphine | Hydrocodone | Oxycodone | Hydromorphone |
| T6ODM, CODM, COR1.3, morA, morB | 0 | 21 | 2.08 | trace | — |
| T6ODM, CODM, morA | 2.36 | 1.04 | — | — | — |
| T6ODM, CODM, morA, morB | 0.26 | 1.68 | 1.34 | trace | 0.10 |
| T6ODM, morB | — | — | 6.48 | 2.12 | — |

Figure 23:
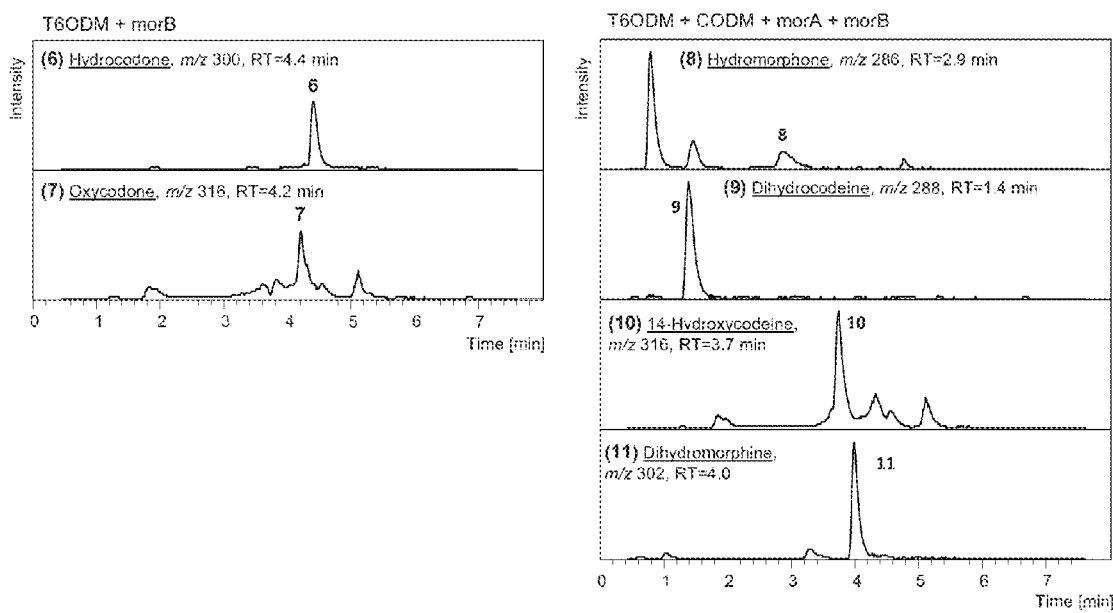
FIG. 23 depicts LCMS analysis of metabolites secreted into the culture medium by engineered yeast strains expressing enzymes from *P. somniferum* and *P. putida* M10. Strain CSY946 (expressing T6ODM and morB) and CSY945 (expressing T6ODM, CODM, morA and morB) were cultured for 96 hours in the presence of thebaine. The LCMS peaks 6-11 correspond to hydrocodone, oxycodone, hydromorphone, dihydrocodeine, 14-hydroxycodeine, and dihydromorphine.

An alternative biosynthetic route to the semi-synthetic opioids hydrocodone and hydromorphone was developed. It was first determined whether morA could reduce codeinone to codeine in place of COR in the morphine biosynthesis pathway by replacing COR with morA in the YAC encoding morphine production. The substitution of morA activity for COR resulted in 2.4 mg/L morphine with 69% selectivity, greater than the selectivity of any of the untagged COR isoform strains. morB was included to generate a four gene YAC with T6ODM, CODM, morA, and morB. A strain with this YAC produced 1.3 mg/L hydrocodone and 0.10 mg/L hydromorphone. The opioids dihydrocodeine and dihydromorphine were also detected, due to morA and morB activity on hydrocodone and hydromorphone (FIGS. 20 and 23). 14-hydroxycodeine was observed, presumably resulting from morA activity on 14-hydroxycodeinone (FIG. 23). The hydroxylation of codeinone to 14-hydroxycodeinone has been observed to occur spontaneously in vitro. Trace amounts of another 14-hydroxylated product, oxycodone, were observed presumably due to the activity of morB on 14-hydroxycodeinone. Based on these results, a strain expressing only T6ODM and morB was engineered to increase pathway flux to the morB products hydrocodone and oxycodone. This two-enzyme strain produced 6.5 mg/L hydrocodone and 2.1 mg/L oxycodone, confirming that 14-hydroxylation is occurring as part of the pathway (FIG. 20).

Next, the ability of morA and morB mutants to increase flux to hydromorphone was examined. Specifically, morA Cys81 Ser was tested, which prevents irreversible product inhibition by morphinone at Cys81 on the enzyme surface. In addition, an alternative morB amino acid sequence (RCSB PDB: 1GWL_A) with a Glu160Gly mutation relative to the original reported sequence (UniProtKB: Q51990) was tested. The $morA^{C81S}$ and $morB^{E160G}$ variants were examined individually and in combination in the engineered pathway. The control strain, expressing T6ODM, CODM, morA, and morB, produced 1.3 mg/L hydrocodone and 0.10 mg/L hydromorphone. Substituting morA with the $morA^{C81S}$ variant reduced titers of both hydrocodone and hydromorphone to 0.9 mg/L and 0.09 mg/L, respectively. Substituting morB with $morB^{E160G}$ resulted in increased levels of hydromorphone in the culture medium. For example, strains expressing T6ODM, CODM, morA, and $morB^{E160G}$ produced 0.9 mg/L hydrocodone and 0.14 mg/L hydromorphone. The reduced hydrocodone titer suggested that the $morB^{E160G}$ variant has reduced activity on codeinone, redirecting flux to hydromorphone.

f. Combining Strain Engineering Approaches to Produce Natural and Semi-synthetic Opioids The genetic design elements described herein were used to construct three production strains for target opioid biosynthesis. The morphine production strain (CSY950) incorporated a genome-integrated copy of T6ODM, two integrated copies of CODM, and a YAC encoding COR1.3-ER2, T6ODM, and CODM. This strain directed pathway flux to morphine with ER-localized COR1.3 and enhanced overall pathway flux with the optimal 2:1:3 ratio of T6ODM: COR1.3:CODM. The hydromorphone production strain (CSY951) incorporated a genome-integrated copy of T6ODM, two integrated copies of CODM, and a YAC encoding T6ODM, CODM, morA, and morB$^{E160G}$. This hydromorphone production strain directed flux to hydromorphone with the morB$^{E160G}$ variant and enhanced overall production with the optimal gene copy number ratio. The hydrocodone/oxycodone production strain (CSY952) incorporated two integrated copies of T6ODM and a YAC encoding T6ODM and morB. These production strains were grown in parallel 0.25 L closed batch fermentations. Ten key opioid end products—codeine, neopine, morphine, neomorphine, hydrocodone, oxycodone, hydromorphone, dihydrocodeine, 14-hydroxycodeine, and dihydromorphine—were monitored over the course of the fermentation. Target opioids were detected in the culture medium after 24 h, increased in concentration with increasing cell density, and continued to accumulate in stationary phase. Strains CSY950, CSY951, and CSY952 accumulated 31, 68, and 132 mg/L target opioid molecules, respectively, in the culture medium during the course of the fermentation (FIG. 21).

Figure 21:
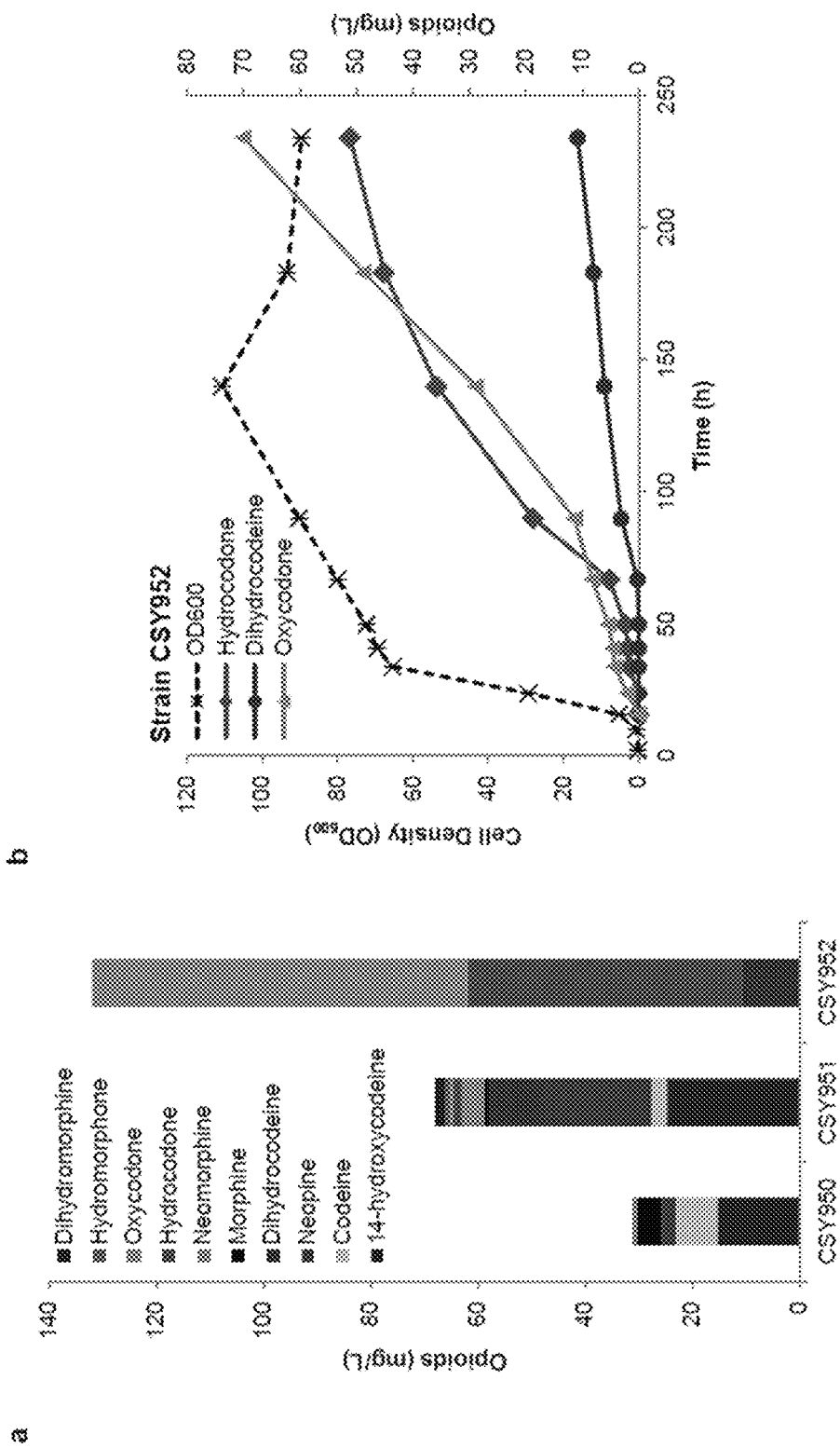
FIG. 21 depicts optimized yeast strains for the production of diverse opioids. (a) Total opioid molecule concentration in the culture medium after closed-batch fermentation. Yeast strains CSY950, CSY951, and CSY952 (Table 4) were optimized for the production of morphine, hydromorphone, and hydrocodone/oxycodone, respectively. The indicated strains were cultured in closed batch fermentations in media supplemented with 1 mM thebaine (equivalent to 311 mg/L). Culture medium was analyzed at the end of the fermentation for a panel of opioids through LC-MS. (b) Cell density and concentrations of key opioids (hydrocodone, dihydrocodeine, and oxycodone) as a function of time for the fermentation of yeast strain CSY952. At indicated time points, samples were taken, diluted, and analyzed for cell density through spectrometry and opioid production through LC-MS.
Figure 22:
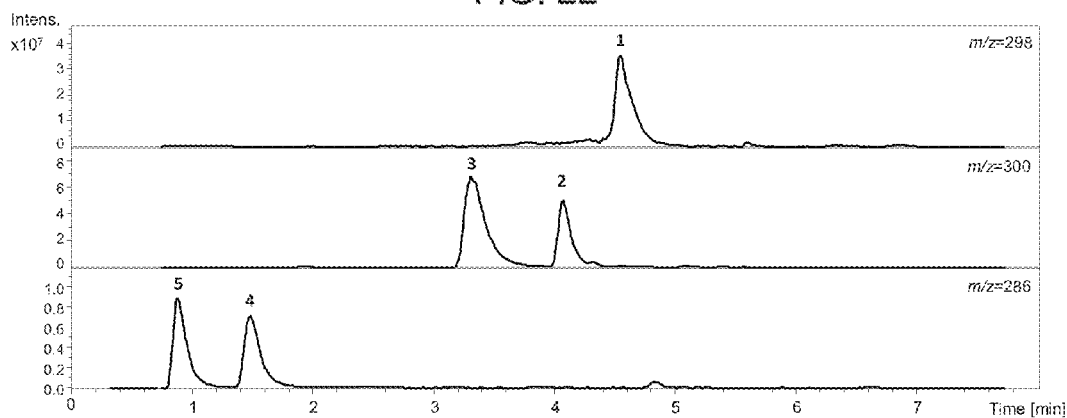
FIG. 22 depicts liquid chromatography tandem mass spectrometry (LCMS) analysis of metabolites secreted into the culture medium by an engineered yeast strain. The strain expresses *Papaver somniferum* T6ODM, COR1.3 and CODM and was cultured for 96 hours in the presence of thebaine. The LCMS peaks 1-5 correspond to the MS2 fragmentation patterns for codeinone, codeine, neopine, morphine and neomorphine.
Figure 22:
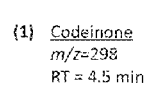
Figure 22:
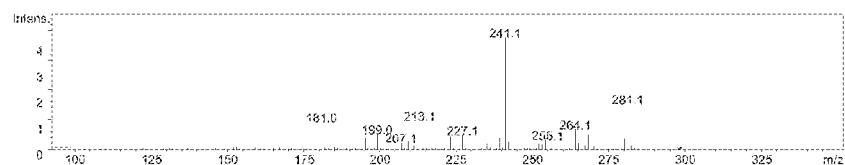
Figure 22:
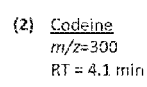
Figure 22:
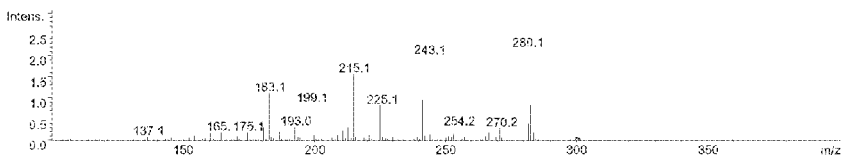
Figure 22:
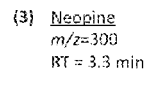
Figure 22:
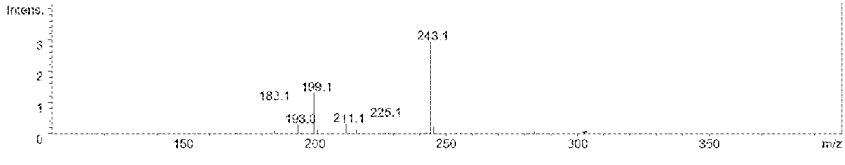
Figure 22:
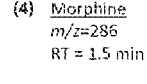
Figure 22:
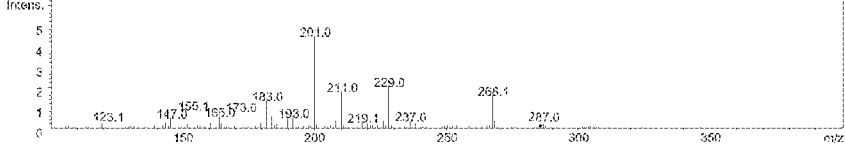
Figure 22:
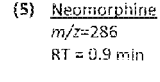
Figure 22:
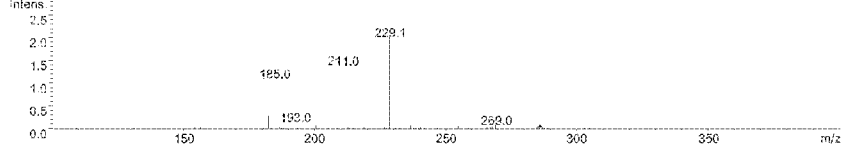

Analysis of the total metabolite profile across strains at the final time point revealed important differences in pathway flux (FIG. 21). Strain CSY950 in which COR was localized to the ER produced low titers of neopine and neomorphine relative to codeine and morphine (2.6 and 0.76 mg/L relative to 7.7 and 4.7 mg/L), indicating that the spatial engineering approach remained effective at limiting pathway flux towards non-target byproducts in bench scale fermentations (FIG. 21a). However, the overall yield of morphine from this strain was lower. Examination of the full BIA profile revealed that the side product 14-hydroxycodeine was a large component of the total opioid molecules produced (15 mg/L). In this strain codeinone may form 14-hydroxycodeinone, which is then reduced by COR to 14-hydroxycodeine. Furthermore, the higher titer of codeine than morphine suggests that factors influencing CODM activity may form a bottleneck in pathway flux to morphine.

Analysis of the CSY951 fermentation culture medium provided more evidence of a bottleneck in pathway flux from codeine to morphine. The products downstream of CODM—morphine, hydromorphone, dihydromorphine—accumulated at low levels (0.54, 1.0, and 1.5 mg/L, respectively) relative to other BIA products, suggesting that activity of CODM may be limited. This could occur due to restricted access of CODM to its substrate codeine as a result of passive diffusion out of the cell facilitated by the intermediate polarity of this molecule, or it may be attributed to binding site competition from thebaine which is plentiful in the culture medium. CSY951 also accumulated low levels of hydrocodone and oxycodone (1.6 and 0.55 mg/L, respectively), consistent with morB$^{E160G}$ limiting production of these side products and routing pathway flux to hydromorphone. In this strain morA activity increased accumulation of side products neopine and neomorphine (21 and 4.4 mg/L, respectively), possibly impacting yields of target end product hydromorphone. The data indicates that further optimization of the hydromorphone production strain may be achieved through a dual spatial-temporal regulation strategy. For example, implementing the spatial engineering approach to localize morA to the ER may support increased production of morphine and limit flux to the neomorphine branch as observed for ER-COR1.3. morA expression could be further temporally regulated to "switch on" once a suitable level of morphine has accumulated and then convert this intermediate to morphinone and ultimately to hydromorphone. A similar temporal regulation strategy applied to morB could limit the synthesis of side products such as hydrocodone and oxycodone.

The CSY952 strain was engineered for the production of hydrocodone and oxycodone and has a simple pathway architecture. The strain does not incorporate morA/COR or CODM and thus does not lose flux to the neomorphine branch nor encounter the bottleneck between codeine and morphine. CSY952 converted thebaine to hydrocodone and oxycodone with titers of 51 and 70 mg/L, respectively (FIG. 21a). Accumulation of hydrocodone was limited by its conversion to dihydrocodeine over the course of the fermentation, with a final titer of 11 mg/L (FIG. 21). The reduction of hydrocodone to dihydrocodeine may be attributed to a second reduction reaction by morB or may be the result of an endogenous yeast enzyme activity. The MS/MS spectra of dihydrocodeine matched published mass spectra. CSY952 demonstrates that high flux to target compounds can be achieved through a minimally branched pathway of heterologous enzymes with high activity in yeast.

3. Discussion

*S. cerevisiae* has been demonstrated as a biosynthetic platform for many valuable BIA target molecules, including as a production host for the transformation of thebaine to opioids including codeine, morphine, hydrocodone, oxycodone, and hydromorphone. The tools and methods support BIA biosynthesis in yeast by regulating the localization of heterologous pathway enzymes and redirecting pathway flux to target end products. Gene copy number optimization and co-substrate supply enhancement were also applied to enhance yeast opiate biosynthesis. For example, three exemplary engineered strains produced 7.7 mg/L codeine and 4.7 mg/L morphine (CSY950), 1 mg/L hydromorphone (CSY951), and 51 mg/L hydrocodone, 11 mg/L dihydrocodeine, and 70 mg/L oxycodone (CSY952) in bench-scale batch fermentations.

In opium poppy, thebaine is converted to morphine via two biosynthetic routes. The initial bifurcation occurs when T6ODM or CODM demethylates thebaine at a distinct position. Since both biosynthetic routes arrive at morphine in opium poppy this bifurcation is unlikely to impact yields in planta. However, the subject engineered yeast strains demonstrate an additional branching due to the activities of COR and CODM on neopinone and neopine, respectively, resulting in production of neomorphine and decreased production of morphine.

The plant enzymes may function differently when expressed in yeast than in the native plant host, due to the absence of native regulatory mechanisms and altered cellular factors such as protein processing, localization, and microenvironment. In the subject engineered yeast strains, production of the intermediates oripavine or morphinone was not observed. In aqueous solution, neopinone rapidly rearranges to codeinone, but this molecule may be stabilized by conditions in the yeast cell. In vitro conditions thus favor codeine production, but in vivo conditions in yeast may slow neopinone rearrangement, allowing COR to act on this intermediate to produce neopine.

T6ODM and CODM exhibit broad substrate specificity, catalyzing O-demethylation of non-morphinan alkaloid substrates such as scoulerine and allocryptopine. These enzymes also catalyze O-demethylation reactions that break methylenedioxy bridges in diverse BIAs, including allocryptopine, cryptopine, and protopine. Other examples of BIA enzyme promiscuity include the O- and N-methyltransferases, which methylate many BIA substrates. In a heterologous microbial host, the absence of native temporal and spatial regulation mechanisms likely further broadens the range of substrates available to the BIA biosynthetic enzymes, leading to newly observed pathway branches and metabolites. In addition, combining enzymes from different species in a single host cell further increases the number of natural and non-native substrates available to any given enzyme and the production of a variety of BIA molecules. Reconstructing targeted microbial BIA biosynthetic pathways can be achieved to manage flux through highly branching pathways to achieve optimal yields of individual target end products.

To facilitate spatial engineering of biosynthetic pathways in yeast, an organelle routing toolkit was created that supports enzyme routing to selected organelles and endomembrane locations. These spatial engineering tools were applied to redirect flux to the target product morphine, limiting production of undesired side products. The spontaneous conversion of neopinone to codeinone was a key branch point in our pathway, where COR activity on neopinone directs flux to neomorphine and its activity on codeinone directs flux to morphine. Isolation of COR from T6ODM may allow additional time for the spontaneous reaction to occur and redirect flux to the morphine branch. The results demonstrate that actively routing COR to different organelles increases pathway specificity for morphine and overall morphine titer, likely through the combined effects of delocalization of pathway enzymes and reduction of COR activity to further balance pathway flux.

The results show the construction of the final steps in opiate biosynthesis in yeast to convert thebaine to codeine and morphine and extension of this pathway to produce the semi-synthetic drugs, e.g., hydrocodone, oxycodone, and hydromorphone. Combined with the total microbial biosynthesis of upstream BIA reticuline, the subject methods and host cells may be used or adapted for engineering a yeast strain capable of producing target opiates from simple sugar sources. Such strains may include functional expression of three known enzymes, including one cytochrome P450 to catalyze the conversion of (R)-reticuline to salutaridine.

4. Methods a. Plasmid and Yeast Strain Construction

Modern molecular biology techniques were used to construct the plasmids and strains. The parent *S. cerevisiae* strain from which strains described in the examples were constructed was haploid W303α (MATα leu2-3, 112 trp1-1 can1-100 ura3-1 ade2-1 his3-11,15). Yeast synthetic complete (SC) amino acid dropout media with 2% dextrose and complex Yeast Peptone Dextrose (YPD) medium containing 200 mg/L G418 sulfate were used for strain construction. Chemically-competent *E. coli* strain TOP10 was used for cloning purposes and was grown in LB medium with the indicated antibiotic concentrations. Custom oligonucleotides were synthesized using standard methods. All heterologous gene sequences were downloaded from GenBank, codon optimized for expression in *S. cerevisiae* using the GeneArt GeneOptimizer program, and synthesized using standard methods. All yeast endogenous promoters, terminators, and organelle targeting sequences were amplified from W303α genomic DNA (Table S3). Polymerases used for PCR were Pfu Hotstart for products less than 2 kb and Expand High Fidelity PCR System for products greater than 2 kb. Plasmids were prepared from *E. coli* using QIAprep columns and Econospin columns. Sequencing was performed using standard methods.

Table S3 depicts YAC Expression Cassettes. Unique promoters and terminators were paired with each gene to construct an expression cassette for incorporation into the YES1 vector.

| Plasmid | Gene | | | Promoter | Terminator |
|---|---|---|---|---|---|
| | Name | Species | GenBank ID[a] | | |
| pCS2656 | T6ODM (1.1 kb) | *Papaver somniferum* | ADD85329.1 | GPD (0.7 kb) | ADH1 (0.2 kb) |
| pCS2661 | COR1.3 (1.0 kb)[b] | *Papaver somniferum* | AAF13738.1 | TPI1 (0.5 kb) | STE2 (0.2 kb) |
| pCS2657 | CODM (1.1 kb) | *Papaver somniferum* | ADD35331.1 | TEF1 (0.4 kb) | CYC1 (0.2 kb) |
| pCS2664 | morA (0.9 kb)[c] | *Pseudomonas putida* M10 | AAB17356.1 | PYK1 (0.9 kb) | MFα1 (0.3 kb) |
| pCS2663 | morB (1.1 kb)[c] | *Pseudomonas putida* M10 | AAC43569.1 | PGK1 (0.7 kb) | PHO5 (0.3 kb) |

[a]Heterologous genes were codon optimized for expression in *S. cerevisiae*.
[b]Isoforms of COR replacing COR1.3 in indicated constructs were: COR1.1, AAF13736.1; COR1.2, AAF13737.1; and COR1.4, AAF13739.1.
[c]Variants replacing morA and morB in indicated constructs were morA$^{C81S}$ and morB$^{E160G}$ respectively.

To express heterologous genes from *P. somniferum* and *P. putida* in W303α, individual expression cassettes were constructed which comprised an open reading frame flanked by a unique promoter and terminator (Table S3) and incorporated into the pYES1L vector. In the initial construction of expression cassettes, individual genes were combined with promoters and terminators by Splicing by Overlap Extension (SOEing) PCR and recombined into Gateway vector pDONR221 (BP Clonase II) for sequence verification and storage. Expression cassettes were then PCR amplified using oligonucleotides designed by the GeneArt High-Order Genetic Assembly online tool, which adds homology regions for gap repair in yeast. 100 ng of each expression cassette PCR was combined with 100 ng linearized pYES1L and transformed into W303α by electroporation. The pYES1L vector contains TRP1 for selection on tryptophan dropout media and an ARS4/CEN5 region such that each newly constructed vector was maintained as a single-copy, episomal plasmid in yeast. pYES1L constructs were verified by PCR screening and sequencing. To propagate the plasmid so that it could be transformed into other yeast background strains, the pYES1L vector was isolated from yeast and transformed into TOP10 *E. coli*, where it was maintained in single copy and selected on LB media with 50 mg/L spectinomycin dihydrochloride pentahydrate. Approximately 2 μg plasmid, enough to transform up to 10 yeast strains, was prepared from 100 mL overnight *E. coli* culture.

To integrate additional gene copies into the yeast genome, expression cassettes comprising a gene flanked by a promoter and terminator were produced by PCR amplification of pUG vectors, which were modified to enable Gateway Cloning (Life Technologies). Vectors pUG6 and pUG73 containing KanMX and *Kluyveromyces lactis* LEU2 selection markers, respectively, were modified to include a GPD promoter and CYC1 terminator flanking the Gateway cassette attR1-ccdB/Cam$^R$-attR2 to generate two new pDEST vectors called pCS2643 and pCS2644. Individual pENTR vectors each containing a gene open reading frame prefixed by a Kozak sequence were recombined with the pDEST vectors. From the resulting vectors, the gene expression cassette and adjoining selection marker (KanMX or LEU2) flanked by loxP sites was PCR amplified with oligonucleotides that added 103 bp of homology to the target integration site in the yeast genome. The PCR product was transformed into W303α by standard lithium acetate transformation. Integration events were selected by growth on G418 or leucine-dropout media and confirmed by PCR screening of both integration borders and by sequencing. The loxP sites were used to remove the selection marker by expression of Cre recombinase (Guldener et al. A new efficient gene disruption cassette for repeated use in budding yeast. Nucleic Acids Res 24, 2519-2524 (1996)).

Other plasmids were constructed from the Lindquist suite of destination vectors, especially pAG416GPD-ccdB (Alberti, S., Gitler, A. D. & Lindquist, S. A suite of Gateway cloning vectors for high-throughput genetic analysis in *Saccharomyces cerevisiae*. Yeast 24, 913-919 (2007). Vectors for microscopy were constructed with the organelle targeting sequence fused to GFP separated by a $Gly_6SerThr$ linker or a $ProGly_6$ linker at the N-terminal or C-terminal, respectively. The targeting sequence, linker and GFP were combined by SOEing PCR and cloned into pDONR221 using BP clonase II. The resulting entry vector was recombined into pAG416GPD-ccdB or another destination vector using LR clonase II to create a shuttle vector for expression in yeast. Plasmids containing established markers for the mitochondria and endoplasmic reticulum were pHS12-mCherry (Addgene plasmid 25444) and YIPlac204TKC-DsRed-Express2-HDEL (Addgene plasmid 21770), respectively.

b. Culture and Fermentation Conditions

To assay for opioid production, yeast strains were cultured in 96-well plates with 0.4 mL SC growth medium (tryptophan-dropout, 2% dextrose) per well and incubated in a shaker at 30° C., 480 rpm agitation, 1.24 cm orbital diameter, with 80% humidity. Strains were initially inoculated into SC medium with 0.5 g/L glutamine substituted for ammonium sulfate as the nitrogen base and grown for 16 h. Cultures were then back-diluted 40× into SC medium with 0.5 g/L glutamine, 2.5 g/L monosodium glutamate, 50 mM 2-oxoglutarate, and 1 mM thebaine. Strains were grown 96 h or until morphine production by the control strain reached approximately 2.5 mg/L. To determine cell density the final $OD_{600}$ (after 10× dilution) was measured).

For enhanced closed-batch culture conditions, strains were cultured in a Biostat Q-plus bioreactor with 0.5 L vessel size. Initial medium volume was 250 mL and contained 10×SC tryptophan dropout medium components supplemented with 5 g/L glutamine, 25 g/L MSG, 100 mM 2-oxoglutarate, and 1 mM thebaine. Glucose concentration was 10% and the medium was further supplemented with 2 g/L adenine hemisulfate. Each vessel was inoculated with a 10 mL overnight culture grown in selective medium which was pelleted and the cells resuspended in the fermentation medium before addition to the vessel. Process parameters were kept constant during the fermentation at 30° C., 200 rpm stirring, and 2 L/min compressed air flow rate. At appropriate time points cell density was recorded from diluted samples measured in a cuvette on a Nanodrop 2000c spectrophotometer and additional samples were taken for metabolite analysis.

c. Analysis of Opiate Production

Opiates secreted into the culture medium by the engineered yeast strains were identified and quantified by liquid chromatography mass spectrometry (LC-MS). Cultures were pelleted by centrifugation and 5 μL of the supernatant separated on a Zorbax SB-Aq column (3.0×50 mm, 1.8 μM particle size). The column was equilibrated with water, 0.1% acetic acid, and 0.1% methanol (Solvent A) and samples were eluted with a mobile phase of methanol and 0.1% acetic acid (Solvent B) in the following sequence: 0-1 min at 100% A, 1-4 min 0-25% B, 4-7 min at 25% B, followed by steps to clean the column with 100% B then re-equilibrate in A. The flow rate was held constant at 0.6 mL/min. Eluted opiates were identified on an Agilent 6320 Ion Trap mass spectrometer operated in scan mode for total ion monitoring. Extracted ion chromatograms for each metabolite of interest were compared with commercially available standards spiked into spent yeast culture medium. Fragment ions for target molecules were identified in MS/MS for both samples and standards and compared to published spectra to confirm the identity of each opiate. For quantification, peak area of the extracted ion chromatograms was integrated and compared to standard curves for each molecule. The standards were thebaine, codeine sulfate, morphine sulfate pentahydrate, hydrocodone bitartrate, oxycodone hydrochloride, hydromorphone hydrochloride.

For analysis of bioreactor culture medium, samples were diluted between 2- and 10-fold and separated on a Zorbax SB-Aq column (3.0×250 mm, 5 μM particle size). The column was equilibrated with water, 0.1% acetic acid, and 0.1% methanol (Solvent A) and samples were eluted with a mobile phase of methanol and 0.1% acetic acid (Solvent B) in the following sequence: 0-10 min at 100% A, 10-30 min 0-90% B followed by steps to clean the column with 100% B then re-equilibrate in A. Flow rate was held constant at 0.8 mL/min.

d. Confocal Microscopy

Yeast cells harboring the appropriate plasmids were grown overnight in SC dropout media then 1.5 mL was pelleted and resuspended at high cell density (in <100 μL medium). Slides were prepared by placing a 2% low-melting point agarose pad combined with yeast media on a microscope slide, spotting 1 μl of yeast cells on the agarose pad, covering with a No. 1. coverslip, and sealing. Cells were imaged on a Leica TCS SP5 confocal microscope with a 63.0× glycerine immersion objective, 1.30× numerical aperture, and up to 8× digital zoom. Hybrid detector (HyD) smart gain was adjusted from 30-200% depending on sample fluorescence intensity. As an example of the fluorescence settings, for single-color imaging of GFP the sample was excited with laser line 488 nm and emitted fluorescence was recorded by a HyD channel in the range 500-550 nm (dichroic mirror=DD 488/594). Images were recorded with an airyl pinhole size (108.4 μm), a minimum of 2× line averaging, a pixel size of 30-100 nm, and optical section thickness of 0.856 μm.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of preparing a benzylisoquinoline alkaloid product, the method comprising:
culturing an engineered microbial cell under conditions suitable for protein production, wherein the engineered microbial cell is an opioid-producing engineered microbial cell, wherein the engineered microbial cell comprises a plurality of heterologous coding sequences for encoding a plurality of enzymes within a pathway for producing the benzylisoquinoline alkaloid product, and wherein at least one heterologous coding sequence of the plurality of heterologous coding sequences encodes an enzyme that is within a pathway that converts a thebaine to the benzylisoquinoline alkaloid product wherein the engineered microbial cell is a yeast cell:
adding a starting compound to the cell culture; and
recovering the benzylisoquinoline alkaloid product from the cell culture, wherein the benzylisoquinoline alkaloid product is selected from the group consisting of a neopine, neomorphine, codeinone, codeine, morphine, morphinone, hydrocodone, dihydrocodeine, oxycodone, 14-hydroxycodeine, hydromorphone, and dihydromorphine.

2. The method according to claim 1, wherein the engineered microbial cell comprises:
one or more heterologous coding sequences for encoding one or more enzymes that are selected from the group consisting of Thebaine 6O-demethylase, Codeinone reductase, Codeine O-demethylase, Morphine dehydrogenase, and Morphine reductase.

3. The method of claim 1, wherein the benzylisoquinoline alkaloid product is selected from the group consisting of neopine, neomorphine, codeinone, codeine, morphine, morphinone, hydromorphone, dihydromorphine, hydrocodone, dihydrocodeine, oxycodone, and 14-hydroxy codeine.

4. The method of claim 1, wherein the benzylisoquinoline alkaloid product is selected from the group consisting of neopine, neomorphine, codeinone, codeine, morphine, morphinone, hydromorphone, and dihydromorphine.

5. The method of claim 1, wherein the benzylisoquinoline alkaloid product is selected from the group consisting of hydrocodone, dihydrocodeine, oxycodone, and 14-hydroxycodeine.

6. The method of claim 1, wherein the benzylisoquinoline alkaloid product is produced using one or more of N-methylation, acetalization, hydroxylation, oxidation, reduction, cyclization, dehydration, O-alkylation, demethylation, and isomerization.

7. The method of claim 1, wherein at least one heterologous coding sequence of the plurality of heterologous coding sequences encodes an enzyme that is selected from the group consisting of Norcoclaurine 6-O-methyltransferase, Coclaurine-N-methyltransferase, 4'-O-methyltransferase, and Cytochrome P450 80B 1.

8. The method of claim 1, wherein the engineered microbial cell comprises at least one heterologous coding sequence of the plurality of heterologous coding sequences that encodes an enzyme selected from the group consisting of Morphine dehydrogenase and Morphine reductase.

9. The method according to claim 2, wherein the engineered microbial cell comprises heterologous coding sequences for encoding two enzymes that are involved in the pathway that converts a thebaine into the benzylisoquinoline alkaloid product, each of the two enzymes selected from the group consisting of Thebaine 6-O demethylase, Codeinone reductase, Codeine O-demethylase, Morphine dehydrogenase, and Morphine reductase.

10. The method according to claim 9, wherein the two enzymes are operably connected along the pathway that converts a thebaine into the benzylisoquinoline alkaloid product.

11. The method according to claim 2, wherein the engineered microbial cell comprises heterologous coding sequences for encoding three enzymes that are involved in the pathway that converts a thebaine into the benzylisoquinoline alkaloid product, each of the three enzymes selected from the group consisting of Thebaine 6-O demethylase, Codeinone reductase, Codeine O-demethylase, Morphine dehydrogenase, and Morphine reductase.

12. The method according to claim 11, wherein the three enzymes are operably connected along the pathway that converts a thebaine into the benzylisoquinoline alkaloid product.

* * * * *